US008927586B2

(12) United States Patent
Trojanowski et al.

(10) Patent No.: US 8,927,586 B2
(45) Date of Patent: Jan. 6, 2015

(54) THROMBOXANE A2 (TP) RECEPTOR ANTAGONISTS

(71) Applicant: The Trustees of the University of Pennsylvania, Philadelphia, PA (US)

(72) Inventors: John Q. Trojanowski, Philadelphia, PA (US); Virginia M. Y. Lee, Philadelphia, PA (US); Kurt R. Brunden, Media, PA (US); Amos B. Smith, Merion, PA (US); Donna M. Huym, Allentown, NJ (US); Carlo Ballatore, Philadelphia, PA (US); Anne-Marie Hogan, Mount Merrion (IE); Francesco Piscitelli, Marina di Strongoll (IT); Sugiyama Shimpei, Shizuoka (JP); Xiaozhao Wang, Drexel Hill, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 70 days.

(21) Appl. No.: 13/780,458

(22) Filed: Feb. 28, 2013

(65) Prior Publication Data
US 2013/0165488 A1    Jun. 27, 2013

Related U.S. Application Data

(63) Continuation-in-part of application No. 13/812,793, filed as application No. PCT/US2011/045565 on Jul. 27, 2011.

(60) Provisional application No. 61/368,884, filed on Jul. 29, 2010.

(51) Int. Cl.
| | | |
|---|---|---|
| C07C 311/20 | (2006.01) | |
| C07D 317/28 | (2006.01) | |
| A61K 31/18 | (2006.01) | |
| A61K 31/196 | (2006.01) | |
| A61K 31/216 | (2006.01) | |
| A61K 31/357 | (2006.01) | |
| A61K 31/41 | (2006.01) | |
| A61K 31/4174 | (2006.01) | |
| A61K 31/421 | (2006.01) | |
| A61K 31/426 | (2006.01) | |
| A61K 45/06 | (2006.01) | |
| C07D 233/64 | (2006.01) | |
| C07D 257/04 | (2006.01) | |
| C07D 263/32 | (2006.01) | |
| C07D 277/28 | (2006.01) | |

(52) U.S. Cl.
CPC ............... *A61K 31/18* (2013.01); *A61K 31/196* (2013.01); *A61K 31/216* (2013.01); *A61K 31/357* (2013.01); *A61K 31/41* (2013.01); *A61K 31/4174* (2013.01); *A61K 31/421* (2013.01); *A61K 31/426* (2013.01); *A61K 45/06* (2013.01); *C07C 311/20* (2013.01); *C07D 233/64* (2013.01); *C07D 257/04* (2013.01); *C07D 263/32* (2013.01); *C07D 277/28* (2013.01); *C07D 317/28* (2013.01)
USPC .............. 514/381; 560/10; 548/252; 549/491

(58) Field of Classification Search
CPC ................................................... A61K 31/415
See application file for complete search history.

(56) References Cited

U.S. PATENT DOCUMENTS

| 5,472,979 A | 12/1995 | Lavielle et al. |
|---|---|---|
| 2009/0075976 A1 | 3/2009 | Verbeuren et al. |
| 2013/0190370 A1* | 7/2013 | Trojanowski et al. ........ 514/381 |

OTHER PUBLICATIONS

Audoly, et al., "Cardiovascular responses to the isoprostanes iPF(2alpha)-III and IPE(2)-III are mediated via the thromboxane A(2) receptor in vivo." 2000, Circulation 101:2833-2840.
Austin, et al., "Partitioning of ionizing molecules between aqueous buffers and phospholipid vesicles." 1995, J Pharm Sci. 84:1180-1183.
Benzing, et al., "Evidence for glial-mediated inflammation in aged APP(SW) transgenic mice." 1999, Neurobiol Aging 20:581-589.
Chaer, et al., "Platelet function and pharmacologic inhibition." 2006, Vasc Endovascular Surg. 40:261-267.
Dogne, et al., "From the design to the clinical application of thromboxane modulators." 2006, Curr Pharm Des. 12:903-923 (abstract).
Elmhurst, et al., "Intestinal effects of isoprostanes: evidence for the involvement of prostanoid EP and TP receptors." 1997, J Pharmacol Exp Ther. 282:1198-1205.
Giulian, et al., "Activated microglia are the principal glial source of thromboxane in the central nervous system." 1996, Neurochem Int 29:65-76.
Hata et al., "Pharmacology and signaling of prostaglandin receptors: multiple roles in inflammation and immune modulation." 2004, Pharmacol Ther. 103:147-166.
Masereel, et al., "Recent developments of thromboxane modulators" 2001, Exp. Opin. Ther. Patents 11(11):1663-1675 (abstract).
McGeer and McGeer., "Inflammation, autotoxicity and Alzheimer disease." 2001, Neurobiol Aging 22:799-809.
Narumiya and Fitzgerald, "Genetic and pharmacological analysis of prostanoid receptor function." 2001, J Clin Invest 108:25-30.
Pajouhesh and Lenz, "Medicinal chemical properties of successful central nervous system drugs." 2008, NeuroRx 2:541-553.
Raychowdhury, et al., "Alternative splicing produces a divergent cytoplasmic tail in the human endothelial thromboxane A2 receptor," 1994, J Biol Chem. 269:19256-19261.
Sapra et al., "Anti-amyloid treatments in Alzheimer's disease." 2009, Recent Pat CNS Drug Discov 4(2):143-8 (Abstract).
Shineman, et al., "Thromboxane receptor activation mediates isoprostane-induced increases in amyloid pathology in Tg2576 mice." 2008, J. Neurosci 28:4785-4794.
Slepko, et al., "Reorientation of prostanoid production accompanies "activation" of adult microglial cells in culture." 1997, J Neurosci Res. 49:292-300.

* cited by examiner

*Primary Examiner* — Melenie McCormick
*Assistant Examiner* — Taina D Matos Negron
(74) *Attorney, Agent, or Firm* — Saul Ewing, LLP; Kathryn Doyle

(57) ABSTRACT

The present invention relates to novel TP receptor antagonists, which optionally cross the blood-brain barrier of a mammal. The invention also provides methods for treating a disorder related to activation of TP receptor utilizing the compounds of the invention.

2 Claims, 21 Drawing Sheets

| Compound | X | hRLB K$_d$ (nM) | mRLB K$_d$ (nM) |
|---|---|---|---|
| 51278 | | 100 (+/- 70) | 36 (+/- 12) |
| 51279 | | 0.65 (+/- 0.20) | 0.5 (+/- 0.4) |
| 51280 | | 0.015 (+/- 0.0002) | 0.005 (+/- 0.001) |
| 51281 | | 220 (+/- 120) | 19 (+/- 30) |
| 51326 | | 240 (+/- 110) | 12 (+/- 11) |
| 51354 | | 290 (+/- 120) | 50 (+/- 40) |
| 51356 | | nd | nd |
| 51414 | | 113 (+/- 56) | 34 (+/- 25) |
| 51417 | | 115 (+/- 57) | 63 (+/- 83) |
| 51418 | | 201 (+/- 52) | 5.9 (+/- 2.2) |

| Compound | X | hIP1 IC₅₀ (nM) | mIP1IC₅₀ (nM) |
|---|---|---|---|
| 51278 | | 475 (+/- 331) | 10 (+/- 7.9) |
| 51279 | | 5 (+/- 4) | 1 (+/- 1) |
| 51280 | | 0.014 (+/- 0.01) | 0.02 (+/- 0.01) |
| 51281 | | 633 (+/- 496) | 34 (+/- 30) |
| 51326 | | 529 (+/- 139) | nd |
| 51354 | | 2740 (+/- 480) | 646 (+/- 300) |
| 51356 | | 2530 (+/- 1240) | 321 (+/- 71) |
| 51414 | | 349 (+/- 157) | 49 (+/- 14) |
| 51417 | | 92 (+/- 43) | 0.62 (+/- 1.0) |
| 51418 | | 282 (+/- 163) | 47 (+/- 63) |
| 51455 | | 391 (+/- 192) | 68 (+/- 33) |

| Compound | X | Plasma (nM) | Brain (nM) |
|---|---|---|---|
| 51278 | | nd | nd |
| 51279 | | 2070 (+/- 799) | 20 (+/- 5.7) |
| 51288 | | nd | nd |
| 51281 | | 66 (+/- 60) | 151 (+/- 131) |
| 51326 | | 103 (+/- 42.5) | 7.4 (+/- 2.7) |
| 51354 | | 563 (+/- 47) | 1228 (+/- 194) |
| 51356 | | 4038 (+/- 911) | 76 (+/- 29) |
| 51414 | | 195 (+/- 45) | 406 (+/- 66) |
| 51417 | | 449 (+/- 223) | 9.7 (+/- 6.9) |
| 51418 | | 109 (+/- 45) | 77 (+/- 36) |
| 51455 | | 3.8 (+/- 6.7) | 14 (+/- 3.3) |

Cmpd 40 – oxazole      CNDR-51536 – imidazole ent therefore has certain rights in this invention.

THROMBOXANE A2 (TP) RECEPTOR ANTAGONISTS

CROSS-REFERENCE TO RELATED APPLICATION

This application is a continuation-in-part and claims priority to U.S. patent application Ser. No. 13/812,793, filed Jan. 28, 2013, which is a national phase application filed under 35 U.S.C. §371 and claims priority to International Patent Application No. PCT/US2011/045565, filed Jul. 27, 2011, and published under PCT Article 21(2) in English, which is entitled to priority under 35 U.S.C. §119(e) to U.S. Provisional Patent Application No. 61/368,884, filed Jul. 29, 2010, each of which applications is hereby incorporated by reference in its entirety herein.

STATEMENT REGARDING FEDERALLY SPONSORED RESEARCH OR DEVELOPMENT

This invention was made with government support under grant numbers AG11542, AG34140 and T32-GM07229 awarded by the National Institutes of Health. The Government therefore has certain rights in this invention.

BACKGROUND OF THE INVENTION

A hallmark pathology of the Alzheimer's Disease (AD) brain is the presence of extracellular senile plaques that are comprised primarily of Aβ peptides (Hardy et al., 2002, Science 297:353-356; Selkoe et al., 2003, Ann. Rev. Pharmacol. Toxicol. 43:545-584) formed after APP is cleaved by β- and γ-secretases (Selkoe et al., 2007, Cell 131:215-221; Dominguez, et al., 2004, Neurodegener. Dis. 1:168-174; Lundkvist et al., 2007, Curr. Opin. Pharmacol. 7:112-118). Certain familial forms of AD (Tanzi et al., 2001, Neuron 32:181-184; St. George-Hyslop et al., 2005, C. R. 328:119-130) are caused by mutations within APP that result in an increased production of both Aβ1-40 and Aβ1-42 or in the ratio of the more amyloidogenic Aβ1-42 relative to Aβ1-40. Other inherited cases of AD result from mutations in presenilin 1 (PS1) or PS2 that are integral to γ-secretase activity, with a resulting increase in Aβ1-42 production. The genetic evidence linking familial AD mutations to alterations in Aβ production has strengthened substantially the "amyloid" hypothesis of AD pathogenesis, although the cause of Aβ deposition in sporadic AD is still not fully understood. Moreover, there is still uncertainty about how Aβ contributes to the neurodegeneration observed in AD, and a number of hypotheses have been forwarded ranging from direct toxic effects of Aβ oligomers (Watson, et al., 2005, Neurol. Res. 27:869-881; Walsh, et al., 2002, Biochem. Soc. Trans. 30:552-557; Walsh et al., 2005, Biochem. Soc. Trans. 33:1087-1090) or fibrils (Lorenzo et al., 1996, Neurobiol. Alzheimer's Dis. 777:89-95) to indirect mechanisms whereby multimeric Aβ leads to increased inflammation (McGeer et al., 2001, Neurobiol. Aging 22:799-809; Benzing, et al., 1999, Neurobiol. Aging 20:581-589; Yates, et al., 2000, J. Neurochem. 74:1017-1025) and/or oxidative stress (Chauhan et al., 2006, Pathophysiology 13:195-208; Sayre, et al., 2008, Chem. Res. Toxicol. 21:172-188; McDonald, et al., 1997, J. Neurosci. 17:2284-2294). Gaining a better understanding of the causes of pathologic Aβ formation and how it triggers neurodegeneration could reveal new therapeutic approaches for AD.

There is compelling evidence that the AD brain is under significant oxidative stress (Sayre, et al., 2008, Chem. Res. Toxicol. 21:172-188), as illustrated by a marked elevation of oxidized lipids (Montine, et al., 2004, Chem. Phys. Lipids 128:117-124; Pratico, et al., 2000, Ann. Neurol. 48:809-812; Forman, et al., 2007, Neurology 68:757-763; Markesbery et al., 2007, Arch. Neurol. 64:954-956) including the F2α-isoprostanes, iPF2αIII and iPF2αVI, which are stable non-enzymatic products of free radical damage to arachidonic acid. Both brain tissue and cerebrospinal fluid (CSF) from patients with AD and mild cognitive impairment (MCI) (Montine, et al., 2004, Chem. Phys. Lipids 128:117-124; Pratico, et al., 2000, Ann. Neurol. 48; 809-812; Forman, et al., 2007, Neurology 68:757-763; Markesbery, et al., 005, Ann. Neurol. 58: 730-735; Casadesus, et al., 2007, Mol. Neurodeg. 2:2-9) have increased iPF2α, which might serve as an early marker of AD neuropathology. This interpretation is bolstered by data showing a significant longitudinal elevation of CSF iPF2α in MCI patients over a 2-year interval (de Leon, et al. 2006, Neurobiol. Aging. 27:394-401; Brys, et al., 2009, Neurobiol. Aging. 30:682-690). Significantly, iPF2α levels are also elevated in the well-established Tg2576 transgenic mouse model of AD and, importantly, this increase precedes the appearance of Aβ deposits (Pratico, et al., 2001, J. Neurosci. 21:4183-4187). These observations further suggest that brain oxidation is an early event in AD pathogenesis.

Aβ can form redox complexes with metals like copper that might directly lead to oxidative reactions (Smith, et al., 2007, Biochim. Biophys. Acta 1768:1976-1990; Donnelly, et al., 2007, Curr. Opin. Chem. Biol. 11:128-133). Moreover, activated microglia residing in proximity to senile plaques can release a variety of pro-inflammatory and oxidative agents, including superoxide anions and nitric oxide (Yates, et al., 2000, J. Neurochem. 71:1017-1025; McDonald, et al., 1997, J. Neurosci. 17:2284-2294; McGeer et al., 2001. Neurobiol. Aging 22:799-809; Block et al., 2007, Nat. Rev. Neurosci. 8:57-69). The elevation of iPF2α in MCI patients (de Leon, et al., 2006, Neurobiol. Aging. 27:394-401; Brys, et al., 2009, Neurobiol, Aging) 30:682-690) and Tg mice prior to Aβ plaque development (Pratico, et al., 2001, J. Neurosci. 21:4183-4187) suggest that early oxidative events may spur further pathological changes in the AD brain. In fact, important recent studies (Shineman, et al., 2008, J. Neurosci. 28:4785-4794) reveal that the formation of iPF2α in Tg2576 mice that express mutated human APP can trigger a further up-regulation of Aβ production. iPF2αIII can initiate a specific biological effect through activation of the thromboxane A2 (TxA2) receptor (also referred to as the TP receptor) (Audoly, et al., 2000, Circulation 101:2833-2840; Elmhurst, et al., 1.997, J. Pharmacol. Exp. Ther. 282:1198-1205), and iPF2αIII binding to neuronal TP receptors results in an elevation of APP via stabilization of APP mRNA, with a consequent increase of Aβ release (Shineman, et al., 2008, J. Neurosci. 28:4785-4794). Moreover, long-term treatment of Tg2576 mice with a known TP receptor antagonist, S-18886, caused a significant diminution of plaque load relative to untreated mice. In addition to iPF2α, TxA2 itself may also be up-regulated in the AD brain as a result of its release from activated microglia (Benzing, et al., 1999, Neurobiol. Aging 20:581-589; McGeer et al., 2001. Neurobiol. Aging 22:799-809; Giulian, et al., 1996. Neurochem. Int. 29:65-76; Slepko, et al., 1997, J. Neurosci. Res. 49:292-300). Thus, there is evidence that TP receptors play an important role in AD disease progression by increasing Aβ production in response to both brain oxidation and inflammation. The TP receptor, a member of the highly-druggable G-protein coupled receptor (GPCR) family, is therefore a rational AD therapeutic target.

The discovery and development of TxA2 receptor antagonists (also referred to as TP receptor antagonists) has been an objective of many pharmaceutical companies for approximately 30 years (Dogne J-M, et al., Exp. Opin. Ther. Patents 11: 1663-1675 (2001)). Preclinical pharmacology has established that this class of compounds has effective antithrombotic activity obtained by inhibition of the thromboxane pathway. These compounds also prevent vasoconstriction induced by TxA2 and other prostanoids that act on the TxA2 receptor within the vascular bed. Unfortunately, however, the Phase II/III trials of TxA2 antagonists have not proven successful, and none of these compounds have reached the marketplace in the United States.

There remains a need in the art for identifying novel therapeutic agents that are useful in preventing or treating AD in a mammal. The present invention fills this need.

BRIEF SUMMARY OF THE INVENTION

The invention includes a method of treating a disease or disorder associated with activation of a TP receptor in a mammal in need thereof. The method comprises administering to the mammal a therapeutically effective amount of a TP receptor antagonist compound of Formula (I), or a salt or solvate thereof:

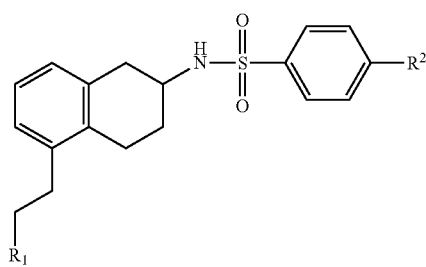

(I)

wherein $R^1$ is selected from the group consisting of

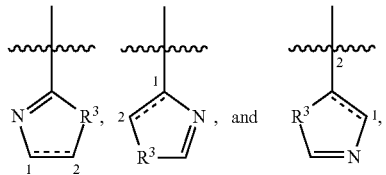

wherein each carbon is optionally substituted, the bond between carbons 1 and 2 is either a single bond ($C^1$-$C^2$) or a double bond ($C^1$=$C^2$); $R^2$ is selected from the group consisting of F, Br, I, and $CF_3$, $R^3$ is selected front the group consisting of $NR^4$, S, and O, $R^4$ is selected from the group consisting of H, —($C_1$-$C_6$ alkyl), —($C_1$-$C_6$ fluoroalkyl), —($C_1$-$C_6$ heteroalkyl), —($C_1$-$C_3$ alkyl)-($C_3$-$C_6$ cycloalkyl), —($C_1$-$C_3$ aryl), —($C_1$-$C_3$ alkyl)-heteroaryl, —C(=O)$R^5$, —$CO_2R^5$, and —CH($R^5$)$_2$, and each occurrence of $R^5$ is independently selected from the group consisting of H, —($C_1$-$C_6$ alkyl), —($C_1$-$C_6$ heteroalkyl), and —($C_1$-$C_3$ alkyl)-($C_3$-$C_6$ cycloalkyl), wherein the alkyl, heteroalkyl, or cycloalkyl group is optionally substituted.

In one embodiment, the compound is selected from the group consisting of 4-chloro-N-(5-(2-(oxazol-2-yl)ethyl)-1,2,3,4-tetrahydronaphthalen-2-yl)benzenesulfonamide, 4-chloro-N-(5-(2-(thiazol-2-yl)ethyl)-1,2,3,4-tetrahydronaphthalen-2-yl)benzenesulfonamide, 4-chloro-N-(5-(2-(2-methylthiazol-4-yl)ethyl)-1,2,3,4-tetrahydronaphthalen-2-yl)benzenesulfonamide, 4-chloro-N-(5-(2-(oxazol-4-yl) ethyl)-1,2,3,4-tetrahydronaphthalen-2-yl) benzenesulfonamide, N-(5-(2-(1H-imidazol-2-yl)ethyl)-1,2,3,4-tetrahydronaphthalen-2-yl)-4-chlorobenzenesulfonamide, N-(5-(2-(1H-imidazol-5-yl) ethyl)-1,2,3,4-tetrahydronaphthalen-2-yl)-4-chlorobenzenesulfonamide, 4-fluoro-N-(5-(2-(thiazol-2-yl) ethyl)-1,2,3,4-tetrahydronaphthalen-2-yl) benzenesulfonamide, a salt thereof a solvate thereof, and any combinations thereof.

In one embodiment, the antagonist crosses the blood-brain barrier in the mammal. In another embodiment, the antagonist does not cross the blood-brain barrier in the mammal. In yet another embodiment, the mammal is a human.

In one embodiment, the disorder associated with activation of a TP receptor in the mammal is a neurodegenerative disorder. In another embodiment, the neurodegenerative disorder is selected from the group consisting of Alzheimer's disease, scrapie, bovine spongiform encephalitis, Creutzfeldt-Jakob disease, Cerebral Amyloid Angiopathy, and other amyloid or prion protein related disorders. In yet another embodiment, the compound is administered to the mammal orally, parenterally, intravascularly, intranasally, or intrabronchially. In yet another embodiment, the compound modulates central nervous system function of the mammal. In yet another embodiment, the compound inhibits activation of a TP receptor or a TP-like receptor on a cell of the central nervous system, whereby the cell does not mediate the disease or disorder. In yet another embodiment, the compound binds to a TP receptor or a TP-like receptor.

In one embodiment, the compound is administered in combination with a second therapeutic agent comprising anti-amyloid medicament. In yet another embodiment, the second therapeutic agent is administered simultaneously, prior to, or after administration of the compound. In yet another embodiment, the second therapeutic agent is co-administered with the compound. In yet another embodiment, the second therapeutic agent is co-administered and co-formulated with the compound.

The invention further includes a composition comprising a compound of Formula (I), or a salt or solvate thereof:

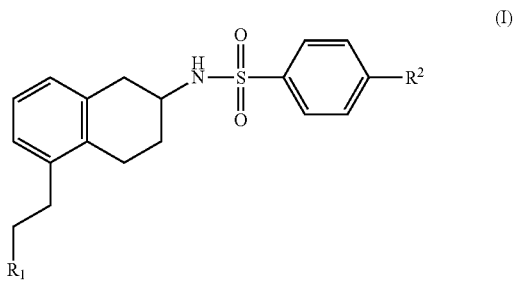

(I)

wherein $R^1$ is selected from the group consisting of

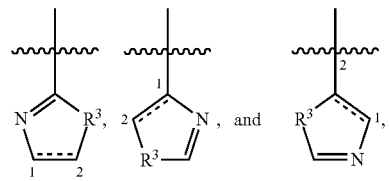

wherein each carbon is optionally substituted, the bond between carbons 1 and 2 is either a single bond ($C^1$-$C^2$) or a double bond ($C^1$=$C^2$), $R^2$ is selected from the group consisting of F, Cl, Br, I, and $CF_3$, $R^3$ is selected from the group consisting of $NR^4$, S, and O, $R^4$ is selected from the group consisting of H, —($C_1$-$C_6$ alkyl), —($C_1$-$C_6$ fluoroalkyl), —($C_1$-$C_6$ heteroalkyl), —($C_1$-$C_3$ alkyl)-($C_3$-$C_6$ cycloalkyl), —($C_1$-$C_3$ alkyl)-aryl, —($C_1$-$C_3$ alkyl)-heteroaryl, —C(=O)$R^5$, —$CO_2R^5$, and —CH($R^5$)$_2$, and each occurrence of $R^5$ is independently selected, from the group consisting of H, —($C_1$-$C_6$ alkyl), —($C_1$-$C_6$ heteroalkyl), and —($C_1$-$C_3$ alkyl)-($C_3$-$C_6$ cycloalkyl), wherein the alkyl, heteroalkyl, or cycloalkyl group is optionally substituted.

In one embodiment, the compound is selected from the group consisting of 4-chloro-N-(5-(2-(oxazol-2-yl)ethyl)-1,2,3,4-tetrahydronaphthalen-2-yl)benzenesulfonamide, 4-chloro-N-(5-(2-(thiazol-2-yl)ethyl)-1,2,3,4-tetrahydronaphthalen-2-yl)benzenesulfonamide, 4-chloro-N-(5-(2-(2-methylthiazol-4-yl)ethyl)-1,2,3,4-tetrahydronaphthalen-2-yl)benzenesulfonamide, 4-chloro-N-(5-(2-(oxazol-4-yl)ethyl)-1,2,3,4-tetrahydronaphthalen-2-yl)benzenesulfonamide-(5-(2-(1H-imidazol-2-yl)ethyl)-1,2,3,4-tetrahydronaphthalen-2-yl)-4-chlorobenzenesulfonamide, N-(5-(2-(1H-imidazol-5-yl)ethyl)-1,2,3,4-tetrahydronaphthalen-2-yl)-4-chlorobenzenesulfonamide, 4-fluoro-N-(5-(2-(thiazol-2-yl)ethyl)-1,2,3,4-tetrahydronaphthalen-2-yl)benzenesulfonamide, a salt thereof a solvate thereof, and any combinations thereof.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 12, comprising

FIGS. 13A-13D, is a series of graphs illustrating how TP receptor activation increases APP protein levels, Aβ secretion and APP mRNA. FIG. 13A is a graph illustrating that activation of the hTP receptor with I-BOP (structure shown in inset) increases APP protein levels, as demonstrated by Western blot and quantified by densitometric analysis of the ratio of APP/α-tubulin, HEK293 cells stably co-expressing hAPP and hTP receptor were treated with I-BOP at the indicated concentrations. FIG. 13B is a graph illustrating that activation of the hTP receptor with I-BOP increases production of Aβ(1-40) by HEK293 cells co-expressing hAPP and hTP receptor. Aβ(1-40) levels in the media were measured by ELISA. FIG. 13C is a graph illustrating that increases in Aβ(1-40) release induced by treatment of HEK293 cells co-expressing hAPP and hTP with 0.8 nM I-BOP can be blocked by treatment with 10 μM of the known TP antagonists, daltroban and S-18886 (FIG. 1). FIG. 13D is a series of graphs illustrating that TP receptor activation results in increased APP mRNA levels in HEK293 cells co-expressing hAPP and either hTP or in TP receptors. Cells were treated with 10 nM I-BOP in the absence or presence of 10 μM S-18886, and APP mRNA levels were measured by qPCR and normalized to GAPDH mRNA. All values are presented as mean±SD, ***p<0.001 as determined by ANOVA and Tukey posthoc analysis.

FIGS. 14A-14D, is a series of graphs illustrating the analysis of TP receptor-mediated increases of IP1. FIG. 14A is a graph illustrating how I-BOP binding to the hTP or mTP receptor results in increased production of IP1. HEK293 cells stably expressing the hTP receptor or mTP receptor were treated for 1 h with I-BOP at the indicated concentrations, and IP1 was measured as described elsewhere herein. FIG. 14B is a graph illustrating that the TP receptor antagonist, S-18886 (FIG. 1), inhibits I-BOP-induced increases of IP1. HEK293 cells expressing the hTP or mTP receptors were incubated with varying concentrations of S-18886 for 15 min, followed by the addition of 0.8 nM of I-BOP for 1 h. FIG. 14C is a graph illustrating that I-BOP concentration—response curves were obtained at varying fixed concentrations of SQ-25,548 (as shown in legend; structure illustrated in FIG. 1) by measuring IP1 formation in HEK293 cells expressing the mTP receptor. FIG. 14D is a graph illustrating the Schild plot of the I-BOP concentration response curves from FIG. 14C, with the x-intercept being equal to the Kd value. The $K_d$ value derived from the mTP receptor Schild plot was 3.2±1.4 nM, and a similar analysis for the hTP receptor yielded a $K_d$ value of 6.9±3.9 nM. All values represent mean±SD.

FIGS. 16A-16B, illustrates a comparison of SQ-29,548 and compound 40 (4-chloro-N-(5-(2-(oxazol-2-yl)ethyl)-1,2,3,4-tetrahydronaphthalen-2-yl)benzenesulfonamide) activities in the hTP and mTP receptor IP1 functional assay. FIG. 16A is a graph illustrating that cells expressing the hTP or mTP receptors were treated for 15 min with varying concentrations of SQ-29,548 or 40, followed by a 1 h treatment with 0.2 nM I-BOP before determining relative IP1 levels. The calculated $IC_{50}$ values for SQ-29,548 with the cells expressing the hTP and mTP receptor were 360±140 and 55.6±31.9 nM, respectively. The corresponding values for compound 40 were 307±109 and 79.8±58.2 nM. FIG. 16B is a Schild plot of MOP concentration response curves upon addition of increasing concentrations of compound 40 in HEK293 cells stably expressing the hTP receptor (left) and mTP receptors (right). The $K_d$ value derived from the hTP receptor Schild plot was 6.0±2.9 nM, and a $K_d$ value of 2.9±1.2 nM was obtained from the mTP Schild plot. All data points represent mean±SD.

FIGS. 17A-17B, illustrates that compounds 40 and 48 reduce the I-BOP-induced APP protein expression and Aβ(1-40) production by HEK293 cells expressing hTP receptor (FIG. 17A) or in TP receptor (FIG. 17B). Cells were pretreated for 1 h with 10 μM of 40 or 48, or DMSO, followed by I-BOP (10 nM) for 48 h. Control cells did not receive test compound or I-BOP. APP levels were determined by immunoblotting and normalized to tubulin, Aβ(1-40) was determined by ELISA measurement of culture medium. All values represent mean±SD*p<0.05, p<0.01, *p<0.001, as determined by ANOVA and Tukey posthoc analysis.

DETAILED DESCRIPTION OF THE INVENTION

Figure 1:
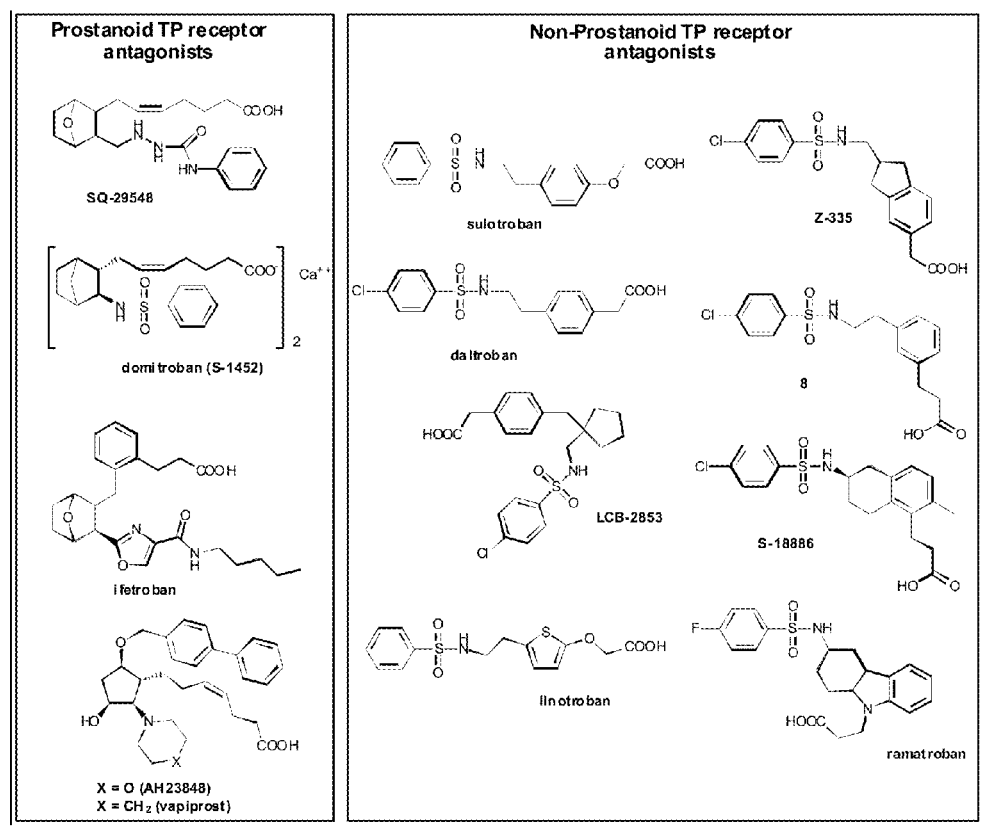
FIG. 1 illustrates non-limiting examples of known TP receptor antagonists.

The present invention provides novel compositions that are useful in treating a neurodegenerative disease or disorder, including but not limited to, Alzheimer's disease (AD). The present invention further provides methods for treating a neurodegenerative disease or disorder. In one aspect, the invention relates on the discovery that known thromboxane A2 (TxA2) receptor (also called the TP receptor) antagonists, including but not limited to tetrahydronaphtalenes (THNPs), can be modified to improve their ability to cross the blood-brain barrier. Exemplary THNPs are disclosed in EP 0 648 741 A1. In one embodiment, administering a compound of the invention to a mammal results in minimized peripheral compound concentrations and therapeutically effective compound concentrations in the brain. In another embodiment, the compound antagonizes a TP receptor. In yet another embodiment, the compound crosses the blood-brain barrier more effectively than prior art compounds.

DEFINITIONS

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

The term "about," as used herein when referring to a measurable value such as an amount, a temporal duration, and the like, is meant to encompass variations of ±20% or ±10%, more preferably ±5%, even more preferably ±1%, and still more preferably ±0.1%

A "receptor" is a molecule that binds with a ligand.

A "TP receptor antagonist" is a composition of matter which detectably inhibits a biological activity attributable to activation of a TP receptor.

By the term "an inhibitor of a TP receptor," as used herein, is meant any compound or molecule that detectably inhibits activation of a TP receptor or signaling via a TP receptor. Such compounds include an antagonist, an inverse agonist, and the like.

"Activation of a TP receptor," as used herein, means that binding of a natural ligand with a TP receptor on a cell induces the typical cascade of intracellular and extracellular events associated with such binding. A non-limiting example of a natural ligand to a TP receptor is iPT2αIII or thromboxane A2.

By the term "modulating" central nervous system function, as used herein, is meant mediating a detectable increase or decrease in the function of the central nervous system in a mammal compared with the level of central nervous system function in the mammal in the absence of a treatment or compound, and/or compared with the level of central nervous function in an otherwise identical but untreated mammal. The term encompasses perturbing and/or affecting a native signal or response thereby mediating a beneficial therapeutic response in a mammal, preferably, a human. In some instances, modulating central nervous system function is associated with modulating the activity of cells of the central nervous system.

As used herein, the terms "Alzheimer's disease" and "Alzheimer's" refer to a neurodegenerative disorder and encompass familial Alzheimer's disease and sporadic Alzheimer's disease. The term "familial Alzheimer's disease" refers to Alzheimer's disease associated with genetic factors (i.e. inheritance is demonstrated) while "sporadic Alzheimer's disease" refers to Alzheimer's disease that is not associated with prior family history of the disease. Symptoms indicative of Alzheimer's disease in human subjects typically include, but are not limited to, mild to severe dementia, progressive impairment of memory (ranging from mild forgetfulness to disorientation and severe memory loss), poor visual spatial skills, personality, changes, poor impulse control, poor judgment, distrust of others, increased stubbornness, restlessness, poor planning ability, poor decision making, and social withdrawal. In severe cases, patients lose the ability to use language and communicate, and require assistance in personal hygiene, eating and dressing, and are eventually bedridden. Hallmark pathologies within brain tissue include extracellular neuritic amyloid plaques, neurofibrillary tangles, neurofibrillary degeneration, granulovascular neuronal degeneration, synaptic loss, and extensive neuronal cell death.

As used herein, the terms "Alzheimer's patient," "Alzheimer's disease patient," and "individual diagnosed with Alzheimer's disease" refer to an individual or subject who has been diagnosed with Alzheimer's disease or has been given a probable diagnosis of Alzheimer's Disease.

The terms "Aβ," "Aβ peptide" and "Amyloid-β" peptide are synonymous, and refer to one or more peptide compositions of about 38-43 amino acids derived from Beta Amyloid Precursor Protein (β-ApP), as described herein. Disaggregated Aβ means soluble, monomeric and oligomeric peptide units of Aβ. One method to prepare monomeric Aβ is to dissolve lyophilized peptide in neat DMSO with sonication. The resulting solution is centrifuged to remove any insoluble particulates. Aggregated Aβ is a mixture oligomers in which the monomeric units are held together by noncovalent bonds. Furthermore, APP695, APP751, and APP770 refer, respectively, to the 695, 751, and 770 amino acid residue long polypeptides encoded by the human APP gene. See Kang et al., 1987, Nature 325, 773; Ponte et al., 1988, Nature 331, 525; and Kitaguchi et al., 1988, Nature 331, 530. Amino acids within the human amyloid precursor protein (APP) are assigned numbers according to the sequence of the APP770 isoform. Terms such as Aβ39, Aβ40, Aβ41, Aβ42 and Aβ43 refer to an Aβ peptide containing amino acid residues 1-39, 1-40, 1-41, 1-42 and 1-43.

The term "amyloid related diseases" refers to diseases associated with the accumulation of amyloid which can either be restricted to one organ, "localized amyloidosis," or spread to several organs, "systemic amyloidosis," Secondary amyloidosis may be associated with chronic infection (such as tuberculosis) or chronic inflammation (such as rheumatoid arthritis), including a familial form of secondary amyloidosis which is also seen in Familial Mediterranean Fever (FMF) and another type of systemic, amyloidosis found in long-term hemodialysis patients. Localized forms of amyloidosis include, without limitation, diabetes type II and any related disorders thereof, neurodegenerative diseases such as scrapie, bovine spongiform encephalitis, Creutzfeldt-Jakob disease, Alzheimer's disease, Cerebral Amyloid Angiopathy, and other prion protein related disorders.

The terms "patient," "subject," "individual," and the like are used interchangeably herein, and refer to any mammal. In certain non-limiting embodiments, the patient, subject or individual is a human.

By the term "applicator," as the term is used herein, is meant any device including, but not limited to, a hypodermic syringe, a pipette, an iontophoresis device, a patch, and the like, for administering the compound of the invention to a mammal.

The term "bioavailability" refers to the extent to which, and sometimes the rate at which, the active moiety of a drug or metabolite enters systemic circulation, thereby gaining access to the site of action. Medications that are administered intravenously are considered to have 100 percent bioavailability, that is, the complete dose of the medication reaches the systemic circulation. But drugs that are administered through other routes, such as the oral route, generally do not have 100 percent bioavailability because these drugs may have various degrees of absorption. In particular it is desired to obtain quicker and larger and/or more complete uptake of the active compound, and thereby provide for a reduction of the administered, dosages or for a reduction in the number of daily administrations.

Traditionally, bioavailability determination from plasma concentration-time data usually involves administering the compound to a human or other animal, withdrawing blood samples intravenously at certain times, and determining the maximum (peak) plasma drug concentration, the time at which maximum plasma drug concentration occurs (peak time), and the area under the plasma concentration-time curve (AUC). In oral dosing, the plasma drug concentration increases with the extent of absorption; the peak is reached when a "pseudo-equilibrium" exists between the drug elimination rate and the absorption rate. Because drug elimination begins once the drug enters the bloodstream, determining bioavailability solely based on peak plasma concentration may be misleading. Peak time is also used as an index for absorption rate, because slower absorption rates result in later peak times. Therefore, researchers often select AUC as a more reliable measure of bioavailability.

A "disease" is a state of health of an animal wherein the animal cannot maintain homeostasis, and wherein if the disease is not ameliorated, the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

The term to "treat," as used herein, means reducing the frequency with which symptoms are experienced by an individual or subject or administering an agent or compound to reduce the frequency with which symptoms are experienced. In some instances, "treat" and "treating" are not limited to the case where the subject (e.g. patient) is cured and the disease is eradicated. Rather, the present invention also contemplates treatment that merely reduces symptoms, improves (to some degree) and/or delays disease progression. The term "treatment" also refers to the alleviation, amelioration, and/or stabilization of symptoms, as well as delay in progression of symptoms of a particular disorder. For example, "treatment" of Alzheimer's disease includes any one or more of: elimination of one or more symptoms of Alzheimer's disease, reduction of one or more symptoms of Alzheimer's disease, stabilization of the symptoms of Alzheimer's disease (e.g., failure to progress to more advanced stages of Alzheimer's disease), and delay in progression (i.e., worsening) of one or more symptoms of Alzheimer's disease.

As used herein, "treating a disease or disorder" means reducing the frequency with which a symptom of the disease or disorder is experienced by an individual. Disease and disorder are used interchangeably herein.

As used herein, to "alleviate" a disease means reducing the severity of one or more symptoms of the disease.

The term "effective amount" in a mammal, as used herein, refers to an amount that provides a therapeutic or prophylactic benefit in the mammal.

The term "therapeutically effective amount" refers to the amount of the subject compound that will elicit the biological or medical response of a tissue, system, animal or human that is being sought by the researcher, veterinarian, medical doctor or other clinician. The term "therapeutically effective amount" includes that amount of a compound that, when administered, is sufficient to prevent development of, or alleviate to some extent, one or more of the symptoms of the condition or disorder being treated. The therapeutically effective amount will vary depending on the compound, the disease and its severity and the age, weight, etc., of the mammal to be treated.

By the term "substantially crosses the blood-brain bonier," as used herein, means that the inhibitor detectably crosses the blood-brain barrier as assessed using standard assays such as those disclosed herein, known in the art, or such assays as are developed in the future to determine the permeability of a compound across the blood-brain barrier. For example, such assays include assessing the concentration of the compound beyond the barrier, or an art-recognized model of the blood-brain barrier, over time to determine the permeability of the compound through the barrier.

"Instructional material," as that term is used herein, includes a publication, a recording, a diagram, or any other medium of expression which can be used to communicate the usefulness of the nucleic acid, peptide, and/or compound of the invention in the kit for effecting alleviating or treating the various diseases or disorders recited herein. Optionally, or alternately, the instructional material may describe one or more methods of alleviating the diseases or disorders in a cell or a tissue of a mammal. The instructional material of the kit may, for example, be affixed to a container that contains the nucleic acid, peptide, and/or compound of the invention or be shipped together with a container that contains the nucleic acid, peptide, and/or compound. Alternatively, the instructional material may be shipped separately from the container with the intention that the recipient uses the instructional material and the compound cooperatively.

"Pharmaceutically acceptable" refers to those properties and/or substances that are acceptable to the patient from a pharmacological/toxicological point of view and to the manufacturing pharmaceutical chemist from a physical/chemical point of view regarding composition, formulation, stability, patient acceptance and bioavailability. "Pharmaceutically acceptable carrier" refers to a medium that does not interfere with the effectiveness of the biological activity of the active ingredient(s) and is not toxic to the host to which it is administered.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound or molecule useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound or molecule useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the language "pharmaceutically acceptable salt" refers to a salt of the administered compounds prepared from pharmaceutically acceptable non-toxic acids, including inorganic acids, organic acids, solvates, hydrates, or clathrates thereof.

As used herein, the term "composition," "pharmaceutical composition" or "pharmaceutically acceptable composition" refers to a mixture of at least one compound or molecule useful within the invention with a pharmaceutically acceptable carrier. The pharmaceutical composition facilitates administration of the compound or molecule to a patient. Multiple techniques of administering a compound or molecule exist in the art including, but not limited to, intravenous, oral, aerosol, parenteral, ophthalmic, pulmonary and topical administration.

As used herein, the term "substituted" means that an atom or group of atoms has replaced hydrogen as the substituent attached, to another group. The term "substituted" further refers to any level of substitution, namely mono-, di-, tri-, tetra-, or pentasubstitution, where such substitution is permitted. The substituents are independently selected, and substitution may be at any chemically accessible position. In one embodiment, the substituents vary in number between one and four. In another embodiment, the substituents vary in number between one and three. In yet another embodiment, the substituents vary in number between one and two.

As used herein, "compound 40" refers to 4-chloro-N-(5-(2-(oxazol-2-yl)ethyl)-1,2,3,4-tetrahydronaphthalen-2-yl) benzenesulfonamide or a salt or solvate thereof.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range and, when appropriate, partial integers of the numerical values within ranges. For example, description of a range such as from 1 to 6 should be considered to have specifically disclosed subranges such as from 1 to 3, from 1 to 1, from 1 to 5, from 2 to 4, from 2 to 6, from 3 to 6 etc., as well as individual numbers within that range for example, 1, 2, 2.7, 3, 1, 5, 5.3, and 6. This applies regardless of the breadth of the range.

DESCRIPTION

The present invention provides novel compositions that are useful in treating a neurodegenerative disease or disorder, such as but not limited to Alzheimer's disease (AD). In one embodiment, the compositions of the invention are antagonists of the IP receptor and cross the blood-brain barrier.

In one aspect, existing TP receptor antagonists contain a carboxylic acid moiety that interferes with their ability to diffuse across the blood-brain barrier. Accordingly, in one embodiment the invention relates to the discovery that, through isosteric replacement and pro-drug approaches to chemically modify existing IP receptor antagonists, the ability of the compounds to penetrate the brain can be improved. In another embodiment, the compounds of the invention achieve greater concentration in the brain than in the plasma in a mammalian model, thereby demonstrating that the compounds are freely diffusible across the blood-brain barrier.

In one aspect, administering to a mammal a TP antagonist compound of the invention affords low peripheral levels of the compound while maintaining therapeutically effective brain concentrations of the compound. Thus, the compounds of the invention have greater therapeutic windows than standard drugs, and may be used as AD therapeutics.

One of skill in the art would also appreciate, based upon the disclosure provided herein, that the invention encompasses a method of treating a neurodegenerative disorder using the compositions of the invention, whereby administering to a mammal a TP antagonist compound of the invention yields a therapeutically efficacious amount of the compound in the brain. This is because the compositions of the invention exhibit an improved ability to penetrate the brain. In some instances, a therapeutic level in the brain is achieved when the concentration of free composition in the brain is approximately equal to that in the plasma.

In one aspect, the chemical structure of known TP receptor antagonists and related tetrahydronaphtalenes (THNPs) can be modified to generate derivatives with improved brain penetration, according to the methodology described herein.

Compounds

The compounds of the present invention may be synthesized using techniques well-known in the art of organic synthesis. The starting materials and intermediates required for the synthesis may be obtained from commercial sources or synthesized according to methods known to those skilled in the art.

In one aspect, the compound of the invention is a compound of formula (I), or a salt, solvate, or N-oxide thereof:

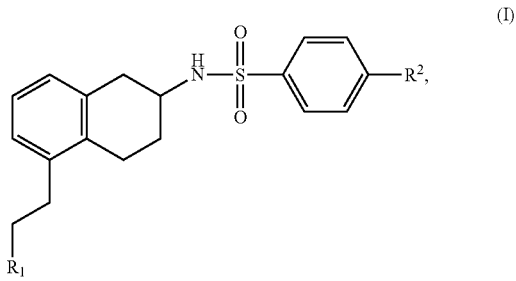

(I)

wherein:

R$^1$ is selected from the group consisting of

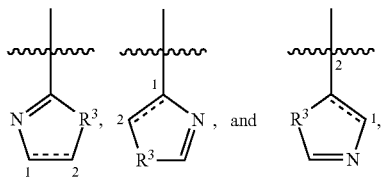

, and wherein each carbon is optionally substituted;

the bond between carbons 1 and 2 is either a single bond (C$^1$-C$^2$) or a double bond (C$^1$=C$^2$);

R$^2$ is selected from the group consisting of F, Cl, Br, I, and CF;

R$^3$ is selected from the group consisting of NR$^4$, S, and O;

R$^4$ is selected from the group consisting of H, —(C$_1$-C$_6$ alkyl), —(C$_1$-C$_6$ fluoroalkyl), —(C$_1$-C$_6$ heteroalkyl), —(C$_1$-C$_3$ alkyl)-(C$_3$-C$_6$ cycloalkyl), —(C$_1$-C$_3$ alkyl)-aryl, —(C$_1$-C$_3$ alkyl)-heteroaryl, —C(=O)R$^5$, —CO$_2$R$^5$, and —CH(R)$_2$; and, each occurrence of R$^5$ is independently selected from the group consisting of H, —(C$_1$-C$_6$ alkyl), —(C$_1$-C$_6$ heteroalkyl), and —(C$_1$-C$_3$ alkyl)-(C$_3$-C$_6$ cycloalkyl), wherein the alkyl, heteroalkyl, or cycloalkyl group is optionally substituted.

In one embodiment, the compound of the invention is selected from the group consisting of 4-chloro-N-(5-(2-(oxazol-2-yl)ethyl)-1,2,3,4-tetrahydronaphthalen-2-yl)benzenesulfonamide, 4-chloro-N-(5-(2-(thiazol-2-yl)ethyl)-1,2,3,4-tetrahydronaphthalen-2-yl)benzenesulfonamide, 4-chloro-N-(5-(2-(2-methylthiazol-4-yl)ethyl)-1,2,3,4-tetrahydronaphthalen-2-yl)benzenesulfonamide, 4-chloro-N-(5-(2-(oxazol-4-yl)ethyl)-1,2,3,4-tetrahydronaphthalen-2-yl)benzenesulfonamide, N-(5-(2-(1H-imidazol-2-yl)ethyl)-1,2,3,4-tetrahydronaphthalen-2-yl)-4-chlorobenzenesulfonamide, N-(5-(2-(1H-imidazol-5-yl)ethyl)-1,2,3,4-tetrahydronaphthalen-2-yl)-4-chlorobenzenesulfonamide, 4-fluoro-N-(5-(2-(thiazol-2-yl)ethyl)-1,2,3,4-tetrahydronaphthalen-2-yl)benzenesulfonamide, a salt thereof, a solvate thereof, a N-oxide thereof, and any combinations thereof.

In one embodiment, the compounds of the invention bind to a TP receptor, preferably, the compounds bind to a TP receptor and inhibit activity of the TP receptor. As a non-limiting example, THNPs were modified to improve the ability to cross the blood-brain barrier. Exemplary modifications to THNPs include carboxylic acid (CNDR-51280), tetrazole (CNDR-51279), trifluoroethyl amide (51418), trifluoromethyl alcohol (51354), propyl alcohol (51281), and dioxolane (51414) (see inter alia FIGS. 2-4). However, the invention is not limited to the abovementioned compounds having such modifications. Rather, any compound substance that binds to a TP receptor and is modified to improve the ability to cross the blood-brain barrier is included in the invention.

One skilled in the art when armed with the present disclosure would understand that the compounds of the invention can allosterically modulate, e.g., allosterically potentiate/enhance or suppress/attenuate, the ability of the corresponding receptor to be bound by other compounds. Thus, it is contemplated that the compounds of the invention can behave as allosteric modulators of a TP receptor.

The invention includes methods of modifying existing TP receptor antagonists, thereby increasing the ability of the compounds of the invention to cross the blood-brain barrier. Exemplary modified TP receptor antagonists are disclosed herein, hut the present application is in no way limited to these or any other particular derivatives of TP receptor antagonists. Instead, the invention encompasses arty compound having the desired TP receptor antagonist characteristics, while also possessing the desired enhanced ability to cross the blood-brain barrier. The production and identification of compounds having these characteristics are routine in the art once armed with the specification, as are assays for assessing the permeability of a compound through the blood-brain barrier. Such assays are exemplified herein, as are methods of producing compounds of interest having the desired characteristics. Nonetheless, the present invention is in no way limited to these, or any other, methods in particular; rather, it includes methods of producing and identifying compounds that exhibit improved ability to cross the blood-brain barrier and still inhibit cellular signaling via a TP receptor or a TP-like receptor such as those disclosed herein, known in the art, or to be developed in the future.

The compounds of the invention can be prepared by a person skilled in the art of synthetic organic chemistry once armed with the specification. The person skilled in the art knows how to select and implement appropriate synthetic routes. Suitable synthetic methods may be identified by reference to the literature describing synthesis of analogous compounds, and then performing the synthesis of the desired compound following the route used for the analogous compounds, modifying the starting materials, reagents, and reaction conditions as appropriate to synthesizing any particular desired compounds. In addition, reference may be made to sources such as Comprehensive Organic Synthesis, Ed, B. M, Trost and I. Fleming (Pergamon Press 1991), Comprehensive Organic Functional Group Transformations, Ed, A. R. Katritzky, O. Meth Cohn, and C. W. Rees (Pergamon Press, 1996), Comprehensive Organic Functional Group Transformations II, Ed. A. R. Katritzky and R. J. K. Taylor (Editor) (Elsevier, 2nd Edition, 2004), Comprehensive Heterocyclic Chemistry, Ed. A. R. Katritzky and C. W. Rees (Pergamon Press, 1984), and Comprehensive Heterocyclic Chemistry D. Ed. A. R. Katritzky, C. W. Rees, and E. F. V. Scriven (Pergamon Press, 1996), the entire disclosures of which are incorporated herein by reference.

It will be understood that when compounds of the invention contain one or more chiral centers, the compounds may exist in, and may be isolated as pure enantiomeric or diastereomeric forms or as racemic mixtures. The present invention therefore includes any possible enantiomers, diastereomers, racemates or mixtures thereof of the compounds of the invention that are efficacious in the treatment of a neurodegenerative disorder.

The isomers resulting from the presence of a chiral center comprise a pair of non-superimposable isomers that are called "enantiomers." Single enantiomers of a pure compound are optically active, i.e., they are capable of rotating the plane of plane polarized light.

The present invention is meant to encompass diastereoisomers as well as their racemic and resolved, diastereomerically and enantiomerically pure forms and salts thereof. Diastereoisomeric pairs may be resolved by known separation techniques including normal and reverse phase chromatography, and crystallization.

By "isolated optical isomer" means a compound that has been substantially purified from the corresponding optical isomer(s) of the same formula. Preferably, the isolated isomer is at least about 80%, more preferably at least 90% pure, even more preferably at least 98% pure, most preferably at least about 99% pure, by weight.

Diasteromeric mixtures can be purified by standard by standard chromatography methods or by crystallization. Enantiomers may be purified, from racemic mixtures by well-known chiral separation techniques. According to one such method, a racemic mixture of a compound having the structure of Formula or a chiral intermediate thereof, is separated into 99% wt. % pure optical isomers by HPLC using a suitable chiral column, such as a member of the series of DAICEL® CHIRALPAK® family of columns (Daicel Chemical Industries, Ltd., Tokyo, Japan). The column is operated according to the manufacturer's instructions.

The invention includes prodrugs of the compounds of the invention. "Prodrug," as used herein, means a compound which is convertible in vivo by metabolic means (e.g., by hydrolysis) to a compound of the present invention, Various forms of prodrugs are known in the art, for example, as discussed in Bundgaard, (ed.), Design of Prodrugs, Elsevier (1985); Widder et al. (ed.), Methods in Enzymology, vol. 4, Academic Press (1985); Krogsgaard-Larsen et al. (ed), "Design and Application of Prodrugs," Textbook of Drug Design and Development, Chapter 5, 113-191 (1991), Bundgaard et al., 1992, J. Drug Deliv. Rev. 8:1-38, Bundgaard, 1988. J. Pharm. Sci. 77:285 et seq.; and Higuchi and Stella (eds.), Prodrugs as Novel Drug Delivery Systems, American Chemical Society (1975). In a non-limiting embodiment, the esters and amides of the alpha-carboxylic acid are prepared as prodrugs to improve oral bioavailability, whereby the ester or amide is stable in the stomach and gastrointestinal tract, is optimally transported across the lining of the gastrointestinal tract into the bloodstream, and is then converted by the ubiquitous esterases or amidases in the blood, to the carboxylic acid moiety. In a non-limiting embodiment, the ester prodrug is the methyl, ethyl, n-propyl or i-propyl ester. In another non-limiting embodiment, the amide prodrug is the isopropyl amide or the 2,2,2-trifluoroethyl amide.

Salts

The compounds useful within the invention may form salts with acids or bases, and such salts are included in the present invention. In one embodiment, the salts are pharmaceutically-acceptable salts. The term "salts" embraces addition salts of free acids or free bases that are compounds useful within the invention. The term "pharmaceutically acceptable salt" refers to salts that possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds useful within the invention.

Suitable pharmaceutically-acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, mane, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid.

Suitable pharmaceutically acceptable base addition salts of compounds useful within the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (N-methylglucamine) and procaine. Examples of pharmaceutically unacceptable base addition salts include lithium salts and cyanate salts. All of these salts may be prepared from the corresponding compound by reacting, for example, the appropriate acid or base with the compound.

Methods

The invention includes a method of treating a disease or disorder associated with activation of a TP receptor in a mammal in need thereof. The method comprises administering to the mammal a therapeutically effective amount of a TP receptor antagonist compound of Formula (I), or a salt or solvate thereof:

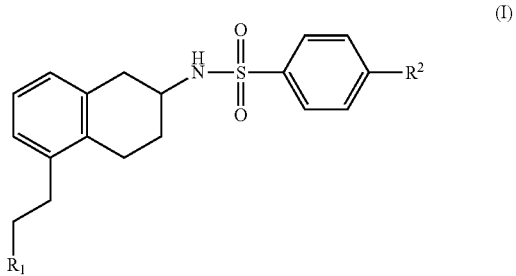

(I)

wherein $R^1$ is selected from the group consisting of

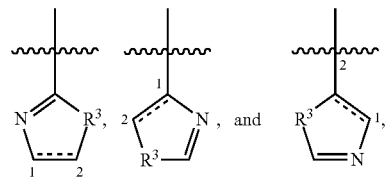

wherein each carbon is optionally substituted, the bond between carbons 1 and 2 is either a single bond ($C^1$-$C^2$) or a double bond ($C^1$=$C^2$); $R^2$ is selected from the group consisting of F, Cl, Br, L and $Cl_3$, $R^3$ is selected from the group consisting of $NR^4$, S, and O, $R^4$ is selected from the group consisting of H, —($C_1$-$C_6$ alkyl), —($C_1$-$C_6$ fluoroalkyl), —($C_1$-$C_6$ heteroalkyl), —($C_1$-$C_3$ alkyl)-($C_3$-$C_6$ cycloalkyl), —($C_1$-$C_3$ alkyl)-aryl, —($C_1$-$C_3$ alkyl)-heteroaryl, —C(=O)$R^5$, —$CO_2R^5$, and —$CH(R^5)_2$, and each occurrence of $R^5$ is independently selected from the group consisting of H, —($C_1$-$C_6$)—($C_1$-$C_6$ heteroalkyl), and ($C_1$-$C_3$ alkyl)-($C_3$-$C_6$ cycloalkyl), wherein the alkyl, heteroalkyl, or cycloalkyl group is optionally substituted.

In one embodiment, the compound is selected from the group consisting of 4-chloro-N-(5-(2-(oxazol-2-yl)ethyl)-1, 2,3,4-tetrahydronaphthalen-2-yl)benzenesulfonamide, 4-chloro-N-(5-(2-(thiazol-2-yl)ethyl)-1,2,3,4-tetrahydronaphthalen-2-yl)benzenesulfonamide, 4-chloro-N-(5-(2-(2-methylthiazol-4-yl)ethyl)-1,2,3,4-tetrahydronaphthalen-2-yl)benzenesulfonamide, 4-chloro-N-(5-(2-(oxazol-4-yl)ethyl)-1,2,3,4-tetrahydronaphthalen-2-yl) benzenesulfonamide, N-(5-(2-(1H-imidazol-2-yl)ethyl)-1,2, 3,4-tetrahydronaphthalen-2-yl)-4-chlorobenzenesulfonamide, N-(5-(2-(1H-imidazol-5-yl) ethyl)-1,2,3,4-tetrahydronaphthalen-2-yl)-4-chlorobenzenesulfonamide, 4-fluoro-N-(5-(2-(thiazol-2-yl) ethyl)-1,2,3,4-tetrahydronaphthalen-2-yl) benzenesulfonamide, a salt thereof a solvate thereof and any combinations thereof.

In one embodiment, the antagonist crosses the blood-brain barrier in the mammal. In another embodiment, the antagonist does not cross the blood-brain barrier in the mammal. In yet another embodiment, the mammal is a human.

In one embodiment, the disorder associated with activation of a TP receptor in the mammal is a neurodegenerative disorder. In another embodiment, the neurodegenerative disorder is selected from the group consisting of Alzheimer's disease, scrapie, bovine spongiform encephalitis, Creutzfeldt-Jakob disease, Cerebral Amyloid Angiopathy, and other amyloid and prion protein related disorders. In yet another embodiment, the compound is administered to the mammal orally, parenterally, intravascularly, intranasally, or intrabronchially. In yet another embodiment, the compound modulates central nervous system function of the mammal. In yet another embodiment, the compound inhibits activation of a TP receptor or a TP-like receptor on a cell of the central nervous system, whereby the cell does not mediate the disease or disorder. In yet another embodiment, the compound binds to a TP receptor or a TP-like receptor.

In one embodiment, the compound is administered in combination with a second therapeutic agent comprising anti-amyloid medicament. In yet another embodiment, the second therapeutic agent is administered simultaneously, prior to, or after administration of the compound. In yet another embodiment, the second therapeutic agent is co-administered with the compound. In yet another embodiment, the second therapeutic agent is co-administered and co-formulated with the compound.

The invention includes methods of treating a neurodegenerative disease or disorder, such as but not limited to Alzheimer's disease, scrapie, bovine spongiform encephalitis, Creutzfeldt-Jakob disease, Cerebral Amyloid Angiopathy, and other amyloid and prion protein related disorders, in a mammal in need thereof. Preferably, the method comprises administering a therapeutically effective amount of a compound of the invention to the mammal. In one embodiment, contacting a TP receptor with a compound of the invention inhibits activation or signaling of the TP receptor.

In one embodiment, the invention includes a method of the prophylaxis or treatment of a neurodegenerative disorder, comprising administering a composition of the invention to a mammal in need of such treatment, wherein the amount of the composition is sufficient for the prophylaxis or treatment of the neurodegenerative disorder in the mammal.

Without wishing to be bound by any particular theory, it is believed that the ability of the compounds of the invention to regulate the biological activity of a cell expressing a TP receptor provides a method of treating a neurodegenerative disorder. For example, the compounds of the invention can be used to modulate cellular activity upon binding and inhibiting TP receptor and downstream signaling.

Dosing

The compounds of the invention, alone or in combinations with existing therapeutic agents used to treat a neurodegenerative, can be administered to a cell, a tissue, or an animal to provide a therapeutic effect. Methods for the safe and effective administration of the compounds of the invention are known to those skilled in the art. For instance, the administration of TP receptor antagonists is described in the standard literature.

Subject doses of the compounds of the invention typically range from about 0.1 μg/day to 10,000 mg/day, more typically from about 1 μg/day to 1000 mg/day, and most typically from about 10 μg/day to 100 mg/day and any and all whole or partial increments there between.

Stated in terms of subject body weight, typical dosages range from about 0.1 μg/kg/day to 1000 mg/kg/day, more typically from about 10 μg/kg/day to 500 mg/kg/day, more typically front about 20 μg/kg/day to 100 mg/kg/day, more typically from about 50 μg/kg/day to 50 mg/kg/day, and most typically from about 0.10 mg/kg/day to 5 mg/kg/day and any and all whole or partial increments there between.

Subject oral doses of the compounds of the invention typically range from about 0.1 μg/day to 10,000 mg/day, more typically from about 1 μg/day to 1000 mg/day, yet more typically from about 10 μg/day to 100 mg/day, and most typically 8 mg/day to 80 mg/day and any and all whole or partial increments there between.

Stated in terms of subject body weight, typical oral dosages range from about 0.1 μg/kg/day to 1000 mg/kg/day, more typically from about 10 μg/kg/day to 500 mg/kg/day, more typically from about 20 μg/kg/day to 100 mg/kg/day, more typically from about 50 μg/kg/day to 50 mg/kg/day, and most typically from about 0.10 mg/kg/day to 5 mg/kg/day and any and all whole or partial increments there between.

The compositions of the invention for administration can be administered in a dose range of from about 1 ng to about 10,000 mg, about 5 ng to about 9,500 mg, about 10 ng to about 9,000 mg, about 20 ng to about 8,500 mg, about 30 ng to about 7,500 mg, about 40 ng to about 7,000 mg, about 50 ng to about 6,500 mg, about 100 ng to about 6,000 mg, about 200 ng to about 5,500 mg, about 300 rig to about 5,000 mg, about 400 ng to about 4,500 mg, about 500 ng to about 4,000 mg, about 1 μg to about 3,500 mg, about 5 μg to about 3,000 mg, about 10 μg to about 2,600 mg, about 20 μg to about 2,575 mg, about 30 μg to about 2,550 mg, about 40 μg to about 2,500 mg, about 50 μg to about 2,475 mg, about 100 μg to about 2,450 mg, about 200 μg to about 2,425 mg, about 300 μg to about 2,000, about 400 μg to about 1,175 mg, about 500 μg to about 1,150 mg, about 0.5 mg to about 1,125 mg, about 1 mg to about 1,100 mg, about 1.25 mg to about 1,075 mg, about 1.5 mg to about 1,050 mg, about 2.0 mg to about 1,025 mg, about 2.5 mg to about 1,000 mg, about 3.0 mg to about 975 mg, about 3.5 mg to about 950 mg, about 4.0 mg to about 925 mg, about 4.5 mg to about 900 mg, about 5 mg to about 875 mg, about 10 mg to about 850 mg, about 20 mg to about 825 mg, about 30 mg to about 800 mg, about 40 mg to about 775 mg, about 50 mg to about 750 mg, about 100 mg to about 725 mg, about 200 mg to about 700 mg, about 300 mg to about 675 mg, about 400 mg to about 650 mg, about 500 mg, or about 525 mg to about 625 mg, and any and all whole or partial increments there between.

In some embodiments, the dose of a composition of the invention is between about 0.0001 mg and about 25 mg. In sonic embodiments, a dose of a composition of the invention used in compositions described herein is less than about 100 mg, or less than about 80 mg, or less than about 60 mg, or less than about 50 mg, or less than about 30 mg, or less than about 20 mg, or less than about 10 mg, or less than about 5 mg, or less than about 2 mg, or less than about 0.5 mg. Similarly, in some embodiments, a dose of a second compound as described herein is less than about 1000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments there between.

Pharmaceutical Composition

For administration of a compound of the present invention to a mammal, the compound can be suspended in any pharmaceutically acceptable carrier, for example, sterile water or buffered aqueous carriers, such as glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey), the disclosure of which is incorporated by reference as if set forth in its entirety herein.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited, to, Ringer's solution, isotonic sodium chloride solution, and fixed oils such as synthetic mono- or di-glycerides.

The compounds of the invention are preferably administered to the subject as a pharmaceutical or veterinary composition, which includes systemic and topical formulations. Among these, preferred are formulations suitable for inhalation, or for respirable, buccal, oral, rectal, vaginal, nasal, intrapulmonary, ophthalmic, optical, intracavitary, intratracheal, intraorgan, topical (including buccal, sublingual, dermal and intraocular), parenteral (including subcutaneous, intradermal, intramuscular, intravenous and intraarticular) and transdermal administration, among others. The route(s) of administration will be readily apparent to the skilled artisan and will depend upon any number of factors including the type and severity of the disease being treated, the type and age of the veterinary or human patient being treated.

The compounds of the invention may be administered to the lungs of a subject by any suitable means, but are preferably administered by generating an aerosol or spray comprised of respirable, inhalable, nasal or intrapulmonarily delivered particles comprising the active compound, which particles the subject inhales, i.e. by inhalation administration. The respirable particles may be liquid or solid. Particles comprising the active compound for practicing the present invention should include particles of respirable or inhalable size; that is, particles of a size sufficiently small to pass through the mouth and larynx upon inhalation and into the bronchi and alveoli of the lungs, in general, particles ranging from about 0.05, about 0.1, about 0.5, about 1, about 1.5 to about 5, about 6, about 7, about 8, about 10 microns in size, more particularly particles about 0.5 to less than about 5 microns in size, are respirable or inhalable. When particles of nonrespirable size are included in the aerosol or spray, they tend to deposit in the throat and be swallowed. Thus, the quantity of non-respirable particles in the aerosol or spray is preferably minimized when intended for respirable administration or by inhalation. For nasal or intrapulmonary administration, a particle size in the range of about 10, about 11, about 15, about 20 to about 25, about 30, about 40, about 50, and sometimes even up to about 100 and about 500 microns is preferred to ensure retention in the nasal or pulmonary cavity. Pulmonary instillation is particularly useful in treating newborns.

Liquid pharmaceutical compositions of the active compound for producing an aerosol or spray may be prepared by combining the active compound with a stable vehicle, such as sterile pyrogen free water. Solid particulate compositions containing respirable dry particles of micronized active compound may be prepared by grinding dry active compound with a mortar and pestle, and then passing the micronized composition through a 400 mesh screen to break up or separate out large agglomerates. A solid particulate composition comprised of the active compound may optionally contain a dispersant which serves to facilitate the formation of an aerosol. A suitable dispersant is lactose, which may be blended with the active compound in any suitable ratio, e.g., a 1 to 1 ratio by weight. Other therapeutic and formulation compounds may also be included, such as a surfactant to improve the sate of surfactant in the lung and help with the absorption of the active agent.

Aerosols of liquid particles comprising the active compound may be produced by any suitable means, such as with a nebulizer. See, e.g., U.S. Pat. No. 4,501,729. Nebulizers are commercially available devices which transform solutions or suspensions of the active ingredient into a therapeutic aerosol mist either by means of acceleration of a compressed gas, typically air or oxygen, through a narrow venturi orifice or by means of ultrasonic agitation. Suitable compositions for use in nebulizer consist of the active ingredient in liquid carrier, the active ingredient comprising up to 40% w/w of the compositions, but preferably less than 20% w/w, and the carrier is typically water or a dilute aqueous alcoholic solution, preferably made isotonic with body fluids by the addition of, for example sodium chloride. Optional additives include preservatives if the composition is not prepared sterile, for example, methyl hydroxybenzoate, antioxidants, flavoring agents, volatile oils, buffering agents and surfactants.

Aerosols of solid particles comprising the active compound may likewise be produced with any sold particulate medicament aerosol generator. Aerosol generators for administering solid particulate medicaments to a subject produce particles which are respirable, as explained above, and they generate a volume of aerosol containing a predetermined metered dose of a medicament at a rate suitable for human administration. Examples of such aerosol generators include metered dose inhalers and insufflators.

Pharmaceutical compositions that are useful in the methods of the invention may be administered systemically in oral solid formulations, ophthalmic, suppository, aerosol, topical or other similar formulations. In addition to the compounds of the invention, or a biological equivalent thereof, such pharmaceutical compositions may contain pharmaceutically-acceptable carriers and other ingredients known to enhance and facilitate drug administration.

The pharmaceutical compositions described herein can be prepared alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

As used herein, the term "pharmaceutically acceptable carrier" means a chemical composition with which the active ingredient may be combined and which, following the combination, can be used to administer the active ingredient to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology, in general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions that are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs.

A pharmaceutical composition of the invention may be prepared, packaged, or sold in bulk, as a single unit dose, or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the mute by which the composition is to be administered. By way of example, the composition may comprise between 0.1% and 100% (w/w) active ingredient. In addition to the active ingredient, a pharmaceutical composition of the invention may further comprise one or more additional pharmaceutically active agents.

Controlled- or sustained-release formulations of a pharmaceutical composition of the invention may be made using conventional technology.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing liquid molecule and which exhibits a less polar character than water.

A tablet comprising the active ingredient may, for example, be made by compressing or molding the active ingredient, optionally with one or more additional ingredients. Compressed tablets may be prepared by compressing, in a suitable device, the active ingredient in free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate, Known granulating and disintegrating agents include, but are not limited to corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid formulations of a pharmaceutical composition of the invention which are suitable for oral administration may be prepared, packaged, and sold either in liquid form or in the form of a dry product intended thr reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Suppository formulations may be made by combining the active ingredient with a non-irritating pharmaceutically acceptable excipient which is solid at ordinary room temperature (i.e., about 20° C.) and which is liquid at the rectal temperature of the subject (i.e., about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants and preservatives.

In yet another embodiment, compositions of the invention may be administered to the desired location of a mammal by a transdermal patch. A transdermal patch is meant a system capable of delivery of a compound to a mammal via the skin, or any suitable external surface, including mucosal membranes, such as those found inside the mouth. Such delivery systems generally comprise a flexible backing, an adhesive and a compound retaining matrix, the backing protecting the adhesive and matrix and the adhesive holding the whole on the skin of the mammal. On contact with the skin, the compound-retaining matrix delivers the compound to the skin, the compound then passing through the skin into the mammal's system.

Certain embodiments of the invention provide a pharmaceutical preparation/dosage formulation provided in the form of a transdermal patch and formulated for sustained release formulation, in a therapeutically effective amount sufficient to treat a disease associated with activation of an immune cell (e.g., rheumatoid arthritis) in a patient, wherein the dosage formulation, when administered (provided as a patch) to the patient, provides a substantially sustained dose over at least about 2 hours, 4 hours, 6 hours, 8, hours, 2 hours, 20 hours, or at least about 24 hours.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, intravenous, subcutaneous, intraperitoneal, intramuscular, intrasternal injection, bolus injections, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

A pharmaceutical composition of the invention may be prepared, packaged, or sold in a formulation suitable for pulmonary administration via the buccal cavity. Such a formulation may comprise dry particles that comprise the active ingredient and that have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described, herein as being useful in pulmonary delivery are so useful in intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken, i.e., by rapid inhalation through the nasal passage from a container of the powder held close to the nares.

Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed. (1985, Remington's Pharmaceutical Sciences, Mack Publishing Co., Easton, Pa.), which is incorporated herein by reference.

Typically, dosages of the compound of the invention which may be administered to an animal, preferably a human, will vary depending upon any number of factors, including but not limited to, the type of animal and type of disease state being treated, the age of the animal and the route of administration.

The compound can be administered to an animal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the animal, and the like.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

The experiments disclosed herein were designed to generate novel TP receptor antagonists having greater improved brain penetration. The antagonists serve as a novel class of AD therapeutics. The materials and methods employed in these experiments are now described.

IP1 Functional Assay

Functional activity of the TP receptor was measured by homogenous time-resolved fluorescence (HTRF) (IP-One Tb, Cisbio, Bedford, Mass., USA). OBI-HEK 293A (MP Biomedicals, Solon, Ohio, USA) cells were transfected with human TP receptor or mouse TP receptor cDNAs cloned into the peDNA5/TO vector (Invitrogen, Carlsbad, Calif., USA), and stable transformants were selected. Cells were plated at 200,000 cells/mL DMEM containing 4.5 g/L glucose (Invitrogen, Carlsbad, Calif., USA), 10% fetal bovine serum, L-glutamine, and penicillin/streptomycin into 384-well plates (Grenier Bio-One, Monroe, N.C., USA), followed by incubation for 16 hours at 37° C. with 5% $CO_2$.

Culture media was removed and cells were then incubated for 15 min at 37° C. with 5% $CO_2$ in 10 mM Hepes, 1 mM $CaCl_2$, 0.4 mM $MgCl_2$, 4.2 mM KCl, 146 mM NaCl, 5.5 mM glucose, 50 mM LiCl, pH 7.4 (stimulation buffer) containing varying concentrations of test antagonist. I-BOP ([1S-[1α,2α(Z),3β(1E,3S*),4α]]-7-[3-[3-hydroxy-4-(4-iodophenoxy)-1-butenyl]-7-oxabicyclo[2.2.1]hept-2-yl]-5-heptenoic acid) (Cayman Chemicals, Ann Arbor, Mich., USA) was added at a final concentration of 1.6 nM in stimulation buffer and incubated for 1 hour at 37° C. with 5% $CO_2$. D2-labeled IP1 and Tb-labeled Anti-IP1 cryptate were then added in lysis buffer and incubated for 1 hour at 25° C. Plates were then read on a Speetramax M5 microplate reader (Molecular Devices, Sunnyvale, Calif., USA). Data are expressed as the ratio of 665 nm/620 nm fluorescence.

Radioligand Binding Assay

QBI-HEK 293A cells expressing human or mouse TxA2 (TP) receptor were grown as described previously and harvested in phosphate-buffered saline with 1 mM EDTA. The cell pellet was homogenized in a glass homogenizer in 20 mM Hepes, 1 mM EGTA, 0.5 mM DTT with protease inhibitor cocktail. The homogenate was initially centrifuged at 1000×g for 10 minutes at 8° C. to remove cell debris. The homogenate was then centrifuged in a Beckman L8-70M ultracentrifuge (Beckman-Coulter, Brea, Calif., USA) at 21,000 rpm for 30 minutes at 4° C., and the pellet was resuspended in 20 mM Hepes, 1 mM EGTA, 100 mM NaCl. Membrane preparations were normalized to protein level as determined with a BCA assay (ThermoFisher, Rockland, Ill.) and stored at −80° C.

Test antagonists were incubated at 10 different concentrations with 25 µg membrane and 25 nM $^3$H-SQ-29,548 (PerkinElmer, Waltham, Mass., USA) in 50 mM Tris, 4 mM $CaCl_2$, 0.1% ascorbic acid pH 7.5 for 2 hours at 25° C. in 96-well polystyrene plates. Separation of bound from free radioligand was accomplished by rapid vacuum filtration onto 96-well GF/B filter plates (PerkinElmer, Waltham, Mass., USA). Filters were washed 8 times in 50 mM Tris, pH 6.9 and allowed to dry for 16 hours. Plates were sealed and filters dissolved in 50 µL Betaplate Scintillation fluid (PerkinElmer, Waltham, Mass., USA) and read on a scintillation counter. Data are presented as percent total binding as calculated by a minimum of 3 wells containing membrane and $^3$H-SQ-29,548 without antagonist.

Determination of Plasma and Brain Drug Concentrations

One-month old B6C3HF1 female mice were given intraperitoneal injections of compounds at 5 mg/kg. 1 hour after injection, mice were lethally anesthetized with an intraperitoneal injection of ketamine hydrochloride (1 mg/10 g) and xylazine (0.1 mg/10 g) and perfused intracardially with PBS in accordance with protocols approved by the University of Pennsylvania.

Brain samples were homogenized in 10 mM ammonium acetate, pH 5.7 (1:2; w/v) using a handheld sonic homogenizer. Compound from 50 µL of brain homogenate or plasma was extracted with 200 µL acetonitrile, centrifuged, and the supernatant removed for LC/MS/MS analysis. Compounds were detected using multiple reaction monitoring (MRM) of their specific collision-induced ion transitions and quantified using peak areas.

The LC/MS/MS system was comprised of an Aquity UPLC, a TQ MS, and controlled using MassLynx software (Waters Corporation, Milford, Mass., USA). Samples were separated on an Aquity BEH C18 column (1.7 µm, 2.1×50 mm) at 35° C. For operation in positive electrospray ionization mode, the mobile phase A was 0.1% (v/v) formic acid, and B was either acetonitrile or methanol with 0.1% (v/v) formic acid. For operation in negative electrospray ionization mode, the mobile phase A was 10 mM ammonium acetate, and B was methanol with 10 mM ammonium acetate. Injections of 5 µL were separated at a flow rate of 0.6 mL/min using a gradient from 5% to 95% B over two minutes followed by wash and re-equilibration steps.

The MS was operated with a desolvation temperature of 450° C. and a source temperature of 150° C. Desolvation and source nitrogen gas flows were 900 L/hr and 50 L/hr, respectively. Collision cell argon gas flow was 0.1 mL/min. Source and analyzer voltages were optimized for each compound using the MassLynx auto tune utility. Compound standards at 1000 ng/mL in 50% acetonitrile were infused at 30 µL/min and combined with flow from the UPLC at 0.6 mL/min and 50% B.

Standard curves were generated from spiked brain homogenate and plasma prepared at 4, 40, 400 and 4000 ng/mL and extracted as above. Peak area was plotted versus concentration and a 1/x weighted linear regression curve was used to quantify the unknowns using the average peak area from triplicate injections.

Data Analysis

Equilibrium dissociation constants ($K_d$), $IC_{50}$, and Schild regression analyses was performed with GraphPad Prism software (GraphPad Software Inc., La Jolla, Calif., USA).

Example 1

TP Receptor Antagonists

TP receptor antagonists have been sought by the pharmaceutical industry because TxA2 plays a role in platelet aggregation and lung inflammation (Narumiya et al., 2001, J Clin Invest 108:25-30; Chaer, et al., 2006, Vasc Endovascular Surg. 40:261-267; Hata et al., 2004, Pharmacol Ther. 103:147-166). There are two splice isoforms of the human TP receptor (Raychowdhury, et al., 1994, J Biol Chem. 269:19256-19261), but there is no evidence of pharmacological differences between these two variants. A number of compounds have been identified that effectively antagonize the TP receptor and certain of these are being pursued clinically (Dogne, et al., 2006, Curr Pharm Des. 12:903-923). However, with few exceptions, existing TP antagonists (FIG. 1) contain a carboxylic acid moiety that greatly limits their ability to passively diffuse across the blood-brain barrier (BBB) and gain access to the brain, as carboxylate-containing molecules typically have poor brain exposure unless they are actively transported (Austin, et al., 1995, J Pharm Sci. 84:1180-1183; Pajouhesh et al., 2008, NeuroRx 2:541-553).

The following experiments were designed to analyze TP receptor antagonists to determine their relative BBB penetration. The TP receptor antagonists were administered via i.p. injection at 5 mg/kg to normal mice, and brain and plasma compound concentrations were assessed by LC-MS/MS at 1 and 4 hours after dosing. All of the existing TP antagonists had very low brain concentrations that amounted to 1-5% of that found in plasma (Table 1).

33:175-181; Kalvass et al., 2007, Drug Metab Dispos. 35:660-666; Friden, et al., 2007, Drug Metab Dispos. 35:1711-1719). As summarized in Table 1, the $f_{u(plasma)}/f_{u(brain)}$ values for these compounds were significantly greater than their corresponding B/P ratios, indicating that the compounds were not freely diffusible across the BBB. This is further illustrated by comparing the calculated $B/P_{free}$ ratios (Table 1), which are <<1. Because the existing repertoire of TP receptor antagonists share common structural features, including free carboxylate moieties, it is highly unlikely that any of these existing compounds would be sufficiently brain-penetrant to be potential AD therapeutics.

The relative BBB-impermeability of S-18886 (Table 1) led to investigations as to why this compound reduced Aβ levels in Tg2576 mice (Shineman, et al., 2008, J. Neurosci 28:4785-4794). Brain and plasma drug levels of S-18886 were measured after administration to mice in drinking water, as previously described (Shineman, et al., 2008, J. Neurosci 28:4785-4794). Mice have 20-30 separate drinking bouts over the course of the day (Gannon, et al., 1992, Physiol Behav. 51:515-521), albeit with much greater water consumption during the night. When brain and plasma levels of S-18886 were measured during the daylight phase, the calculated free drug concentrations in brain (Table 2) were ~30% of the $K_d$ value for S-18886 (0.36 nM) at the mouse TP receptor. Drug concentrations should be appreciably higher during the night due to greater water consumption (Gannon, et al., 1992, Physiol Behav. 51:515-521; Johnson et al., 1990, Am J Physiol. 259:R1035-R1042), and it thus appears that

TABLE 1

Brain and Plasma Levels of TP Receptor Antagonists

| Comp | Time (h) | Plasma (ng/ml) | Brain (ng/ml) | B/P | $f_{u(plasma)}$ | $f_{u(brain)}$ | $f_{u(pl)}/f_{u(br)}$ | $B/P_{free}$ |
|---|---|---|---|---|---|---|---|---|
| S-18886 | 1 | 1713 ± −170 | 42.4 ± 6.2 | 0.02 | 0.026 ± 0.001 | 0.044 ± 0.002 | 0.59 | 0.04 |
|  | 4 | 190 ± 74 | 9.0 ± 5.2 | 0.05 |  |  |  | 0.08 |
| Daltroban | 1 | 6450 ± 1090 | 133 ± 8.6 | 0.02 | 0.114 ± 0/016 | 0.221 ± 0.053 | 0.52 | 0.04 |
|  | 4 | 1793 ± 345 | 55.9 ± 16.0 | 0.03 |  |  |  | 0.06 |
| BM567 | 1 | 3600 ± 923 | 40.2 ± 12.3 | 0.01 | 0.004 ± 0.001 | 0.020 ± 0.001 | 0.20 | 0.06 |
|  | 4 | 2248 ± 1400 | 18.5 ± 7.8 | 0.01 |  |  |  | 0.04 |

B/P = brain-to-plasma ratio; $f_u$ = fraction unbound; $B/P_{free}$ = unbound drug brain-to-plasma ratio Very low brain-to-plasma (B/P) drug levels such as these typically suggest a lack of BBB permeability, and in fact CNS drugs that are thought to diffuse freely across the BBB have been shown to have B/P ratios of 0.42-24 (Maurer, et al., 2005, Drug Metab Dispos. 33:175-181). Without wishing to be bound by any particular theory, it is believed that it is possible (although uncommon) for a BBB-permeable compound to have a very low B/P ratio if the fraction of free, unbound drug is much greater in the brain than in the plasma. More specifically, a drug that is freely diffusible across the BBB will at equilibrium have a free drug B/P ratio ($B/P_{free}$)=1, where $B/P_{free}=B/P \times f_{u(brain)}/f_{u(plasma)}$ (Maurer, et al., 2005, Drug Metab Dispos. 33:175-181; Kalvass et al., 2007, Drug Metab Dispos. 35:660-666) and $f_u$ represents unbound drug fractions. A rearrangement of this equation reveals that a freely BBB-permeable drug will have $B/P=f_{u(plasma)}/f_{u(brain)}$. To ensure that the low B/P ratios obtained with the TP antagonists of Table 1 were truly reflective of poor BBB permeability, the unbound fractions in plasma and brain homogenates were measured using established equilibrium dialysis methods (Maurer, et al., 2005, Drug Metab Dispos.

free S-18886 brain levels in the Tg2576 studies should have resulted in appreciable inhibition of TP receptors during the dark phase and partial inhibition during the light phase. However, free S-18886 in plasma is >10× that in the brain and the much greater TP receptor inhibition in the periphery greatly increases the chances of both on-target and off-target side-effects. In fact, extended exposure to excessively high blood levels of a TP receptor antagonist could increase the risk of bleeding complications due to compromise of platelet function, as it is known that TP receptor knockout mice and TxA2 synthase-deficient mice have prolonged clotting times (Thomas, et al., 1998, J Clin Invest 102:1994-2001; Yu, et al., 2004, Blood 104:135-142). Furthermore, inactivating mutations in the TP receptor have been linked to a dominantly inherited bleeding disorder in humans (Hirata, et al., 1994, J Clin Invest 94:1662-1667). Given the elderly and often frail status of AD patients, keeping peripheral TP antagonist levels as low as possible while maintaining effective brain concentrations would provide greater safety, and there is thus a need for novel TP receptor antagonists with greatly improved brain penetration to serve as potential AD therapeutics.

TABLE 2

Free S-18886 Brain Levels after Dosing by Water.

| Days | Brain (nM) |
|---|---|
| 1 | 0.093 ± 0.019 |
| 2 | 0.117 ± 0.080 |

The carboxylic acid moiety found in the vast majority of the known TP receptor antagonists has been suggested to interact with a conserved arginine residue within the receptor (Breyer, et al., 2001, Annu Rev Pharmacol Toxicol. 41:661-690; Funk, et al., 1993, Mol Pharmacol. 44:934-939). However, a carboxylic acid moiety may not be strictly required for activity, as antagonists in which the carboxylate is replaced with more lipophilic surrogates (Ducharme, et al., 2005, Bioorg Med Chem Lett. 15:1155-1160; Hall, et al., 2007, Bioorg Med Chem Lett. 17:1200-1205) have been reported for other prostanoid receptors with a similar conserved arginine residue (Breyer, et al., 2001, Annu Rev Pharmacol Toxicol. 41:661-690; Chang, et al., 1997, Biochem J. 322:597-601). Additionally, certain of these compounds have been shown to have good brain exposure (Hall, et al., 2007, Bioorg Med Chem Lett. 17:1200-1205). To evaluate whether brain-penetrant TP receptor antagonists could also be developed, experiments were designed to investigate whether known TP receptor antagonists, such as S-18886 and related tetrahydronaphtalenes (THNPs), could be modified by isosteric replacement or pro-drug approaches to generate derivatives with improved brain penetration.

To facilitate the characterization of the new compounds, cell-based TP receptor functional assays were optimized. HEK293 clones have been produced that stably express the human (hTP) or mouse (mTP) TP receptor ($\alpha$ isoform), and treatment of these clones with I-BOP ([1S-[1$\alpha$,2$\alpha$(Z),3$\beta$(1E,3S*),4$\alpha$]]-7-[3-[3-hydroxy-4-(4-iodophenoxy)-1-butenyl]-7-oxabicyclo[2.2.1]hept-2-yl]-5-heptenoic acid) results in increased production of inositol triphosphate (IP3) (Knezevic, et al., 1993, Blood 82:A156; Shenker, et al., 1991, J Biol Chem 266:9309-9313; Huang, et al., 2004, Cell Signal 16:521-533) which can be quantified by measuring the breakdown product, inositol monophosphates (IP1), using a commercial time-resolved fluorescence assay. This IBOP-mediated increase of IP1 can be fully inhibited with TP receptor antagonists. A radioligand binding assay was also developed to allow for the determination of binding affinities of compounds at the hTP and mTP receptors.

Figure 2:
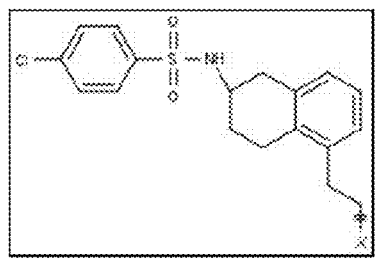
FIG. 2 is a table illustrating radioligand binding data for tetrahydronaphtalene (THNP) TP antagonists on human and mouse TP receptors. Data are represented as the average and standard deviation of at least three independent experiments.
Figure 3:
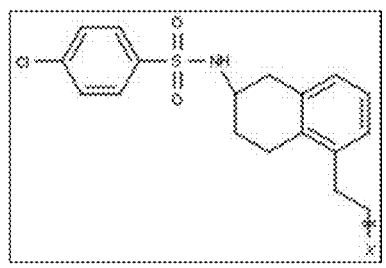
FIG. 3 is a table illustrating results from a functional IP1 assay for analyzing THNP TP antagonists on human and mouse TP receptors. Data are represented as the average and standard deviation of at least three independent experiments.

Compounds were tested for interaction with human and mouse TP receptors in the radioligand binding assay (FIG. 2). In general, compounds had a 5- to 10-fold lower $K_d$ for mouse TP receptors than human TP receptors. Substitution of the carboxylic acid resulted in a decrease in affinity for the TP receptor, although many compounds retained high affinity for the TP receptor. The most tolerable substitutions were the tetrazole (CNDR-51279) and trifluoroethyl amide (51418) substitutions. Propyl alcohol and trifluoromethyl alcohol substituted THNP examples were also synthesized (CNDR-51281 and CNDR-51354, respectively) that in radioligand binding analyses showed 200-300 nM and 20-50 nM affinities for the hTP and mTP receptors, respectively. Compounds were tested for antagonist activity against human and mouse TP receptors using the IP1 functional HTRF assay (FIG. 3). All compounds retained antagonist activity and displayed a similar 5- to 10-fold lower $IC_{50}$ on mouse receptors.

Figure 4:
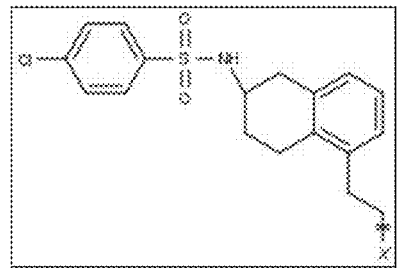
FIG. 4 is a table illustrating brain and plasma levels of compounds as determined by LCMS 1 hour after a 5 mg/kg IP injection into mice. Data are represented as the average and standard deviation of at least three independent mouse injections.

To examine the blood-brain barrier permeability of these compounds, one-month old B6C3F1 mice were injected at 5 mg/kg and sacrificed 1 hour after injection. LC/MS-MS analysis of brain and plasma drug levels revealed that replacement of the carboxylic acid moiety with a trifluoromethyl alcohol (51354), hydroxyl (51281), and dioxolane (51414) greatly increased brain levels of the drug (FIG. 4). In contrast, CNDR-51279 showed very little brain penetration, presumably because the tetrazole still carries a negative charge at physiological pH which impedes BBB permeability.

A number of general observations were made from the results presented herein: 1) The carboxylic acid example (CNDR-51280) was a potent antagonist with high affinity for the hTP and mTP receptors; 2) replacement of the carboxylate with a tetrazole is well tolerated (CNDR-51279); 3) Most compounds showed slightly higher affinity for the mTP receptor than hTP receptor; 4) Ester or amide derivative of CNDR-51280 resulted in compounds that still retained reasonable receptor binding. 5) Certain isosteric replacements, as exemplified by CNDR-51354, CNDR-51281 and CNDR-51414, resulted in brain-penetrant compounds.

Example 2

Synthetic Chemistry

All solvents used for chemically modify existing TP receptor antagonists were reagent grade. All reagents were purchased from Aldrich or Acros and used as received. Thin layer chromatography (TLC) was performed with 0.25 mm E. Merck pre-coated silica gel plates. Unless otherwise stated, flash chromatography was performed with silica gel 60 (particle size 0.040-0.062 mm) supplied by Silicycle and Sorbent Technologies. TLC spots were detected by viewing under a UV light. Infrared (IR) spectra were recorded on a Jasco Model FT/1R-480 Plus spectrometer. Proton ($^1$H) and carbon ($^{13}$C) NMR spectra were recorded on a Bruker AMX-500 spectrometer. Chemical shifts were reported relative to solvents. High-resolution mass spectra were measured at the University of Pennsylvania Mass Spectrometry Center on either a VG Micromass 70/70H or VG ZAB-E spectrometer. Analytical reverse-phased (Sunfire™ C18; 4.6×50 mm, 5 mL) high-performance liquid chromatography (HPLC) was performed with a Waters binary gradient module 2525 equipped with Waters 2996 PDA and Waters micromass ZQ. Optical rotations were measured on a Jasco P-2000 polarimeter. All samples were analyzed employing a linear gradient from 10% to 90% of acetonitrile in water over 8 minutes and flow rate of 1 mL/min (method A) or over 7 minutes and flow rate of 2 mL/min (method B). Preparative reverse phase HPLC purifications were performed on a Gilson instrument (i.e., Gilson 333 pumps, a 215 liquid handler, 845Z injection module, and PDA detector) employing Waters SunFire™ preparative $C_{18}$ OBD™ columns (5 µm 19×50 or 19×100 mm). Purifications were carried out employing a linear gradient from 10% to 90% of acetonitrile in water for 15 minutes with a flow rate of 20 mL/min.

Example 3

Prodrugs

Ester and amide examples can serve as pro-drugs to release the potent carboxylic acid TP receptor antagonist CNDR-51280. Compounds in were administered at 5 mg/kg to female mice, and levels of the compound and the carboxylic acid hydrolysis product (CNDR-51280) were evaluated by LC-MS/MS 1 h after injection (Table 3).

TABLE 3

| Compound | X | Plasma (nM) | XCOOH Plasma (nM) |
|---|---|---|---|
| 51280 | carboxylic acid (C(=O)OH on isopropenyl) | 10376 (+/−3480) | NA |
| 51278 | ethyl ester | <LOD | 174 (+/−6.9) |
| 51455 | isopropyl ester | 3.8 (+/−6.7) | 4254 (+/−1587) |
| 51326 | isopropyl amide | 103 (+/−43) | 58 (+/−19) |
| 51418 | CH₂CF₃ amide | 109 (+/−45) | 100 (+/−43) |

Example 4

Synthetic Protocols

5-Bromo-3,4-dihydronaphthalen-2(1H)-one, designated as 2 in FIG. 5, was prepared as follows (see e.g., Aroop, C.; Viswanathan, R.; Johnston, J. N. *Org. Lett.* 2007, 9, 5027). Oxalyl chloride (2.2 mL, 25.13 mmol) was added to a solution of 3-(2-bromophenyl)propanoic acid (2.86 g, 12.49 mmol) in dichloromethane (25 mL) at 0° C. After 30 min, the reaction was warmed to room temperature and stirring continued for 3 hr. The solvent was removed under reduced pressure and replaced with diethyl ether (25 mL). This solution was cooled to −40° C. and freshly prepared diazomethane (~45 mmol) in diethyl ether (90 mL) was added dropwise over 1 hr. The reaction was warmed to room temperature over 1 hour and stirred at room temperature for a further 1 hour. The solvent was removed under a positive pressure of argon and the resultant yellow solid was purified by flash chromatography on silica gel (20% ethyl acetate in hexanes). The purified product was dissolved in dichloromethane (90 mL) and added dropwise, over 40 min, to a suspension of rhodium(II) acetate dimer (19.4 mg, 0.09 mmol) in dichloromethane (800 mL) at reflux. After heating at reflux for a further 45 min, the reaction mixture was cooled to room temperature and washed with saturated sodium bicarbonate solution. The organic layer was separated, dried over sodium sulfate and concentrated to ~100 mL. Trifluoroacetic acid (1.2 mL, 15.6 mmol) was added and the reaction stirred at room temperature for 1 hour 45 min before being quenched with saturated sodium bicarbonate solution. The organic layer was separated, dried over sodium sulfate and concentrated to dryness. Silica gel chromatography (20% ethyl acetate in hexanes) gave the purified product as a yellow solid (1.54 g). Yield: 55%.

$^1$H NMR (CDCl$_3$): δ 2.55 (t, J=7.0 Hz, 2H), 3.23 (t, J=7.0 Hz, 2H), 3.59 (s, 2H), 7.06-7.09 (m, 2H), 7.46-7.48 (m, 1H) ppm. $^{13}$C NMR (CDCl$_3$): δ 28.3, 37.8, 45.1, 123.9, 127.7, 128.3, 131.2, 135.7, 136.4, 209.8 ppm.

(E)-Ethyl-3-(6-oxo-5,6,7,8-tetrahydronaphthalen-1-yl)acrylate, designated as 3 in FIG. 5, was prepared as follows. A solution of 5-bromo-3,4-dihydronaphthalen-2(1H)-one (476.9 mg, 2.12 mmol), ethyl acrylate (0.28 mL, 2.58 mmol), palladium(II) acetate (4.8 mg, 0.02 mmol) and tri-o-tolylphosphine (33.1 mg, 0.11 mmol) in triethylamine (2 mL) was heated at 100° C. in a sealed tube for 4 hour. The reaction mixture was cooled to room temperature, diluted with dichloromethane (15 mL) and washed with hydrochloric acid (1 M, 10 mL). The organic layer was separated and the aqueous layer extracted with dichloromethane. The combined organic layers were dried over sodium sulfate and concentrated to dryness. Silica gel chromatography (20% ethyl acetate in hexanes), gave the purified product as yellow oil (385.6 mg). Yield: 74%.

$^1$H NMR (CDCl$_3$): δ 1.33 (t, J=7.0 Hz, 3H), 2.52 (t, J=6.5 Hz, 2H), 3.18 (t, J=6.5 Hz, 2H), 3.58 (s, 2H), 4.26 (q, J=7.0 Hz, 2H), 6.35 (d, J=16.0 Hz, 1H) 7.13 (d, J=7.5 Hz, 1H), 7.22 (t, J=8.0 Hz, 1H), 7.46 (d, J=7.5 Hz, 1H), 8.02 (d, J=15.5 Hz, 1H) ppm.

(E)-ethyl 3-(6-(benzylamino)-5,6,7,8-tetrahydronaphthalen-1-yl)acrylate, designated as 4 in FIG. 5, was prepared as follows. A solution of (E)-ethyl-3-(6-oxo-5,6,7,8-tetrahydronaphthalen-1-yl)acrylate (77 mg, 0.31 mmol) in dichloroethane (1.1 mL) was added with a solution of benzylamine (35 μL, 0.31 mmol) in dichloroethane (75 μL) followed by a second addition of acetic acid (71 μL, 1.3 mmol). The resulting mixture was stirred at room temperature for 45 min prior to an addition of sodium triacetoxyborohydride (375 mg, 1.7 mmol). The reaction mixture was allowed to stir at room temperature for 16 hour and then it was quenched by addition of saturated aqueous solution of sodium bicarbonate (2 mL). The pH was then adjusted to pH 8 by addition of sodium hydroxide (1 M solution in water) and the resulting mixture was extracted with dichloromethane; the organic layer dried over sodium sulfate and concentrated to dryness. The residue so obtained was finally purified by silica gel column chromatography (eluent: 10% methanol in dichloromethane) obtaining the title compound (93 mg, 0.28 mmol). Yield: 83%.

HPLC-MS retention time: 4.1 min (Method A). $^1$H NMR (CDCl$_3$): δ 1.34 (t, J=7.0 Hz, 3H), 1.84-1.88 (m, 1H), 2.24-2.33 (m, 1H), 2.75-2.81 (m, 1H), 2.93-2.99, (m, 1H), 3.05-3.15 (m, 3H), 4.05 (broad s, 2H), 4.27 (q, J=7.0 Hz, 2H), 6.32 (d, J=15.5 Hz, 2H), 7.10-7.17 (m, 2H), 7.29-7.45 (m, 6H), 7.92 (d, J=15.5 Hz, 1H) ppm. MS (ESI$^+$): calculated for C$_{22}$H$_{26}$NO$_2^+$ 336.2. found 336.3.

Ethyl-3-(6-(4-chlorophenylsulfonamido)-5,6,7,8-tetrahydronaphthalen-1-yl)propanoate, designated as 5 in FIG. 5, was prepared as follows. A solution of (E)-ethyl 3-(6-(benzylamino)-5,6,7,8-tetrahydronaphthalen-1-yl)acrylate (120 mg, 0.36 mmol) in ethyl alcohol (10 mL) was added with hydrochloric acid (1.0 eq., 1 N solution in water) followed by Pd on C (10 wt. %; 50% wet). The resulting mixture was stirred under 1 atm of hydrogen for 48 hour at 55° C. The reaction mixture was then filtered through a celite pad and after evaporation of the volatiles, the desired amine (100 mg, 0.35 mmol) was obtained as hydrochloride salt, which was re-dissolved in anhydrous dichloromehane (4 mL) and added at 5° C. with 4-chlorophenyl sulphonylchloride (75 mg, 0.35 mmol) followed by triethylamine (112 µL, 0.7 mmol). The resulting mixture was stirred for 3 hour allowing the temperature to rise to room temperature. The organic layer was then diluted with dichloromethane and extracted with water. The organic layer was then dried over sodium sulfate and concentrated to dryness. The residue so obtained was finally purified by column chromatography (Silica gel; eluent: 30% ethyl actetate in hexanes) obtaining the title compound (85 mg, 0.20 mmol). Yield: 56%.

HPLC-MS retention time: 8.1 min (Method A). $^1$H NMR (CDCl$_3$): δ 1.26 (t, J=7.0 Hz, 3H), 1.77 (m, 1H), 1.96-2.0 (m, 1H), 2.53-2.56 (m, 2H), 2.62-2.71 (m, 2H) 2.71-2.87 (m, 3H), 2.94 (dd, J=16.0/5.0 Hz, 1H), 3.63 (m, 1H) 4.14 (q, J=7.0 Hz, 2H), 5.04 (d, J=7.5 Hz, 1H), 6.83 (d, J=7.5 Hz, 1H), 7.00 (d, J=7.0 Hz, 1H), 7.06 (t, J=7.5 Hz, 1H), 7.49 (d, J=9.0 Hz, 2H), 7.83 (d, J=9.0 Hz, 2H) ppm. $^{13}$C NMR (CDCl$_3$): δ 14.4, 24.0, 27.8, 29.6, 34.5, 37.1, 49.3, 60.7, 126.3, 126.8, 128.0, 128.6, 129.6, 133.2, 133.7, 138.8, 139.2, 139.7, 173.1. MS (ESI$^+$): calculated for C$_{21}$H$_{25}$ClNO$_4$S$^+$ 422.1. found 422.1.

Figure 7:
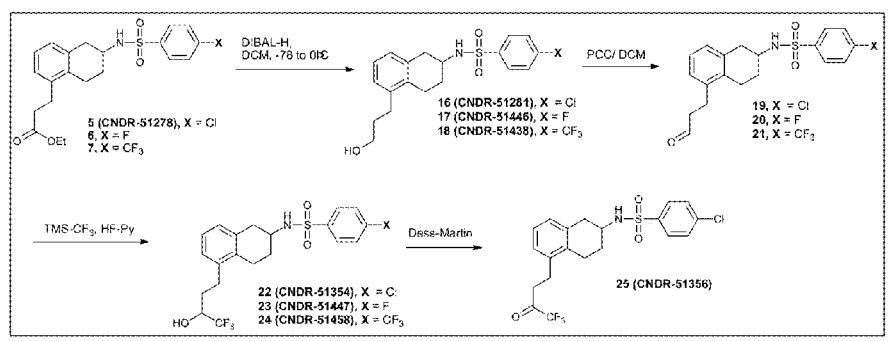
FIG. 7 is a schematic representation of a synthetic route to generate compounds of the invention.

Ethyl 3-(6-(4-fluorophenylsulfonamido)-5,6,7,8-tetrahydronaphthalen-1-yl)propanoate, designated as 6 in FIG. 7, was prepared using the same procedure employed for 5 with starting materials 4 and 4-fluorobenzenesulfonyl chloride. Yield: 59%.

HPLC-MS retention time: 6.4 min (Method B). $^1$H NMR (CDCl$_3$): δ 1.26 (t, J=7.1 Hz, 3H), 1.76-1.80 (m, 1H), 1.98-2.00 (m, 1H), 2.53 (t, J=7.7 Hz, 2H), 2.64 (dd, J=16.2 and 7.9 Hz, 1H), 2.69-2.74 (m, 1H), 2.79-2.88 (m, 3H), 2.95 (dd, J=16.1 and 4.65 Hz, 1H), 3.63-3.69 (m, 1H), 4.14 (q, J=7.13 Hz, 2H), 4.81 (d, J=7.6 Hz, 1H), 6.84 (d, J=7.4 Hz, 1H), 7.01 (d, J=7.0 Hz, 1H), 7.06 (t, J=7.5 Hz, 1H), 7.18-7.21 (m, 2H), 7.90-7.93 ppm (m, 2H). $^{13}$C NMR (CDCl$_3$): δ 14.4, 24.0, 27.8, 29.7, 34.5, 37.2, 49.3, 60.7, 116.6 (d, J$_{CF}^2$=19.1 Hz), 126.4, 126.9, 128.1, 129.9 (d, J$_{CF}^3$=9.1 Hz), 133.2, 133.7, 137.4, 138.9, 166.1 (d, J$_{CF}^2$=257.2 Hz), 173.1 ppm. IR: ν 3275, 1729 cm$^{-1}$. MS (ESI+): calculated for C$_{21}$H$_{25}$FNO$_4$S$^+$ 406.15. found 406.01.

Ethyl 3-(6-(4-(trifluoromethyl)phenylsulfonamido)-5,6,7,8-tetrahydronaphthalen-1-yl)propanoate, designated as 7 in FIG. 7, was prepared using the same procedure employed for 5 with starting materials 4 and 4-trifluoromethylbenzenesulfonyl chloride. Yield: 39%.

HPLC-MS retention time: 6.9 min (Method B). $^1$H NMR (CDCl$_3$): δ 1.26 (t, J=7.1 Hz, 3H), 1.81-1.77 (m, 1H), 2.03-2.00 (m, 1H), 2.55 (t, J=7.9 Hz, 2H), 2.70 (m, 2H), 2.84 (m, 3H), 2.96 (dd, J=16.2, 4.0 Hz, 1H), 3.69 (m, 1H), 4.14 (q, J=7.1 Hz, 2H), 6.82 (d, J=7.4 Hz, 1H), 5.21 (s, 1H), 7.03 (dt, J=20.1, 9.2 Hz, 2H), 7.78 (d, J=8.1 Hz, 2H), 8.03 (d, J=8.1 Hz, 2H) ppm. $^{13}$C NMR (CDCl$_3$): 14.4, 24.0, 27.8, 29.7, 34.5, 37.1, 49.5, 60.7, 122.4, 124.5, 126.4, 126.4, 126.5, 126.5, 126.9, 127.6, 128.0, 133.1, 133.6, 133.6, 138.8, 144.9, 173.1 ppm. MS (ESI+): calculated for C$_{22}$H$_{25}$F$_3$NO$_4$S$^+$ 456.15. found 456.13

3-(6-(4-Chlorophenylsulfonamido)-5,6,7,8-tetrahydronaphthalen-1-yl)propanoic acid, designated as 6 in FIG. 5, was prepared as follows. A solution of ethyl 3-(6-(4-chlorophenylsulfonamido)-5,6,7,8-tetrahydronaphthalen-1-yl)propanoate (23 mg, 0.05 mmol) in a mixture containing methanol (1 mL) and water (1 mL) was added with sodium hydroxide (220 µL of a 1 M solution in water, 0.22 mmol). The resulting mixture was then stirred at 55° C. for 1.5 hour. The pH of the reaction mixture was then adjusted to pH 5.5 by addition of a 1 N aqueous solution of hydrochloric acid and the resulting mixture was extracted with ethyl acetate. The organic layer was then dried over sodium sulfate and concentrated to dryness obtaining the title compound (19 mg). Yield: 91%.

HPLC-MS retention time: 6.6 min (Method A). $^1$H NMR (CD$_3$OD): δ 1.68-1.72 (m, 1H), 1.93-1.96 (m, 1H), 2.50-2.53 (m, 2H), 2.61-2.68 (m, 2H), 2.81-2.86 (m, 4H), 3.46-3.51 (m, 1H), 6.73 (d, J=6.5 Hz, 1H), 6.96-7.00 (m, 2H), 7.57 (d, J=9.0 Hz, 2H), 7.87 (d, J=9.0 Hz, 2H) ppm. $^{13}$C NMR (CD$_3$OD): 25.6, 28.9, 31.1, 35.3, 38.0, 50.9, 127.1, 127.5, 128.7, 129.7, 130.5, 134.5, 135.6, 139.8, 139.9, 142.2, 176.9 ppm. MS (ESI$^+$): calculated for C$_{19}$H$_{21}$ClNO$_4$S$^+$ 394.1. found 394.3.

Figure 5:
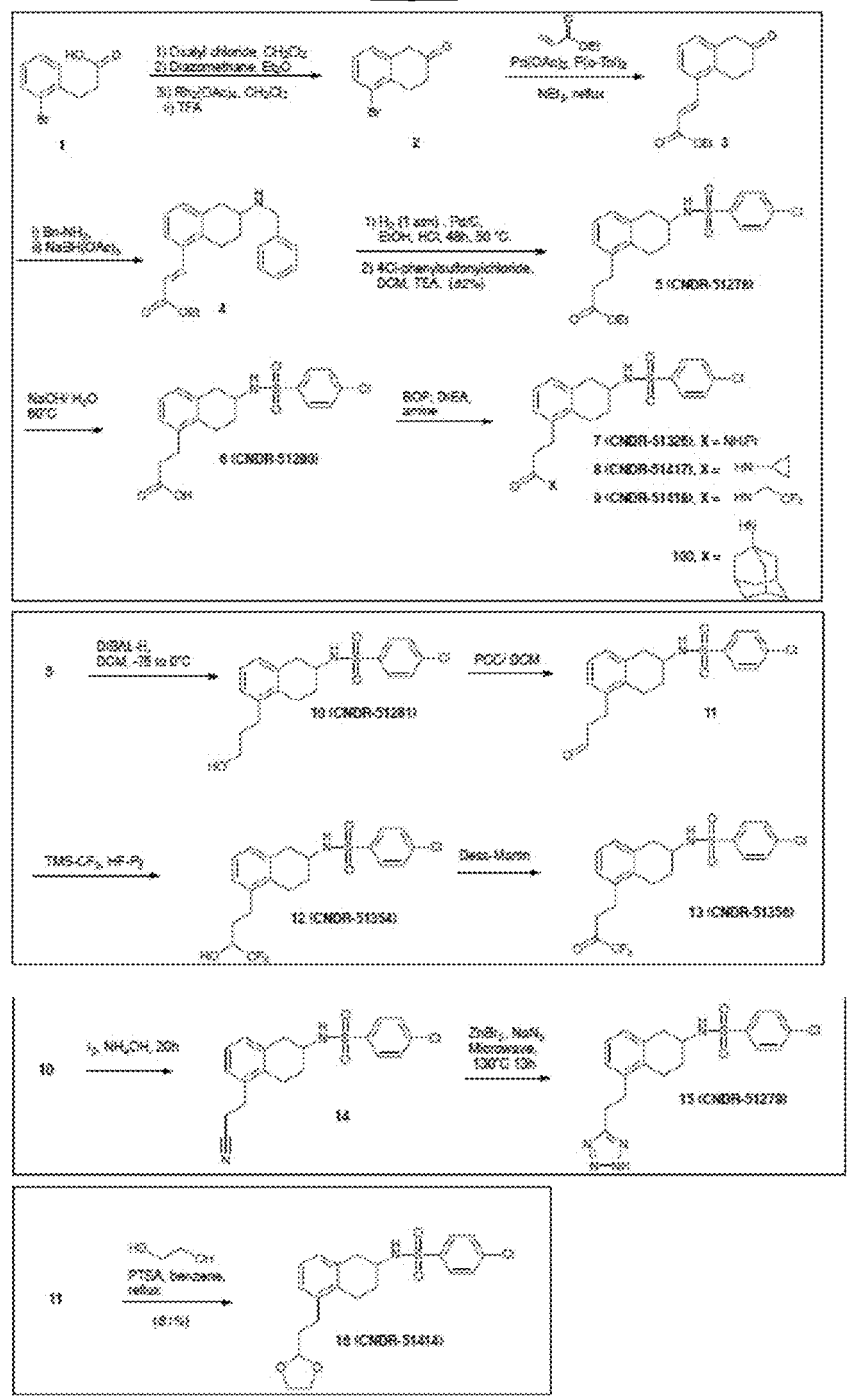
FIG. 5 is a schematic representation of a synthetic route to generate compounds of the invention.

3-(6-(4-Fluorophenylsulfonamido)-5,6,7,8-tetrahydronaphthalen-1-yl)propanoic acid was prepared using the same procedure employed for 6 of FIG. 5, using as starting material 6 of FIG. 7. Yield: 81% after preparative reverse phase HPLC purification.

$^1$H NMR (CD$_3$OD): δ 1.65-1.73 (m, 1H), 1.92-1.95 (m, 1H), 2.50 (t, J=7.8 Hz, 2H), 2.61-2.67 (m, 2H), 2.80-2.85 (m, 4H), 3.46-3.49 (m, 1H), 6.78 (d, J=6.8 Hz, 1H), 6.94-6.99 (m, 2H), 7.28 (t, J=8.6 Hz, 2H), 7.92-7.95 (m, 2H) ppm. $^{13}$C NMR (CD$_3$OD): δ 25.6, 28.9, 31.1, 35.4, 38.1, 50.9, 117.2, 117.4, 127.1, 127.6, 128.7, 130.9, 131.0, 134.5, 135.7, 139.7, 139.7, 140.0, 166.4 (d, J$_{CF}^1$=250.7 Hz), 176.9 ppm. IR: ν 3216 (acid band), 1702 cm$^{-1}$. MS (ESI$^+$): calculated for C$_{19}$H$_{21}$FNO$_4$S$^+$ 378.12. found 378.04.

3-(6-(4-(Trifluoromethyl)phenylsulfonamido)-5,6,7,8-tetrahydronaphthalen-1-yl)propanoic acid was prepared using the same procedure employed for 6 from FIG. 5, using as starting material 7 of FIG. 7. Yield: 84% after preparative reverse phase HPLC purification.

HPLC-MS retention time: 4.1 min (Method B). $^1$H NMR (CD$_3$OD): δ 1.72 (m, 1H), 1.97-1.94 (m, 1H), 2.51 (t, J=7.8 Hz, 2H), 2.71-2.63 (m, 2H), 2.84 (m, 4H), 3.58-3.53 (m, 1H), 6.78-6.76 (m, 1H), 6.97 (m, 2H), 7.88 (d, J=8.3 Hz, 2H), 8.08 (d, J=8.2 Hz, 2H) ppm. IR: ν 3272 (acid band), 2923, 1696 cm$^{-1}$. HRMS (ESI$^+$): calculated for C$_{20}$H$_{20}$F$_3$NO$_4$SNa$^+$ 450.0963. found 450.0970.

3-(6-(4-Chlorophenylsulfonamido)-5,6,7,8-tetrahydronaphthalen-1-yl)-N-isopropylpropanamide, designated as 7 in FIG. 5, was prepared as follows. A solution of 3-(6-(4-chlorophenylsulfonamido)-5,6,7,8-tetrahydronaphthalen-1-yl)propanoic acid (11.4 mg, 0.03 mmol) in anhydrous dimethylsulfoxide (1 mL), was added with (benzotriazol-1-yloxy)tris(dimethylamino)phosphonium hexafluorophosphate (19 mg, 0.043 mmol), isopropylamine (5 µL, 0.06 mmol), and diisopropylethylamine (7.6 mL, 0.045 mmol) and the resulting mixture was allowed to stir at room temperature for 16 hour. The reaction mixture was then diluted with ethyl acetate (8 mL) and extracted with water. The organic layer was then dried over sodium sulfate and concentrated to dryness. The residue so obtained was purified by column chromatography (silica gel; Biotage SP4; gradient from 1% to 10% of methanol in dichloromethane) obtaining the title compound (12.1 mg, 0.028 mmol). Yield: 96%.

HPLC-MS retention time: 7.4 min (Method A). $^1$H NMR (CDCl$_3$): δ 1.11 (d, J=6.5 Hz, 6H), 1.74-1.81 (m, 1H), 1.95-1.97 (m, 1H), 2.36 (t, J=8 Hz, 2H), 2.62-2.66 (m, 1H), 2.69-2.75 (m, 1H), 2.81-2.90 (m, 3H), 2.94-2.99 (m, 1H), 3.66 (m, 1H), 4.07 (m, 1H), 4.84 (bd, J=7.5 Hz, 1H), 5.30 (bs, 1H), 6.83 (d, J=7.5 Hz, 1H), 7.00 (d, J=7.5 Hz, 1H), 7.04 (m, 1H), 7.49 (d, J=8.0 Hz, 2H), 7.83 (d, J=8.0 Hz, 2H) ppm. $^{13}$C NMR (CDCl$_3$): δ 22.8, 23.7, 28.4, 29.5, 37.0, 37.1, 41.7, 49.2, 126.3, 127.0, 128.0, 128.6, 129.6, 133.1, 133.6, 139.1, 139.2, 139.8, 171.5 ppm. MS (ESI+: calculated for $C_{22}H_{28}ClN_2O_3S^+$ 435.1. found 435.0.

3-(6-(4-Chlorophenylsulfonamido)-5,6,7,8-tetrahydronaphthalen-1-yl)-N-cyclopropylpropan-amide, designated as 8 in FIG. 5, was prepared using the same procedure employed for 7, using as starting materials 6 and cyclopropylamine. Yield: 91%.

HPLC-MS retention time: 5.3 min (Method B). $^1$H NMR (CDCl$_3$): δ 0.42-0.45 (m, 2H), 0.76-0.79 (m, 2H), 1.72-1.79 (m, 1H), 1.93-1.96 (m, 1H), 2.34 (t, J=8.0 Hz, 2H), 2.62-2.73 (m, 3H), 2.73-2.96 (m, 4H), 3.63-3.66 (m, 1H), 5.10, (d, J=7.6 Hz, 1H), 5.65 (bs, 1H), 6.81 (d, J=7.4 Hz, 1H), 6.97 (d, J=7.5 Hz, 1H), 7.02-7.05 (m, 1H), 7.48 (d, J=9.0 Hz, 2H), 7.46 (d, J=9.0 Hz, 2H) ppm. $^{13}$C NMR (CDCl$_3$): δ 6.7, 22.8, 23.7, 28.3, 29.5, 36.7, 37.0, 49.2, 126.3, 127.0, 128.0, 128.5, 129.6, 133.1, 133.6, 139.2, 139.2, 139.7, 173.6 ppm. IR: ν 3370, 3279, 3089, 2931, 1649, 1537 cm$^{-1}$. HRMS (ESI+): calculated for $C_{22}H_{25}ClN_2O_3S$ 433.1353. found 433.1360.

3-(6-(4-Chlorophenylsulfonamido)-5,6,7,8-tetrahydronaphthalen-1-yl)-N-(2,2,2-trifluoroethyl)-propanamide, designated as 9 in FIG. 5, was prepared using the same procedure employed for 7, using as starting materials 6 and 2,2,2-trifluoroethanamine hydrochloride salt. Yield: 87%. HPLC-MS retention time: 5.9 min (Method B).

$^1$H NMR (CDCl$_3$): δ 1.22-1.29 (m, 1H), 1.90-1.96 (m, 1H), 2.43-2.53 (m, 2H), 2.60-2.65 (m, 1H), 2.68-2.74 (m, 1H), 2.78-2.84 (m, 1H), 2.89-2.96 (m, 3H), 3.67 (m, 1H), 3.86-3.94 (m, 2H), 4.97 (d, J=7.6 Hz, 1H), 5.84 (bs, 1H), 6.81 (d, J=7.5 Hz, 1H), 6.98 (d, J=7.5 Hz, 1H), 7.05 (t, J=7.5 Hz, 1H), 7.48 (d, J=8.5 Hz, 2H), 7.80 (d, J=8.5 Hz, 2H) ppm. $^{13}$C NMR (CDCl$_3$): δ 23.6, 28.1, 29.4, 36.6, 37.0, 40.8 (q, $J_{CF}^2$=34.6 Hz), 49.2, 126.5, 127.0, 128.2, 128.6, 129.7, 133.1, 133.7, 138.8, 139.4, 139.7, 172.5 ppm. IR: ν 3290, 3088, 2939, 2888, 1670, 1553 cm$^{-1}$. HRMS (ESI+): calculated for $C_{21}H_{22}ClN_2O_3F_3SNa^+$ 497.0889. found 497.0866.

3-(6-(4-Chlorophenylsulfonamido)-5,6,7,8-tetrahydronaphthalen-1-yl)-N-(4-fluorophenyl)propanamide was prepared using the same procedure employed for 7, using as starting materials 6 and para-fluoroaniline. Yield: 82%.

$^1$H NMR (CDCl$_3$): δ 1.72-1.79 (m, 1H), 1.92-1.94 (m, 1H), 2.52-2.66 (m, 3H), 2.70-2.76 (m, 1H), 2.81-2.86 (m, 1H), 2.93-2.99 (m, 3H), 3.66-369 (m, 1H), 4.98 (d, J=7.7 Hz, 1H), 6.82 (d, J=7.1 Hz, 1H), 6.98-7.08 (m, 4H), 7.25 (broad s, 1H), 7.40-7.43 (m, 2H), 7.47 (d, J=8.6 Hz, 2H), 7.90 (d, J=8.06 Hz, 2H) ppm. $^{13}$C NMR (CDCl$_3$): δ 23.6, 28.2, 29.4, 37.0, 37.8, 49.2, 115.8 (d, $J_{CF}^2$=22.1 Hz), 121.9 (d, $J_{CF}^3$=7.9 Hz), 126.5, 127.2, 128.2, 128.6, 129.7, 133.2, 133.7, 134.2 (d, $J_{CF}^1$=253.1 Hz), 139.1, 139.4, 139.7, 158.2, 170.6 ppm. IR: ν 3482, 3285, 1643 cm$^{-1}$. HRMS (ESI+): calculated for $C_2H_{24}ClFNaN_2O_3S^+$ 509.1078. found 509.1089.

Example 5

Synthetic Protocols

Figure 6:
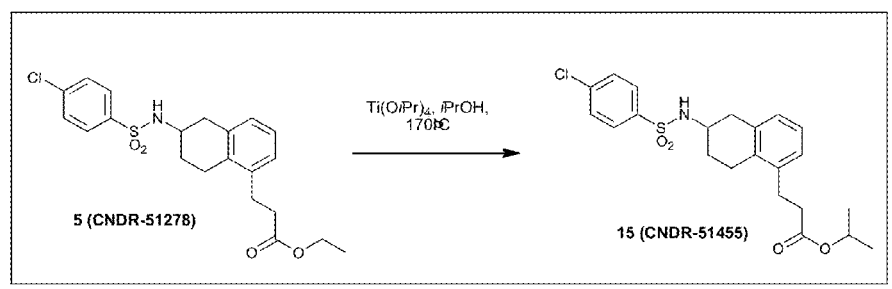
FIG. 6 is a schematic representation of a synthetic route to generate compounds of the invention.

Isopropyl 3-(6-(4-chlorophenylsulfonamido)-5,6,7,8-tetrahydronaphthalen-1-yl)propanoate, designated as 15 in FIG. 6, was prepared as follows. A mixture of ethyl 3-(6-(4-chlorophenylsulfonamido)-5,6,7,8-tetrahydronaphthalen-1-yl) propanoate (33 mg. 0.078 mmol) and titanium tetraisopropoxide (2 μL) in isopropanol (0.5 mL) was heated to 170° C. for 1 hour using microwave irradiation. After cooling the solvent was evaporated and the residue was purified by preparative HPLC using a gradient from 10 to 90% of acetonitrile in water to provide the desired compound as colorless oil. Yield: 91%.

$^1$H NMR (CDCl$_3$): δ 1.22 (d, J=7.2 Hz, 6H), 1.75-1.82 (m, 1H), 1.97-2.01 (m, 1H), 2.52 (t, J=7.8 Hz, 2H), 2.64 (dd, J=16.2 and 7.8 Hz, 1H), 2.68-2.74 (m, 1H), 2.80-2.87 (m, 3H), 2.96 (dd, J=16.5 and 4.6 Hz, 1H), 3.62-3.69 (m, 1H), 4.83 (d, J=7.6 Hz, 1H), 5.01 (sept, J=6.3 Hz, 1H), 6.83 (d, J=7.3 Hz, 1H), 7.01 (d, J=7.1 Hz, 1H), 7.06 (t, J=7.5 Hz, 1H), 7.49 (d, J=8.7 Hz, 2H), 7.84 ppm (d, J=8.7 Hz, 2H). $^{13}$C NMR (CDCl$_3$): δ 122.0, 24.0, 27.9, 29.7, 34.8, 37.2, 49.4, 68.1, 126.4, 126.9, 128.0, 28.6, 129.6, 133.2, 133.6, 138.9, 139.3, 139.8, 172.6 ppm. IR: ν 3384, 3283, 1725 cm$^{-1}$. HRMS (ESI+): calculated for $C_{22}H_{26}ClNaNO_4S^+$ 458.1169. found 458.1165.

Example 6

Synthetic Protocols

4-Chloro-N-(5-(3-hydroxypropyl)-1,2,3,4-tetrahydronaphthalen-2-yl)benzenesulfonamide, designated as 16 in FIG. 7 was prepared as follows. Diisobutylaluminium hydride in dichloromethane (0.84 mL, 1 M, 0.84 mmol) was added dropwise to a solution of ethyl-3-(6-(4-chlorophenylsulfonamido)-5,6,7,8-tetrahydronaphthalen-1-yl)propanoate (60 mg, 0.14 mmol) in dichloromethane (2 mL) at −78° C. The reaction was allowed to warm to 0° C. over 3 hour. Sodium potassium tartrate solution (10 mL, 1 M aqueous solution) was then added and stirring continued at room temperature for 1 hour. The organic layer was separated and the aqueous layer extracted with dichloromethane. The combined organic layers were dried over sodium sulfate and concentrated to dryness. Silica gel chromatography (50% ethyl acetate in hexanes) gave the purified product as colorless oil (54 mg). Yield: 100%.

HPLC-MS retention time: 6.5 min (Method A). $^1$H NMR (CDCl$_3$): δ 1.74-1.84 (m, 3H), 1.96-2.00 (m, 1H), 2.59-2.65 (m, 3H), 2.68-2.72 (m, 1H), 2.73-2.85 (m, 1H), 2.93-2.97 (m, 1H), 3.66 (m, 1H), 3.71 (t, J=12.5 Hz, 2H), 4.82 (bs, 1H), 6.82 (d, J=7.5 Hz, 1H), 7.01-7.03 (m, 1H), 7.05-7.08 (m, 1H), 7.47 (d, J=9.0 Hz, 2H), 7.83 (d, J=9.0 Hz, 2H) ppm. $^{13}$C NMR (CDCl$_3$): δ 23.8, 29.0, 29.7, 32.9, 37.1, 49.3, 62.6, 126.3, 127.2, 127.7, 128.6, 129.6, 133.1, 133.5, 139.2, 139.7, 140.2 ppm. IR: ν 3505, 3276, 2934, 2878, 1585 cm$^{-1}$. HRMS (ESI−): calculated for $C_{19}H_{21}ClNO_3S^-$ 378.0931. found 378.0915.

4-Fluoro-N-(5-(3-hydroxypropyl)-1,2,3,4-tetrahydronaphthalen-2-yl)benzenesulfonamide, designated as 17 in FIG. 7, was prepared using the same procedure employed for 16, using as starting material 6. Yield: 99%.

$^1$H NMR (CDCl$_3$): δ 1.79-1.85 (m, 3H), 1.97-2.01 (m, 1H), 2.60-2.65 (m, 3H), 2.69-2.75 (m, 1H), 2.80-2.86 (m, 1H), 2.96 (dd, J=16.1 and 4.75 Hz, 1H), 3.65-3.72 (m, 3H), 4.60 (d, J=7.8 Hz, 1H), 6.83 (d, J=7.15 Hz, 1H), 7.02-7.08 (m, 2H), 7.20 (t, J=7.5 Hz, 2H), 7.91 (dd, J=8.9 and 5.1 Hz, 2H) ppm. $^{13}$C NMR (CDCl$_3$): δ 23.9, 29.1, 29.8, 33.0, 37.2, 49.4, 62.7, 116.6 (d, $J_{F}^2$=22.2 Hz), 126.4, 127.3, 127.7, 129.9 (d, $J_{CF}^3$=9.1 Hz), 133.2, 133.6, 137.4, 140.3, 165.3 (d, $J_{CF}^1$=253.1 Hz) ppm. IR: ν 3280, 1590 cm$^{-1}$. MS (ESI+): calculated for $C_{19}H_{23}FNO_3S$ 364.14. found 364.11.

N-(5-(3-Hydroxypropyl)-1,2,3,4-tetrahydronaphthalen-2-yl)-4-(trifluoromethyl)benzenesulfonamide, designated as 18 in FIG. 7, was prepared using the same procedure employed for 16, using as starting material 7. Yield: 61%.

$^1$H NMR (CDCl$_3$): δ 1.66 (m, 1H), 1.83-1.75 (m, 3H), 2.01-1.96 (m, 1H), 2.86-2.60 (m, 5H), 2.95 (dd, J=16.2, 4.7 Hz, 1H), 3.69 (m, 3H), 5.27 (d, J=7.6 Hz, 1H), 6.80 (d, J=7.1 Hz, 1H), 7.03 (dt, J=15.5, 7.5 Hz, 2H), 7.78 (d, J=8.3 Hz, 2H), 8.02 (d, J=8.2 Hz, 2H) ppm. $^{13}$C NMR (CDCl$_3$): δ 23.8, 29.0, 29.7, 32.9, 37.1, 49.5, 62.6, 123.4 (d, $J_{CF}^1$=271 Hz), 126.2, 126.4, 126.4, 126.5, 127.2, 127.6, 133.1, 133.4, 134.4 (d, $J_{CF}^2$=33.4 Hz), 140.2, 144.9 ppm. IR: ν 3280, 2935 cm$^{-1}$. MS (ESI$^+$): calculated for $C_{20}H_{23}F_3NO_3S^+$ 414.14. found 414.07.

4-Chloro-N-(5-(3-oxopropyl)-1,2,3,4-tetrahydronaphthalen-2-yl)benzenesulfonamide, designated as 19 in FIG. 7, was prepared as follows. A solution of pyridinium chlorochromate (162 mg, 0.75 mmol) in dichloromethane (9.5 mL) was added to a solution of 4-chloro-N-(5-(3-hydroxypropyl)-1,2,3,4-tetrahydronaphthalen-2-yl)benzenesulfonamide (190 mg, 0.50 mmol) in dichloromethane (22 mL) and the resulting mixture was stirred at room temperature for 1 hour. The reaction mixture was filtered through celite and the solvent removed under reduced pressure. The residue so obtained was purified via a short plug of silica gel (eluent: 50% ethyl acetate in hexanes) obtaining the title compound as colorless oil (145 mg). Yield: 77%.

N-(5-(3-Oxopropyl)-1,2,3,4-tetrahydronaphthalen-2-yl)-4-(trifluoromethyl)benzenesulfonamide, designated as 21 in FIG. 7, was prepared using the same procedure employed for 19, using as starting material 18. Yield: 64%.

$^1$H NMR (CDCl$_3$): δ 1.86-1.80 (m, 1H), 2.05-1.99 (m, 1H), 2.75-2.63 (m, 4H), 2.89-2.79 (m, 3H), 2.98 (dd, J=16.2, 4.7 Hz, 1H), 3.73 (m, 1H), 4.76 (d, J=7.8 Hz, 1H), 6.84 (d, J=7.5 Hz, 1H), 6.99 (d, J=7.4 Hz, 1H), 7.07 (t, J=7.6 Hz, 1H), 7.80 (d, J=8.2 Hz, 2H), 8.03 (d, J=8.2 Hz, 2H), 9.84 (t, J=1.3 Hz, 1H) ppm.

4-Chloro-N-(5-(4,4,4-trifluoro-3-hydroxybutyl)-1,2,3,4-tetrahydronaphthalen-2-yl)benzene-sulfonamide, designated as 22 in FIG. 7, was prepared as follows. A solution of 4-chloro-N-(5-(3-oxopropyl)-1,2,3,4-tetrahydronaphthalen-2-yl)benzenesulfonamide (145 mg, 0.38 mmol) in THF (2.0 mL) was cooled to 0° C. Tetrabutylammoniumfluoride in THF (20 μL, 1 M, 0.02 mmol) was added followed by trifluoromethyl trimethylsilane (82 mg, 0.58 mmol). The reaction was warmed to room temperature overnight. Hydrochloric acid (1 M, 3 mL) was added and stirring continued at room temperature for 1.5 hour. The aqueous layer was extracted with dichloromethane, dried over magnesium sulfate and concentrated to dryness. Silica gel chromatography (30% ethyl acetate in hexanes) gave the purified product as colorless oil (55 mg). Yield: 32%.

HPLC-MS retention time: 7.8 min (Method A). $^1$H NMR (CDCl$_3$): δ 1.18-1.88 (m, 2H), 1.91-1.96 (m, 2H), 2.54 (dd, J=23.0/5.5 Hz, 1H), 2.67-2.71 (m, 3H), 2.79-2.85 (m, 2H), 2.96 (bd, J=16.0 Hz, 1H), 3.66 (m, 1H), 4.07 (m, 1H), 4.93 (dd, J=13.4/7.6 Hz, 1H), 6.84 (d, J=7.4 Hz, 1H), 7.02 (d, J=7.3 Hz, 1H), 7.07 (t, J=7.4, 1H), 7.49 (d, J=8.5 Hz, 2H), 7.82 (d, J=8.5, 2H) ppm. $^{13}$C NMR (CDCl$_3$): δ 23.9, 23.9, 27.8, 27.9, 29.7, 29.8, 30.0, 37.2, 37.2, 49.4, 49.4, 70.1 (q, $J_{CF}^2$=31.2 Hz), 70.3 (q, $J_{CF}^2$=31.1 Hz), 126.5, 126.6, 127.3, 127.3, 128.2, 128.2, 128.7, 129.7, 133.2, 133.3, 133.8, 133.8, 138.9, 139.0, 139.4, 139.8, 139.9 ppm. IR: ν 3466, 3278, 2934, 1586 cm$^{-1}$. MS (ESI$^+$): calculated for $C_{20}H_{22}ClF_3NO_3S^+$ 448.1. found 448.1.

4-Fluoro-N-(5-(4,4,4-trifluoro-3-hydroxybutyl)-1,2,3,4-tetrahydronaphthalen-2-yl)benzenesulfonamide, designated as 23 in FIG. 7, was prepared as follows. A mixture of 4-fluoro-N-(5-(3-hydroxypropyl)-1,2,3,4-tetrahydronaphthalen-2-yl)benzenesulfonamide (70 mg, 0.19 mmol) and pyridinium chlorochromate (60 mg, 0.28 mmol) in anhydrous dichloromethane (3 mL) was stirred at room temperature for 1 hour. The reaction mixture was filtered through a pad of celite, and the solvent was evaporated. The residue was purified by a short silica gel column chromatography using ethyl acetate-hexanes 2:3 as eluent to give 4-fluoro-N-(5-(3-oxopropyl)-1,2,3,4-tetrahydronaphthalen-2-yl)benzenesulfonamide (20) that was dissolved in anhydrous tetrahydrofuran (1 mL) and cooled to 0 C. Tetrabutylammoniumfluoride in THF (5 μL, 1 M, 0.004 mmol) was added followed by trifluoromethyl trimethylsilane (30 mg, 33 μL, 0.21 mmol). The reaction was warmed to room temperature and stirred overnight. Hydrochloric acid (1 M, 1.5 mL) was added and stirring continued at room temperature for 1.5 hour. The aqueous layer was extracted with dichloromethane, dried over magnesium sulfate and concentrated to dryness. Silica gel chromatography (30% ethyl acetate in hexanes) gave the purified product as colorless oil. Yield: 13%.

$^1$H NMR (CDCl$_3$): δ 0.89-0.97 (m, 1H), 1.81-2.06 (m, □): d 4H), 2.61-2.99 (m, 6H), 3.68-3.69 (m, 1H), 3.93-3.95 (m, 1H), 4.51 (d, J=5.6 Hz, 1H), 6.86 (d, J=7.4 Hz, 1H), 7.03-7.10 (m, 2H), 7.21 (t, J=8.5 Hz, 2H), 7.90-7.93 (m, 2H) ppm.

N-(5-(4,4,4-Trifluoro-3-hydroxybutyl)-1,2,3,4-tetrahydronaphthalen-2-yl)-4-(trifluoromethyl)benzenesulfonamide, designated as 24 in FIG. 7, was prepared using the same procedure employed for 22, using as starting material 21. Yield: 25%

$^1$H NMR (CDCl$_3$): δ 1.88-1.80 (m, 2H), 2.05-1.93 (m, 2H), 2.23 (dd, J=16.2, 5.8 Hz, 1H), 2.88-2.63 (m, 5H), 3.01-2.97 (m, 1H), 3.76-3.71 (m, 1H), 3.97-3.90 (m, 1H), 4.73 (t, J=7.1 Hz, 1H), 6.85 (d, J=7.4 Hz, 1H), 7.06 (m, 2H), 7.80 (d, J=8.5 Hz, 2H), 8.02 (d, J=8.2 Hz, 2H) ppm. $^{13}$C NMR (CDCl$_3$): δ 23.84, 23.88, 27.9, 29.8, 29.8, 29.98, 37.2, 37.2, 49.5, 60.6, 70.1, 70.2, 70.4, 122.4, 124.5, 126.4, 126.5, 126.56, 126.59, 127.3, 127.4, 127.7, 128.2, 133.2, 133.2, 133.6, 133.66, 134.5, 134.8, 138.9, 139.0, 145.0 ppm. IR: ν 3459, 3284, 2938, 1637 cm$^{-1}$. HRMS (ESI$^+$): calculated for $C_{21}H_{21}F_6NO_3SNa^+$ 504.1036. found 504.1040.

4-Chloro-N-(5-(4,4,4-trifluoro-3-oxobutyl)-1,2,3,4-tetrahydronaphthalen-2-yl)benzenesulfonamide, designated as 25 in FIG. 7, was prepared as follows. Dess-Martin periodinane (23 mg, 0.05 mmol) was added to a solution of the trifluorormethyl alcohol 22 (32.7 mg, 0.08 mmol) in dichloromethane (2 mL) and the reaction was stirred at room temperature for 2 hour. The reaction mixture was diluted with dimethylsulfoxide and the resulting mixture was directly purified by reverse phase preparative HPLC obtaining the title compound as colorless oil (5 mg). Yield: 22%. HPLC-MS retention time: 7.7 min (Method A).

$^1$H NMR($C_6D_6$): δ 1.78-1.83 (m, 1H), 2.00-2.07 (m, 1H), 2.62-2.83 (m, 3H), 2.90-2.93 (m, 2H), 2.97-3.00 (m, 3H), 3.67-3.72 (m, 1H), 4.53 (d, J=7.5 Hz, 1H), 6.88 (d, J=7.0 Hz, 1H), 6.99 (d, J=7.0 Hz, 1H), 7.09 (t, J=7.5 Hz, 1H), 7.51 (d, J=8.5 Hz, 2H), 7.84 (d, J=8.5 Hz, 2H) ppm. $^{13}$C NMR ($C_6D_6$): δ 24.5, 25.3, 30.1, 36.6, 37.4, 49.6, 129.0, 129.7, 133.5, 134.5, 137.6, 139.0, 141.2, 190.7 ppm. IR: ν 3278, 2932, 1763, 1586 cm$^{-1}$. HRMS (ESI$^-$): calculated for $C_{20}H_{18}ClF_3NO_3S^-$ 444.0648. found 444.0630.

Example 7

Synthetic Protocols

Figure 8:
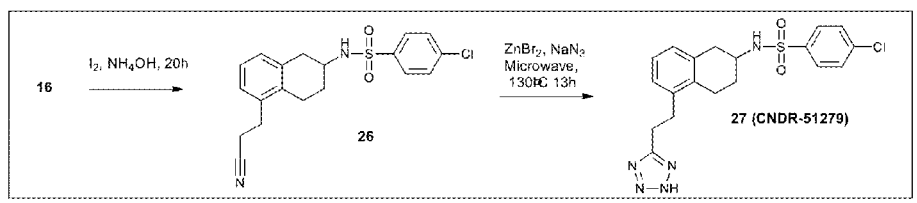
FIG. 8 is a schematic representation of a synthetic route to generate compounds of the invention.

4-Chloro-N-(5-(2-cyanoethyl)-1,2,3,4-tetrahydronaphthalen-2-yl)benzenesulfonamide, designated as 26 in FIG. 8, was prepared as follows. A solution of 4-chloro-N-(5-(3-hydroxypropyl)-1,2,3,4-tetrahydronaphthalen-2-yl)benzene-sulfonamide (55 mg, 0.14 mmol) in ammonium hydroxide (1.5 mL) was added with iodine (110 mg, 0.43 mmol) and the resulting mixture was stirred at 60° C. for 24 hour. The reaction was then quenched at 0° C. by addition of a saturated solution of sodium sulfite (2 mL). The mixture so obtained was extracted with dichloromethane. The organic layer was then dried over magnesium sulfate and concentrated to dryness; the resulting material was purified by column chromatography (Silica gel; Biotage SP4; gradient of ethyl acetate in hexanes) obtaining the title compound (15.7 mg). Yield: 29%.

HPLC-MS retention time: 7.2 min (Method A). $^1$H NMR (CDCl$_3$): δ 1.79-1.82 (m, 1H), 1.99-2.02 (m, 1H), 2.58 (t, J=7.5 Hz, 2H), 2.63-2.73 (m, 2H), 2.79-2.84 (m, 1H), 2.91 (t, J=7.5 Hz, 2H), 2.95-2.99 (m, 1H), 3.64-3.69 (m, 1H), 4.83 (d, J=7.6 Hz, 1H), 4.98 (bs, 1H), 6.90 (d, J=7.6 Hz, 1H), 7.04 (d, J=7.5 Hz, 1H), 7.11 (t, J=7.5 Hz, 1H), 7.50 (d, J=9.0 Hz, 2H), 7.83 (d, J=9.0 Hz, 2H) ppm. $^{13}$C NMR (CDCl$_3$): δ 18.0, 23.9, 28.2, 29.5, 37.0, 49.1, 119.2, 126.2, 127.1, 128.1, 128.6, 129.0, 129.6, 133.0, 134.1, 136.3, 139.3 ppm. IR: ν 3268, 2931, 2248, 1586 cm$^{-1}$. HRMS (ESI$^+$): calculated for C$_{19}$H$_{19}$ClN$_2$O$_2$SNa$^+$ 397.0753. found 397.0760.

N-(5-(2-(2H-Tetrazol-5-yl)ethyl)-1,2,3,4-tetrahydronaphthalen-2-yl)-4-chlorobenzenesulfonamide, designated as 27 in FIG. 8, was prepared as follows. 4-Chloro-N-(5-(2-cyanoethyl)-1,2,3,4-tetrahydronaphthalen-2-yl)benzenesulfonamide (126 mg, 0.37 mmol) was added with a 1 M aqueous solution of sodium azide (367 μL, 0.37 mmol) and a 1 M aqueous solution of zinc bromide (335 μL, 0.33 mmol). The resulting mixture was stirred in a microwave reactor at 130° C. for 12 hour. The reaction vial was then repeatedly washed with 1 N hydrochloric acid and ethyl acetate until no solid residues were observed. The water layer was extracted with ethyl acetate and the combined organic extracts were then dried over magnesium sulfate and evaporated to dryness. The residue obtained was finally purified by column chromatography (Silica gel: Biotage SP4; gradient of methanol in dichloromethane) obtaining the title compound (20.0 mg). Yield: 14.2%.

HPLC-MS retention time: 5.9 min (Method A). $^1$H NMR (MeOD): δ 1.71-1.77 (m, 1H), 1.96-2.00 (m, 1H), 2.71 (m, 2H), 2.90 (d, J=16.8 Hz, 2H), 3.05 (t, J=7.8 Hz, 2H), 3.18-3.22 (m, 2H), 3.51-3.55 (m, 1H), 6.85 (d, J=7.6 Hz, 1H), 6.90 (d, J=7.4 Hz, 1H), 7.01 (t, J=7.6 Hz, 1H), 7.62 (d, J=8.8 Hz, 2H), 7.91 (d, J=8.8 Hz, 2H) ppm. $^{13}$C NMR (MeOD): δ 24.9, 25.6, 31.1, 31.7, 38.0, 50.9, 127.3, 127.9, 129.2, 129.8, 130.6, 134.7, 136.0, 138.9, 139.8, 142.3, 157.6 ppm. IR: ν 3268, 2920, 2848, 1707, 1586 cm$^{-1}$. HRMS (ESI$^-$): calculated for C$_{19}$H$_{19}$ClN$_5$O$_2$S$^-$ 416.0936. found 416.0948.

Example 8

Synthetic Protocols

Figure 9:
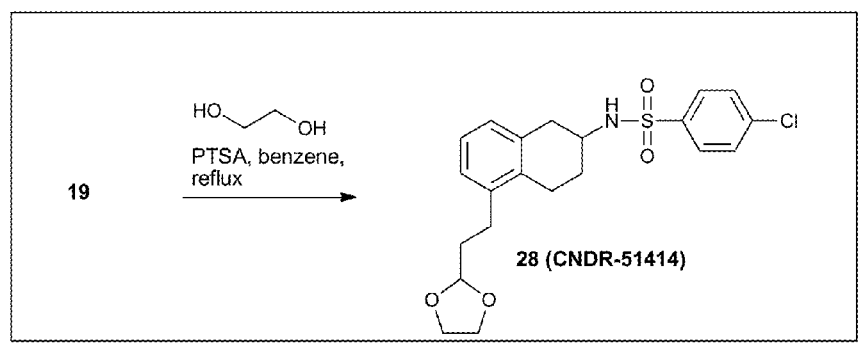
FIG. 9 is a schematic representation of a synthetic route to generate compounds of the invention.

N-(5-(2-(1,3-Dioxolan-2-yl)ethyl)-1,2,3,4-tetrahydronaphthalen-2-yl)-4-chlorobenzenesulfonamide, designated as 28 in FIG. 9, was prepared as follows. A solution of 4-chloro-N-(5-(3-oxopropyl)-1,2,3,4-tetrahydronaphthalen-2-yl)benzene-sulfonamide (44 mg, 0.12 mmol) in benzene (20 mL) was added with ethylene glycol (9.7 μL, 0.17 mmol) and catalytic amount of para-toluensulfonic acid. The resulting mixture was stirred while heated to reflux for 8 hour. The reaction mixture was then evaporated to dryness and the residue so obtained was dissolved in dichloromethane and extracted 5 times with saturated solution of sodium bisulfite. The organic layer was then dried over magnesium sulfate and after filtration of the drying agent and evaporation of the volatiles, 40 mg of product was obtained which was purified by column chromatography (hexane/AcOEt 7:3) to yield the desired compound (40 mg). Yield: 81%.

HPLC-MS retention time: 6.4 min (Method B). $^1$H NMR (CDCl$_3$): δ 1.74-1.80 (m, 1H), 1.81-1.92 (m, 2H), 1.98-2.01 (m, 1H), 2.62-2.74 (m, 4H), 2.79-2.85 (m, 1H), 2.96 (dd, J=16.1/4.3 Hz, 1H), 3.65-3.68 (m, 1H), 3.87-3.92 (m, 2H), 3.97-4.02 (m, 2H), 4.76 (d, J=7.6 Hz, 1H), 4.91, (t, J=4.5 Hz, 1H), 6.83 (d, J=7.1 Hz, 1H), 7.02-7.08 (m, 2H), 7.49 (d, J=8.4 Hz, 2H), 7.83 (d, J=8.4 Hz, 2H) ppm. $^{13}$C NMR (CDCl$_3$): δ 23.9, 26.9, 29.7, 34.1, 37.1, 49.4, 65.1, 104.1, 126.3, 127.1, 127.7, 128.6, 129.6, 133.1, 133.5, 139.2, 139.8, 139.9 ppm. IR: ν 3274, 2927, 2884, 1585 cm$^{-1}$. HRMS (ESI$^-$): calculated for C$_{21}$H$_{23}$ClNO$_4$S$^-$ 420.1036. found 420.1017.

Example 9

Figure 10:
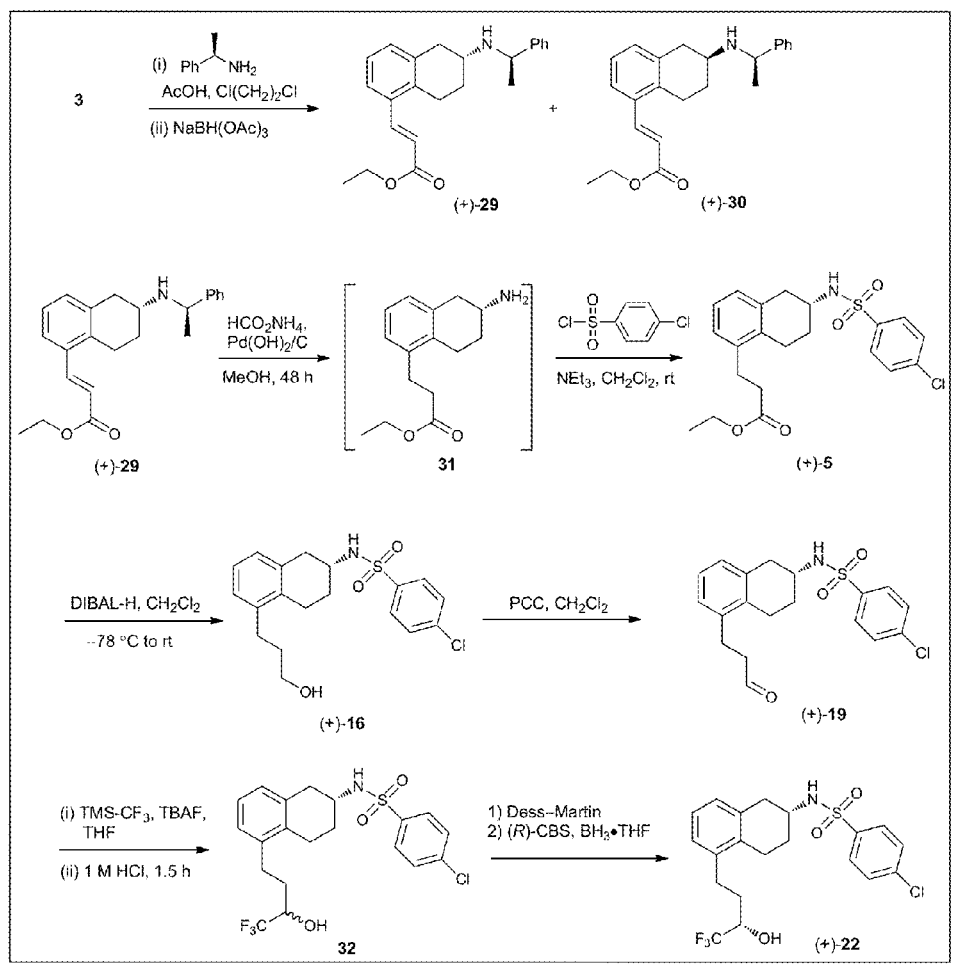
FIG. 10 is a schematic representation of a synthetic route to generate compounds of the invention.

Synthetic Protocols (E)-Ethyl-3-((R/S)-6-(((R)-1-phenylethyl)amino)-5,6,7,8-tetrahydronaphthalen-1-yl)acrylate, designated as (+)-29/(+)-30 in FIG. 10, was prepared as follows. A solution of (E)-ethyl-3-(6-oxo-5,6,7,8-tetrahydronaphthalen-1-yl)acrylate (127.4 mg, 0.52 mmol) and (R)-1-phenylethylamine (66 μL, 0.52 mmol) in acetic acid (0.12 mL, 2.10 mmol) and dichloroethane (4 mL) was stirred at room temperature for 45 min. Sodium triacetoxyborohydride (663.2 mg, 3.13 mmol) was added and stirring continued at room temperature for 16 hour. The reaction was quenched by the addition of saturated sodium bicarbonate solution and basified to pH ~8 with sodium hydroxide (1 M). The aqueous layer was extracted with dichloromethane; the organic layer dried over sodium sulfate and concentrated to dryness (174.3 mg). Yield: 96%. The ~1:1 mixture of diastereomers were separated by column chromatography (silica gel, Biotage SP4; gradient: 10% to 20% ethyl acetate in hexanes).

(E)-ethyl-3-((R)-6-(((R)-1-phenylethyl)amino)-5,6,7,8-tetrahydronaphthalen-1-yl)acrylate, (+)-29:

$[α]_D^{19}$=+40.6 (c=0.77, CDCl$_3$). $^1$H NMR (CDCl$_3$): δ 1.32 (t, J=7.1 Hz, 3H), 1.38 (d, J=6.5 Hz, 3H), 1.57-1.65 (m, 1H), 1.94-1.96 (m, 1H), 2.62 (dd, J=15.4/9.2 Hz, 1H), 2.70-2.81 (m, 2H), 2.98 (dt, J=17.2/4.8 Hz, 1H), 3.06 (dd, J=15.4/3.7 Hz, 1H), 4.03 (q, J=6.5 Hz, 1H), 4.25 (q, J=7.1 Hz, 2H), 6.28 (d, J=15.8 Hz, 1H), 7.09-7.13 (m, 2H), 7.21-7.24 (m, 1H), 7.30-7.36 (m, 5H), 7.92 (d, J=15.8 Hz, 1H) ppm; NH not observed. $^{13}$C NMR (CDCl$_3$): δ 14.5, 25.1, 25.8, 30.5, 37.1, 50.0, 55.2, 60.7, 119.9, 124.5, 126.1, 126.7, 127.1, 128.7, 131.6, 133.6, 135.8, 136.4, 142.4, 146.0, 167.2 ppm. IR: ν 2966, 2924, 2853, 1711 cm$^{-1}$. HRMS (ESI$^+$): calculated for C$_{23}$H$_{28}$NO$_2$$^+$ 350.2120. found 350.2108.

(E)-ethyl-3-((S)-6-(((R)-1-phenylethyl)amino)-5,6,7,8-tetrahydronaphthalen-1-yl)acrylate, (+)-30:

$[α]_D^{18}$=+42.3 (c=0.33, CDCl$_3$). $^1$H NMR (CDCl$_3$): δ 1.33 (t, J=7.1 Hz, 3H), 1.38 (d, J=6.5 Hz, 3H), 1.56-1.63 (m, 1H), 2.16-2.19 (m, 1H), 2.59 (dd, J=16.1/9.1 Hz, 1H), 2.69-2.79 (m, 2H), 2.85 (dd, J=16.1/3.7 Hz, 1H), 3.01 (dt, J=17.6/4.9 Hz, 1H), 4.04 (q, J=6.5 Hz, 1H), 4.25 (q, J=7.1 Hz, 2H), 6.29 (d, J=15.8 Hz, 1H), 7.03 (d, J=7.4 Hz, 1H), 7.11-7.08 (m, 1H), 7.21-7.24 (m, 1H), 7.30-7.35 (m, 5H), 7.99 (d, J=15.8 Hz, 1H) ppm; NH not observed. $^{13}$C NMR (CDCl$_3$): δ 14.6, 25.1, 25.6, 28.8, 38.2, 49.9, 55.1, 60.7, 119.9, 124.5, 126.1, 126.7, 127.1, 128.7, 131.5, 133.6, 135.8, 136.6, 142.5, 146.1, 167.2 ppm. IR: ν 2958, 2925, 2853, 1711 cm$^{-1}$. HRMS (ESI$^+$): calculated for C$_{23}$H$_{28}$NO$_2$$^+$ 350.2120. found 350.2112.

(R/S)-Ethyl-3-(6-(4-chlorophenylsulfonamido)-5,6,7,8-tetrahydronaphthalen-1-yl)-propanoate, designated as (+/−)-5 in FIG. 10, was prepared as follows. Palladium hydroxide/carbon (225.0 mg) and ammonium formate (775.1 mg, 12.29 mmol) were added to a solution of (E)-ethyl-3-((R/S)-6-(((R)-1-phenylethyl)amino)-5,6,7,8-tetrahydronaphthalen-1-yl)acrylate (433.4 mg, 1.24 mmol) in methanol (20 mL) and heated at 50° C. for 48 hour. After cooling to room temperature, the reaction mixture was filtered through celite. The solvent was removed under reduced pressure and the product, (R/S)-ethyl 3-(6-amino-5,6,7,8-tetrahydronaphthalen-1-yl)propanoate (designated as 31 in FIG. 10), was used in the next reaction without further purification.

Triethylamine (34 µL, 2.45 mmol) and 4-chlorobenzene-sulfonyl chloride (271.3 mg, 1.29 mmol) were added to a solution of (R/S)-ethyl 3-(6-amino-5,6,7,8-tetrahydronaphthalen-1-yl)propanoate in dichloromethane (40 mL). After stirring for 16 hour at room temperature, the reaction mixture was diluted with dichloromethane and washed with water. The organic layer was dried over sodium sulfate and concentrated to dryness. Silica gel chromatography (20% ethyl acetate in hexanes) gave the purified product as colorless oil (466.2 mg). Yield: 89% (2 steps).

$^1$H NMR (CDCl$_3$): δ 1.25 (t, J=7.1 Hz, 3H), 1.75-1.82 (m, 1H), 1.97-2.01 (m, 1H), 2.55 (t, J=7.8 Hz, 2H), 2.63 (dd, J=16.5/7.9 Hz, 1H), 2.68-2.74 (m, 1H), 2.78-2.83 (m, 1H), 2.86 (t, J=7.8 Hz, 2H), 2.96 (dd, J=16.5/4.5 Hz, 1H), 3.65-3.68 (m, 1H), 4.13 (q, J=7.1 Hz, 2H), 4.65 (d, J=7.8 Hz, 1H), 6.83 (d, J=7.4 Hz, 1H), 7.00 (d, J=7.4 Hz, 1H), 7.04-7.07 (m, 1H), 7.49 (d, J=8.7 Hz, 2H), 7.82 (d, J=8.7 Hz, 2H) ppm. $^{13}$C NMR (CDCl$_3$): δ 14.4, 23.9, 27.8, 29.7, 34.6, 37.2, 49.4, 60.7, 126.5, 126.9, 128.1, 128.7, 129.7, 133.2, 133.6, 138.9, 139.3, 139.9, 173.1 ppm. IR: ν 3398, 2924, 2848, 1586 cm$^{-1}$. HRMS (ESI$^+$): calculated for C$_{21}$H$_{25}$NO$_4$SCl$^+$ 422.1193. found 422.1180. (R)-isomer: [α]$_D^{20}$=+18.0 (c=0.33, CDCl$_3$). (S)-isomer: [α]$_D^{17}$=−23.5 (c=1.12, CDCl$_3$).

Mosher amide analysis of (S)-ethyl 3-(6-amino-5,6,7,8-tetrahydronaphthalen-1-yl)-propanoate 4-Dimethylaminopyridine (14.2 mg, 0.12 mmol) and (R)-(+)-α-methoxy-α-trifluoromethylphenylacetyl chloride (9 µL, 48 µmol) were added to a solution of (S)-ethyl 3-(6-amino-5,6,7,8-tetrahydronaphthalen-1-yl)propanoate (9.8 mg, 40 µmol) in dichloromethane (3 mL) and stirred at room temperature for 16 hour. The reaction mixture was diluted with water; the organic layer was separated and the aqueous layer extracted with dichloromethane. The combined organic layers were dried over sodium sulfate and concentrated to dryness. Silica gel chromatography (20% ethyl acetate in hexanes) gave the purified product as colorless oil (8.2 mg). Yield: 44%.

$^1$H NMR (CDCl$_3$): δ 1.27 (t, J=7.1 Hz, 3H), 1.78-1.85 (m, 1H), 2.10-2.15 (m, 1H), 2.53-2.58 (m, 2H), 2.75 (dd, J=16.2/8.7 Hz, 1H), 2.78-2.80 (m, 2H), 2.89 (t, J=8.1 Hz, 2H), 3.19 (dd, J=16.2/5.4 Hz, 1H), 3.41 (d, J=1.4 Hz, 3H), 4.16 (q, J=7.1 Hz, 2H), 4.29-4.36 (m, 1H), 6.73 (d, J=8.6 Hz, 1H), 6.98 (d, J=7.5 Hz, 1H), 7.03 (d, J=7.6 Hz, 1H), 7.09-7.12 (m, 1H), 7.42-7.44 (m, 3H), 7.55-7.57 (m, 1H) ppm; NH not observed.

4-Dimethylaminopyridine (12.7 mg, 0.10 mmol) and (S)-(+)-α-methoxy-α-trifluoromethylphenylacetyl chloride (9 µL, 48 µmol) were added to a solution of the amine (9.8 mg, 40 µmol) in dichloromethane (3 mL) and stirred at room temperature for 16 hour. The reaction mixture was diluted with water; the organic layer was separated and the aqueous layer extracted with dichloromethane. The combined organic layers were dried over sodium sulfate and concentrated to dryness. Silica gel chromatography (20% ethyl acetate in hexanes) gave the purified product as colorless oil (11.6 mg). Yield: 61%.

$^1$H NMR (CDCl$_3$): δ 1.25 (t, J=7.1 Hz, 3H), 1.83-1.90 (m, 1H), 2.14-2.19 (m, 1H), 2.56-2.59 (m, 2H), 2.71 (dd, J=16.2/8.9 Hz, 1H), 2.79-2.88 (m, 2H), 2.90-2.93 (m, 2H), 3.12 (dd, J=16.2/4.8 Hz, 1H), 3.37 (d, J=1.4 Hz, 3H), 4.14 (q, J=7.1 Hz, 2H), 4.28-4.35 (m, 1H), 6.83 (d, J=8.2 Hz, 1H), 6.94 (d, J=7.4 Hz, 1H), 7.02 (d, J=7.3 Hz, 1H), 7.07-7.10 (m, 1H), 7.40-7.44 (m, 3H), 7.51-7.56 (m, 1H) ppm; NH not observed.

HRMS (ESI$^+$): calculated for C$_{25}$H$_{29}$NO$_4$F$_3$$^+$ 464.2049. found 464.2061.

(R/S)-4-Chloro-N-(5-(3-hydroxypropyl)-1,2,3,4-tetrahydronaphthalen-2-yl)benzene-sulfon-amide, designated as (+/−)-16 in FIG. 10, was prepared as follows. Diisobutylaluminium hydride in dichloromethane (0.9 mL, 1 M, 0.90 mmol) was added dropwise to a solution of (R/S)-ethyl-3-(6-(4-chlorophenylsulfonamido)-5,6,7,8-tetrahydronaphthalen-1-yl)propanoate (74.3 mg, 0.18 mmol) in dichloromethane (20 mL) at −78° C. The reaction was allowed to warm to room temperature over 3 hour. As tlc analysis of the reaction mixture showed the presence of starting material, the reaction was re-cooled to −78° C. and additional diisobutylaluminium hydride (0.18 mL, 0.18 mmol) was added; the reaction was then warmed to room temperature over 1 hour. Sodium potassium tartrate solution (aq, 1 M, 10 mL) was added and stirring continued at room temperature for 20 min. The organic layer was separated and the aqueous layer extracted with dichloromethane. The combined organic layers were dried over sodium sulfate and concentrated to dryness. Silica gel chromatography (50% ethyl acetate in hexanes) gave the purified product as colorless oil (64.7 mg). Yield: 950%.

$^1$H NMR (CDCl$_3$): δ 1.28 (bs, 1H), 1.77-1.84 (m, 3H), 1.98-2.00 (m, 1H), 2.60-2.64 (m, 3H), 2.69-2.73 (m, 1H), 2.79-2.84 (m, 1H), 2.96 (dd, J=16.5/4.9 Hz, 1H), 3.68-3.71 (m, 3H), 4.56 (d, J=8.2 Hz, 1H), 6.82 (d, J=7.2 Hz, 1H), 7.01-7.08 (m, 2H), 7.49 (d, J=8.4 Hz, 2H), 7.82 (d, J=8.4 Hz, 2H) ppm. $^{13}$C NMR (CDCl$_3$): δ 23.9, 29.1, 29.8, 33.0, 37.3, 49.4, 62.7, 126.4, 127.3, 127.8, 128.7, 129.7, 133.2, 133.5, 139.4, 139.9, 140.3 ppm. IR: ν 3373, 2922, 2858, 1586 cm$^{-1}$. HRMS (ESI$^-$): calculated for C$_{19}$H$_{21}$NO$_3$SCl$^-$ 378.0931. found 378.0925. (R)-isomer: [α]$_D^{21}$=+7.8 (c=0.15, CDCl$_3$). (S)-isomer: [α]$_D^{21}$=−28.2 (c=0.10, CDCl$_3$).

(R/S)-4-Chloro-N-(5-(3-oxopropyl)-1,2,3,4-tetrahydronaphthalen-2-yl)benzenesulfonamide, designated as (+/−)-19 in FIG. 10, was prepared as follows. Pyridinium chlorochromate (196.8 mg, 1.44 mmol) was added to a solution of (R/S)-4-chloro-N-(5-(3-hydroxypropyl)-1,2,3,4-tetrahydronaphthalen-2-yl)benzene-sulfonamide (361.6 mg, 0.95 mmol) in dichloromethane (50 mL) and stirred at room temperature for 3 hour. The reaction mixture was filtered through celite and the solvent removed under reduced pressure. Silica gel chromatography (20% to 50% ethyl acetate in hexanes) gave the purified product as colorless oil (310.6 mg). Yield: 87%.

$^1$H NMR (CDCl$_3$): δ 1.75-1.82 (m, 1H), 1.87-2.02 (m, 1H), 2.61-2.70 (m, 2H), 2.71 (t, J=7.5 Hz, 2H), 2.77-2.83 (m, 1H), 2.86 (t, J=7.5 Hz, 2H), 2.95 (dd, J=16.5/4.8 Hz, 1H), 3.62-3.68 (m, 1H), 4.82 (d, J=7.6 Hz, 1H), 6.83 (d, J=7.4 Hz, 1H), 6.97 (d, J=7.4 Hz, 1H), 7.07-7.04 (m, 1H), 7.48 (d, J=8.5 Hz, 2H), 7.82 (d, J=8.5 Hz 2H), 9.82 (s, 1H) ppm. $^{13}$C NMR (CDCl$_3$): δ 24.0, 24.9, 29.7, 37.1, 43.9, 49.3, 126.5, 126.9, 128.1, 128.6, 129.7, 133.2, 133.8, 138.6, 139.3, 139.8, 201.5 ppm. IR: ν 2917, 2852, 1560 cm$^{-1}$. HRMS (ESI$^-$): calculated for C$_{19}$H$_{19}$NO$_3$SCl$^-$ 376.0774. found 376.0786. (R)-isomer: [α]$_D^{21}$=+16.7 (c=0.48, CDCl$_3$). (S)-isomer: [α]$_D^{20}$=−15.6 (c=0.38, CDCl$_3$).

4-Chloro-N-((2R/S)-5-(4,4,4-trifluoro-3-hydroxybutyl)-1,2,3,4-tetrahydronaphthalen-2-yl)-benzene-sulfonamide, designated as 32 in FIG. 10, was prepared as follows. A solution of (R/S)-4-chloro-N-(5-(3-oxopropyl)-1,2,3,4-tetrahydronaphthalen-2-yl)benzenesulfonamide (60.4 mg, 0.16 mmol) in THF (1.5 mL) was cooled to 0° C. Tetrabutylammoniumfluoride in THF (20 µL, 1 M, 0.02 mmol) was added followed by trifluoromethyl trimethylsilane (35 µL, 0.24 mmol). The reaction was warmed to room temperature overnight. Hydrochloric acid (1 M, 3 mL) was added and stirring continued at room temperature for 1.5 hour. The aqueous layer was extracted with dichloromethane, dried over magnesium sulfate and concentrated to dryness. Silica gel chromatography (20% ethyl acetate in hexanes) gave the purified product as colorless oil (29.3 mg). Yield: 41% (starting material was also recovered in 41% yield).

4-Chloro-N-((R/S)-5-((R/S)-4,4,4-trifluoro-3-hydroxybutyl)-1,2,3,4-tetrahydronaphthalen-2-yl)benzenesulfonamide, designated as (+/−)-22/(+/−)-22 in FIG. 10, was prepared as follows. Dess-Martin periodinane (128.8 mg, 0.30 mmol) was added to a solution of the trifluoromethyl alcohol (67.6 mg, 0.15 mmol) in dichloromethane (4 mL) and the reaction was stirred at room temperature for 2 hour. The reaction mixture was diluted with dichloromethane and washed with water. The organic layer was separated, dried over magnesium sulfate and concentrated to dryness. Silica gel chromatography (20% ethyl acetate in hexanes), gave the purified product, (R/S)-4-chloro-N-(5-(4,4,4-trifluoro-3-oxobutyl)-1,2,3,4-tetrahydronaphthalen-2-yl)benzenesulfonamide, as colorless oil (51.1 mg). Yield 76%.

Borane tetrahydrofuran (40 µL, 1 M in THF) was added to a solution of (R/S)-2-methyl-CBS-oxazaborolidine (3 µL, 1 M in toluene) in THF (0.5 mL) at 0° C. After 20 min a solution of (R/S)-4-chloro-N-(5-(4,4,4-trifluoro-3-oxobutyl)-1,2,3,4-tetrahydronaphthalen-2-yl)benzene sulfonamide (9.3 mg, 21 µmol) in THF (1.0 mL) was added dropwise and stirring continued at 0° C. for 2 hour. The reaction was quenched by the addition of methanol and brine. The aqueous layer was extracted with ethyl acetate, dried over magnesium sulfate and concentrated to dryness. Silica gel chromatography (20% ethyl acetate in hexanes), gave the purified product as colorless oil (4.1 mg). Yield: 44%.

(S,S)-isomer [prepared by treatment of (S)-4-chloro-N-(5-(4,4,4-trifluoro-3-oxobutyl)-1,2,3,4-tetrahydronaphthalen-2-yl)benzene sulfonamide with (R)-2-methyl-CBS-oxazaborolidine]: $^1$H NMR (CDCl$_3$): δ 1.76-1.89 (m, 2H), 1.91-2.01 (m, 2H), 2.22 (bs, 1H), 2.61-2.73 (m, 3H), 2.78-2.87 (m, 2H), 2.97 (dd, J=16.8/4.2 Hz, 1H), 3.67-3.69 (m, 1H), 3.91-3.94 (m, 1H), 4.67 (d, J=7.8 Hz, 1H), 6.84 (d, J=7.5 Hz, 1H), 7.02 (d, J=7.3 Hz, 1H), 7.06-7.09 (m, 1H), 7.49 (d, J=8.7 Hz, 2H), 7.82 (d, J=8.7 Hz, 2H) ppm. $^{13}$C NMR (CDCl$_3$): δ 23.9, 27.8, 29.7, 29.7, 37.2, 49.4, 70.1 (q, J$_{CF}^2$=31.0 Hz), 126.5, 127.3, 128.2, 128.7, 129.7, 133.3, 133.8, 138.9, 139.4, 139.8 ppm. IR: ν 2925, 2854, 1587 cm$^{-1}$. HRMS (ESI$^+$): calculated for C$_{20}$H$_{21}$NO$_3$F$_3$NaSCl$^+$ 470.0780 found 470.0757. [α]$_D^{23}$=−44.8 (c=0.70, CDCl$_3$). Chiracel OD-RH column (solvent gradient: 40 to 70% acetonitrile in water over 30 min, 2 mL/min): 13.1 min (79%, (S,S)) and 13.9 min (21%, (S,R); 79:21 dr, >95:5 er.

(R,R)-isomer [prepared by treatment of (R)-4-chloro-N-(5-(4,4,4-trifluoro-3-oxobutyl)-1,2,3,4-tetrahydronaphthalen-2-yl)benzenesulfonamide with (S)-2-methyl-CBS-oxazaborolidine]: [α]$_D^{21}$=+28.2 (c=0.58, CDCl$_3$). Chiracel OD-RH column (solvent gradient: 40 to 70% acetonitrile in water over 30 min, 2 mL/min): 13.3 min (22%, (R,S)) and 17.7 min (78%, (R,R)); 78:22 dr, >95:5 er.

(S,R)-isomer [prepared by treatment of (S)-4-chloro-N-(5-(4,4,4-trifluoro-3-oxobutyl)-1,2,3,4-tetrahydronaphthalen-2-yl)benzenesulfonamide with (S)-2-methyl-CBS-oxazaborolidine]: $^1$H NMR (CDCl$_3$): δ 1.75-1.87 (m, 2H), 1.93-2.01 (m, 2H), 2.18 (d, J=5.7 Hz, 1H), 2.61-2.75 (m, 3H), 2.78-2.87 (m, 2H), 2.96 (dd, J=17.2/4.0 Hz, 1H), 3.66-3.69 (m, 1H), 3.92-3.95 (m, 1H), 4.64 (d, J=7.9 Hz, 1H), 6.84 (d, J=7.4 Hz, 1H), 7.02 (d, J=7.6 Hz, 1H), 7.06-7.09 (m, 1H), 7.49 (d, J=8.5 Hz, 2H), 7.82 (d, J=8.5 Hz, 2H) ppm. $^{13}$C NMR (CDCl$_3$): δ 23.9, 27.8, 29.8, 30.0, 37.2, 49.4, 70.3 (q, J$_{CF}^2$=31.2 Hz), 126.6, 127.3, 128.2, 128.7, 129.7, 133.2, 133.8, 139.0, 139.4, 139.8 ppm. IR: ν 3269, 2928, 2854, 1587 cm$^{-1}$. HRMS (ESI$^+$): calculated for C$_{20}$H$_{21}$NO$_3$F$_3$NaSCl$^+$ 470.0780. found 470.0760. [α]$_D^{23}$=−17.6 (c=0.80, CDCl$_3$). Chiracel OD-RH column (solvent gradient: 40 to 70% acetonitrile in water over 30 min, 2 mL/min): 13.2 min (22%, (S,S)) and 13.9 min (78%, (S,R)); 78:22 dr, >95:5 er.

(R,S)-isomer [prepared by treatment of (R)-4-chloro-N-(5-(4,4,4-trifluoro-3-oxobutyl)-1,2,3,4-tetrahydronaphthalen-2-yl)benzenesulfonamide with (R)-2-methyl-CBS-oxazaborolidine]: [α]$_D^{20}$=+12.6 (c=0.41, CDCl$_3$). Chiracel OD-RH column (solvent gradient: 40 to 70% acetonitrile in water over 30 min, 2 mL/min): 13.2 min (80%, (R,S)) and 17.6 min (20%, (R,R)); 80:20 dr, >95:5 er.

Mosher ester analysis of 4-chloro-N-((S)-5-((R)-4,4,4-trifluoro-3-hydroxybutyl)-1,2,3,4-tetrahydronaphthalen-2-yl)benzenesulfonamide 4-Dimethylaminopyridine (5.8 mg, 47 µmol) and (R)-(+)-α-methoxy-α-trifluoromethylphenylacetyl chloride (5.3 µL, 28 µmol) were added to a solution of 4-chloro-N-((S)-5-((R)-4,4,4-trifluoro-3-hydroxybutyl)-1,2,3,4-tetrahydronaphthalen-2-yl)benzenesulfonamide (10.6 mg, 24 µmol) in dichloromethane (2 mL) and stirred at room temperature for 16 hour. The reaction mixture was diluted with water, the organic layer was separated and the aqueous layer extracted with dichloromethane. The combined organic layers were dried over magnesium sulfate and concentrated to dryness. Silica gel chromatography (20% ethyl acetate in hexanes) gave the purified product as colorless oil (9.0 mg). Yield: 57%.

$^1$H NMR (CDCl$_3$): δ 1.74-1.80 (m, 1H), 1.95-1.99 (m, 1H), 2.02-2.10 (m, 2H), 2.36-2.39 (m, 1H), 2.55-2.60 (m, 2H), 2.61-2.69 (m, 2H), 2.96 (dd, J=16.2/4.4 Hz, 1H), 3.50 (s, 3H), 3.64-3.67 (m, 1H), 4.54 (d, J=8.2 Hz, 1H), 5.52-5.55 (m, 1H), 6.86 (d, J=7.6 Hz, 1H), 6.94 (d, J=7.5 Hz, 1H), 7.06-7.09 (m, 1H), 7.37 (d, J=7.4 Hz, 1H), 7.40-7.44 (m, 3H), 7.50 (d, J=8.4 Hz, 2H), 7.55-7.57 (m, 1H), 7.83 (d, J=8.4 Hz, 2H) ppm.

4-Dimethylaminopyridine (6.1 mg, 50 µmol) and (S)-(+)-α-methoxy-α-trifluoromethylphenylacetyl chloride (5.2 µL, 28 µmol) was added to a solution of 4-chloro-N-((S)-5-((R)-4,4,4-trifluoro-3-hydroxybutyl)-1,2,3,4-tetrahydronaphthalen-2-yl)benzenesulfonamide (10.4 mg, 23 µmol) in dichloromethane (2 mL) and stirred at room temperature for 16 hour. The reaction mixture was diluted with water: the organic layer was separated and the aqueous layer extracted with dichloromethane. The combined organic layers were dried over magnesium sulfate and concentrated to dryness. Silica gel chromatography (20% ethyl acetate in hexanes) gave the purified product as colorless oil (10.7 mg). Yield: 70%.

$^1$H NMR (CDCl$_3$): δ 1.66-1.73 (m, 1H), 1.87-1.93 (m, 2H), 1.96-2.00 (m, 1H), 2.27-2.41 (m, 2H), 2.48 (dt, J=17.4/6.0 Hz, 1H), 2.56-2.65 (m, 2H), 2.92 (dd, J=16.6/4.1 Hz, 1H), 3.62 (s, 3H), 3.65-3.68 (m, 1H), 4.57 (d, J=8.2 Hz, 1H), 5.51-5.55 (m, 1H), 6.82-6.83 (m, 2H), 7.02-7.05 (m, 1H), 7.39-7.44 (m, 4H), 7.51 (d, J=8.5 Hz, 2H), 7.55-7.59 (m, 1H), 7.83 (d, J=8.5 Hz, 2H) ppm.

Example 10

Synthetic Protocols

Figure 11:
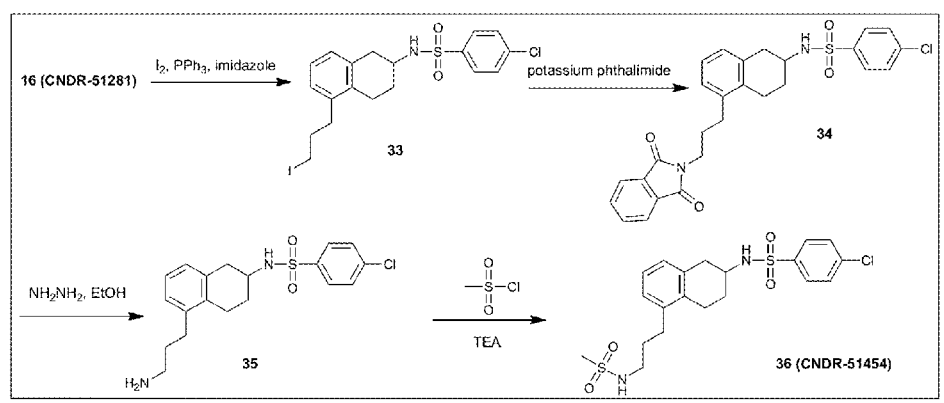
FIG. 11 is a schematic representation of a synthetic route to generate compounds of the invention.
Figure 12A:
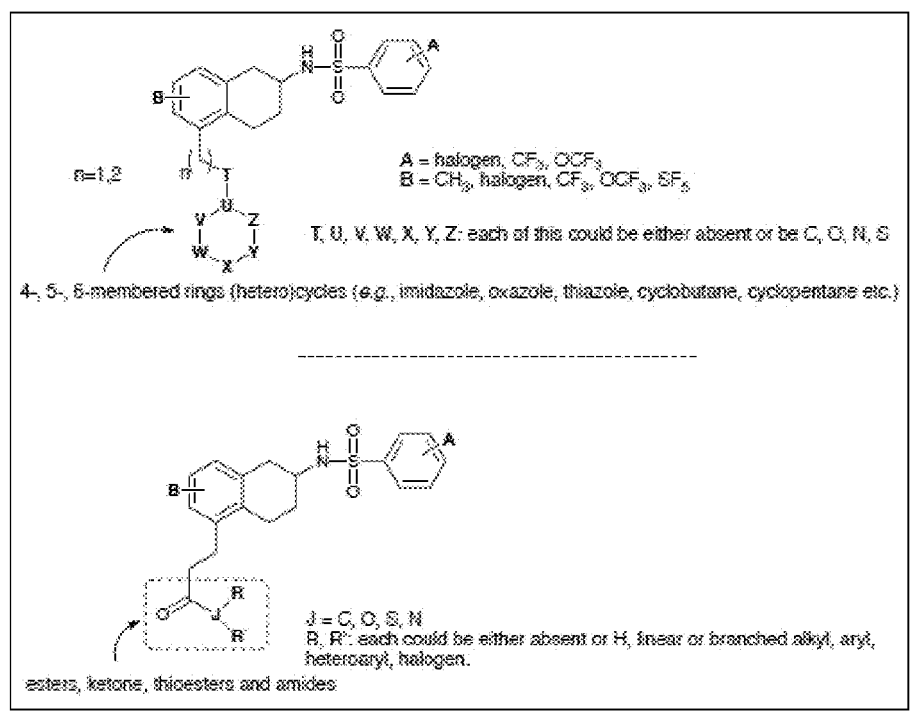
FIGS. 12A-12B, illustrates non-limiting examples of TP receptor antagonists.
Figure 12B:
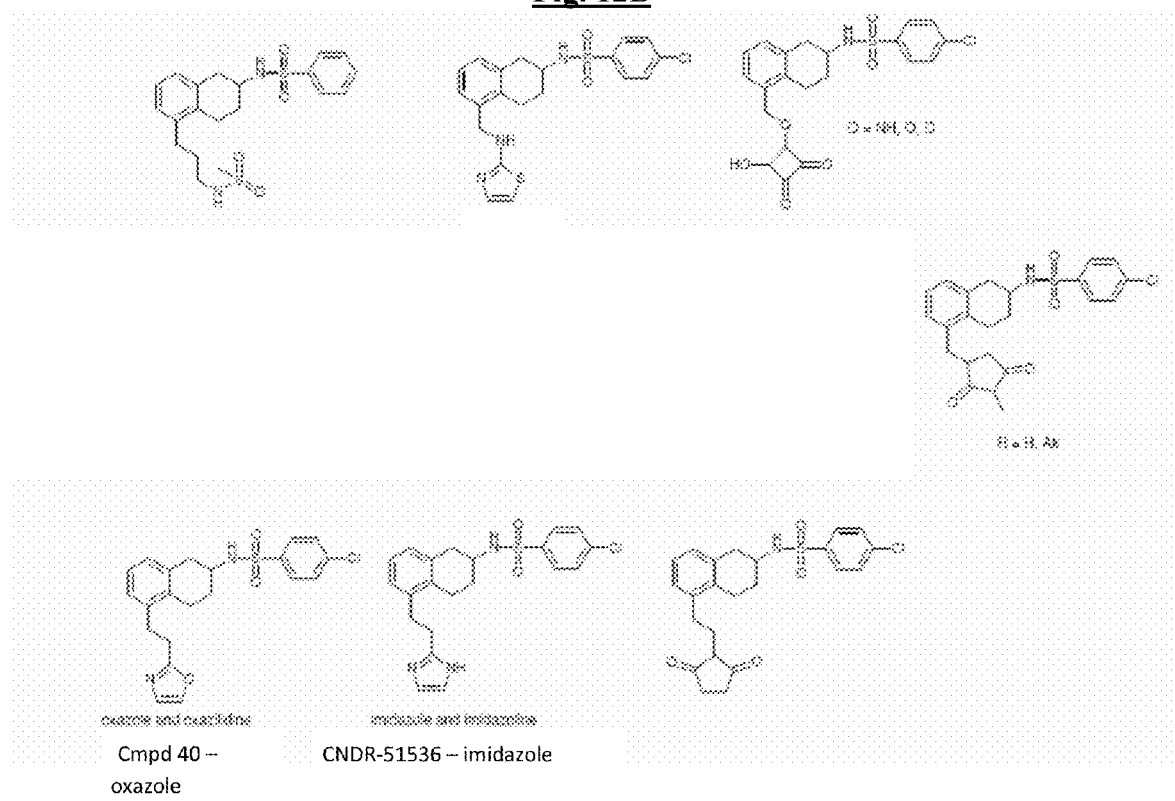

4-Chloro-N-(5-(3-iodopropyl)-1,2,3,4-tetrahydronaphthalen-2-yl)benzenesulfonamide, designated as 33 in FIG. 11, was prepared as follows. Iodine (244 mg, 0.96 mmol) was added to a 0° C. cooled mixture of 4-chloro-N-(5-(3-hydroxypropyl)-1,2,3,4-tetrahydronaphthalen-2-yl)benzenesulfonamide (116 mg, 0.3 mmol), triphenylphosphine (241 mg, 0.92 mmol), and imidazole (65 mg, 0.96 mmol) in anhydrous diethyl ether (5 mL) and acetonitrile (2.3 mL). The reaction mixture was stirred at 0° C. for 2 hour. Diethyl ether was added and the resulting mixture was washed with water and a saturated solution of sodium thiosulfate. The organic layer was dried over sodium sulfate, filtered and evaporated. The residue was purified by silica gel column chromatography using ethyl acetate-hexanes 5:95 as eluent to provide the desired compound as colorless oil. Yield: 61%.

$^1$H NMR (CDCl$_3$): δ 1.75-1.85 (m, 1H), 1.98-2.08 (m, 3H), 2.61-2.75 (m, 4H), 2.79-2.84 (m, 1H), 2.97 (dd, J=16.2 and 4.6 Hz, 1H), 3.22 (t, J=6.8 Hz, 2H), 3.64-3.70 (m, 1H), 4.65 (d, J=7.7 Hz, 1H), 6.84 (d, J=7.4 Hz, 1H), 7.02 (d, J=6.8 Hz, 1H), 7.07 (t, J=7.5 Hz, 1H), 7.50 (d, J=8.6 Hz, 2H), 7.84 (d, J=8.6 Hz, 2H) ppm. $^{13}$C NMR (CDCl$_3$): δ 6.6, 24.0, 29.8, 33.5, 33.7, 37.2, 49.4, 126.4, 127.5, 128.0, 128.7, 129.7, 133.2, 133.7, 138.9, 139.3, 139.9 ppm.

4-Chloro-N-(5-(3-(1,3-dioxoisoindolin-2-yl)propyl)-1,2,3,4-tetrahydronaphthalen-2-yl)benzenesulfonamide, designated as 34 in FIG. 11, was prepared as follows. Potassium phthalimide (23 mg, 0.12 mmol) was added to a solution of 4-chloro-N-(5-(3-iodopropyl)-1,2,3,4-tetrahydronaphthalen-2-yl)benzenesulfonamide (50 mg, 0.10 mmol) in anhydrous dimethylformamide (3 mL). The reaction mixture was heated to 60° C. and stirred for 45 minutes and then poured in water and ethyl acetate. The aqueous layer was extracted with ethyl acetate, and the combined extracted was washed with brine, dried over sodium sulfate, filtered and evaporated. The residue was purified by silica gel column chromatography using ethyl acetate-hexanes 2:3 as eluent to give the desired compound. Yield: 96%.

$^1$H NMR (CDCl$_3$): δ 1.79-1.76 (m, 1H), 1.89-1.92 (m, 1H), 1.98-2.04 (m, 2H), 2.56-2.68 (m, 4H), 2.73-2.80 (m, 1H), 2.92 (dd, J=16.3 and 4.6 Hz, 1H), 3.69-3.76 (m, 3H), 5.19 (d, J=8.15 Hz, 1H), 6.69 (d, J=7.4; H, 1H), 6.94 (t, J=7.5 Hz, 1H), 6.99 (d, J=7.3 Hz, 1H), 7.49 (d, J=8.6 Hz, 2H), 7.69-7.71 (m, 2H), 7.82-7.83 (m, 2H), 7.86 (d, J=8.6 Hz, 2H) ppm. $^{13}$C NMR (CDCl$_3$): δ 23.5, 27.9, 29.3, 30.0, 37.1, 38.2, 49.1, 123.4, 126.2, 126.8, 127.7, 128.6, 129.6, 132.2, 133.1, 133.5, 134.1, 139.1, 139.2, 140.1, 168.7 ppm. MS (ESI$^+$): calculated for $C_{27}H_{26}ClN_2O_4S^+$ 509.13. found 509.08.

4-Chloro-N-(5-(3-(methylsulfonamido)propyl)-1,2,3,4-tetrahydronaphthalen-2-yl)benzenesulfonamide, designated as 36 in FIG. 11, was prepared as follows. A mixture of 4-Chloro-N-(5-(3-(1,3-dioxoisoindolin-2-yl)propyl)-1,2,3,4-tetrahydronaphthalen-2-yl)benzene¬sulfonamide (50 mg, 0.98 mmol) and hydrazine (4 mg, 3.7 µL, 0.12 mmol) in ethanol (1 mL) was heated to reflux temperature for 5 hour. After cooling, the reaction mixture was filtered and the filtrate was diluted with water and extracted with ethyl acetate. The combined organic layers were washed with brine, dried over sodium sulfate, filtered and evaporated. The residue (35, as designated in FIG. 11) was used for the next step without further purification. Methylsulfonyl chloride (13 mg, 0.12 mmol) and triethylamine (12 mg, 16 µL, 0.12 mmol) were added to a mixture of 35 (37 mg, 0.10 mmol) in anhydrous dichloromethane (2 mL). The reaction mixture was stirred at room temperature for overnight and then it was diluted with water and extracted with ethyl acetate. The combined organic layers were washed with brine, dried over sodium sulfate, filtered and evaporated. The residue was purified by preparative HPLC using a gradient from 10% to 90% of acetonitrile in water to furnish the desired compound. Yield: 85% (two steps).

$^1$H NMR (CDCl$_3$): δ 1.64-2.01 (m, 4H), 2.57-2.73 (m, 3H), 2.78-2.84 (m, 1H), 2.95-2.99 (m, 4H), 3.15-3.20 (m, 2H), 3.66-3.72 (m, 1H), 4.34 (t, J=5.9 Hz, 1H), 4.85 (d, J=7.7 Hz, 1H), 6.84 (d, J=7.4 Hz, 1H), 6.99 (d, J=7.1 Hz, 1H), 7.07 (t, J=7.5 Hz, 1H), 7.50 (d, J=8.6 Hz, 2H), 7.84 (d, J=8.6 Hz, 2H) ppm. $^{13}$C NMR (CDCl$_3$): δ 23.6, 29.4, 29.7, 30.3, 37.0, 40.5, 43.2, 49.1, 126.4, 127.1, 128.0, 128.6, 129.6, 133.1, 133.7, 139.1, 139.2, 139.8 ppm. IR: n 3482, 3285, 1643 cm$^{-1}$.

Example 11

Brain-Penetrant Tetrahydronaphthalene Thromboxane A2-Prostanoid (TP) Receptor Antagonists as Prototype Therapeutics for Alzheimer's Disease Described herein is the identification of BBB-permeable TP receptor antagonists. Mouse TP (mTP) receptor and human TP (hTP) receptor cellular assays were developed to facilitate the characterization of the compounds. These include HEK293 cellular assays that permit the evaluation of compound effects on TP receptor-mediated changes in APP mRNA and protein levels, as well as Aβ peptide release, and TP receptor activity assays that measure receptor-mediated stimulation of intracellular inositol triphosphate (IP3) signaling. In addition, compounds were evaluated for brain penetration after administration to mice. Utilizing these tools, selected derivatives of CNDR-51280 that freely enter the brain and retain moderately high affinity for both the mTP and hTP receptors have been identified.

In an attempt to increase the B/P ratio of TP receptor antagonists, several analogues of the S-18886-related tetrahydronaphthalene (THN), CNDR-51280 (FIG. 5) were investigated, in which the carboxylic acid moiety was replaced by a range of heterocyclic bioisosteres, including the 1-H-tetrazole (CNDR-51279) and nonacidic heterocycles, such as oxazoles and thiazoles. Certain of these compounds exhibit excellent brain penetration and reasonably high receptor binding affinity, and thus represent prototype brain-penetrant molecules designed to block TP receptor activation by iPF2αIII and/or thromboxane A2 in AD brain, with a resulting reduction of APP expression and Aβ release.

The known TP receptor antagonist, S-18886, was previously demonstrated to decrease Aβ plaque deposition in the Tg2576 mouse model of AD-like Aβ pathology when administered at 5 mg/kg/day for a 6 month period (Shineman et al., 2008, J. Neurosci. 28:4785-4794) providing evidence that TP receptor antagonists may be plausible therapeutic interventions for AD. Sufficient brain concentrations of S-18886 can be achieved at 5 mg/kg/day to inhibit TP receptor activity, but the relatively poor brain penetration of S-18886 results in plasma concentrations that are 10-fold greater than in the brain. Although this did not prove to be problematic in the proof-of-concept study in Tg2576 mice, extremely high plasma levels of a TP receptor antagonist may not be well tolerated in older AD patients. The TP receptor is involved in platelet aggregation, and prolonged receptor antagonism extends bleeding times in animals (Watts et al., 1991, Br. J. Pharmacol. 102:497-505; Thomas et al., 1998, J. Clin. Invest. 102:1994-2001).

Moreover, humans with a gene defect in the TP receptor have an increased risk of bleeding (Hirata et al., 1994, J. Clin. Invest. 94:1662-1667; Mumford et al., 2010, Blood 115:363-369). Thus, it is desirable to identify BBB-permeable TP receptor antagonists to minimize possible negative effects on hemostasis for indications where prolonged dosing would be required, such as AD. Without wishing to be bound to any particular theory, it is hypothesized that fully BBB-permeable TP receptor antagonists may achieve brain concentrations that result in reduced APP and Aβ levels, but have corresponding plasma compound levels that do not fully compromise platelet function.

The materials and methods employed in these experiments are now described.

IP1 Functional Assay and Schild Analysis

The activity of the TP receptor was measured by quantifying cellular levels of the IP3 metabolite, IP1, using a homogeneous time-resolved fluorescence (HTRF) assay kit (IP-One Tb, Cisbio, Bedford, Mass.). QBI-HEK 293A (MP Biomedicals, Solon, Ohio) cells were transfected with human or mouse TP receptor cDNA (α isoforms) that was cloned into the pcDNA5/TO vector (Invitrogen, Carlsbad, Calif.), and stable transformants were selected. Cells were plated at 10 000 cells/well into 384-well plates (Grenier Bio-One, Monroe, N.C.) in DMEM containing 4.5 g/L glucose (Invitrogen, Carlsbad, Calif.), 10% fetal bovine serum, L-glutamine, and penicillin/streptomycin, followed by incubation for 16 h at 37° C. with 5% $CO_2$. Culture media was removed and cells were then incubated for 15 min at 37° C. with 5% $CO_2$ in 10 mM Hepes, 1 mM $CaCl_2$, 0.4 mM $MgCl_2$, 4.2 mM KCl, 146 mM NaCl, 5.5 mM glucose, 50 mM LiCl, pH 7.4 (stimulation buffer) containing varying concentrations of test antagonist.

I-BOP ([15-(1α,2β(5Z),3α-(1E,3S),4α)]-7-[3-hydroxy-4-(p-iodophenoxy)-1-butenyl-7-oxabicycloheptenoic acid) (Cayman Chemicals, Ann Arbor, Mich.) was added at concentrations indicated in the figure legends in stimulation buffer and incubated for 1 h at 37° C. with 5% $CO_2$. For Schild analyses, antagonist was added at fixed concentrations for 15 min in stimulation buffer, followed by a 1 h incubation with the varying concentrations of I-BOP. Following I-BOP incubation, D2-labeled IP1 and Tb-labeled Anti-IP1 cryptate were then added in lysis buffer per the manufacturer's instructions and incubated for 1 h at 25° C. Plates were subsequently read on a Spectramax M5 microplate reader (Molecular Devices, Sunnyvale, Calif.). Data were expressed as the ratio of acceptor emission (665 nm) over donor emission (620 nm) following donor excitation (313 nm). For Schild analyses, the dose-ratio (DR) was defined as the ratio of the I-BOP $EC_{50}$ in the presence of a given concentration of antagonist to the I-BOP $EC_{50}$ in the absence of antagonist. If the antagonist competes with the agonist for receptor binding, $$DR=1+[antagonist]/K_d$$

Thus, plotting the value of DR-1 vs the concentration of antagonist in a double log-plot generates a line with a slope of 1 where the x-intercept is equal to the $K_d$ for the antagonist. Schild Analysis was performed in GraphPad Prism version 4 for Windows (GraphPad Software, San Diego, Calif.).

Aβ Secretion and APP Assays

QBI-HEK 293A cells stably expressing either mTP or hTP receptor were transfected with pcDNA3.1 (Invitrogen, Carlsbad, Calif.) containing a hygromycin selection cassette and the human APP695 cDNA, and stable transformants were selected (HEK293-TP/APP cells). Cells were plated into 96-well polystyrene plates at 20 000 cells/well in DMEM containing 4.5 g/L glucose (Invitrogen, Carlsbad, Calif.), 10% fetal bovine serum, L-glutamine, and penicillin/streptomycin, followed by incubation for 16 h at 37° C. with 5% $CO_2$. Media was aspirated and replaced with media containing 0.5% fetal bovine serum and test antagonist at varying concentrations. Cells were incubated with test antagonist for 1 h at 37° C. with 5% $CO_2$, followed by the addition of IBOP at a final concentration as indicated in the figure legend, and the cells were incubated an additional 48 h at 37° C. with 5% $CO_2$. Aliquots of culture media were then removed for measurement of Aβ (1-40) and Aβ (1-42) levels by ELISA. Cell lysates were prepared by washing cells in PBS and then scraping cells into RIPA buffer (25 mM Tris, 150 mM NaCl, 1% NP-40, 1% sodium deoxycholate, 0.1% SDS, 0.1 mM PMSF, pH 7.6) containing protease inhibitor cocktail. Lysates were incubated on ice and vortexed every 10 min for 30 min, and then centrifuged at 13 000 g for 30 min at 4° C. The total protein concentration in the supernatant was detected by BCA assay (Thermo Scientific, Ill.), and 30 μg of total protein was separated by 10% SDSPAGE and transferred to nitrocellulose membrane. Membranes were blocked in blocking buffer (LiCor Biosciences, Lincoln, Nebr.), incubated overnight at 4° C. with primary antibody to detect the C terminus of APP (5685) or tubulin (12G10), washed, incubated with IRDye 800CW or 680RD conjugated secondary antibodies, and imaged with the Odyssey imaging system (LI-COR Biosciences, Lincoln, Nebr.). Blot quantification was performed using Image Studio (LI-COR Biosciences, Lincoln, Nebr.).

Aβ ELISA 384-well plates were coated with 10 μg/mL of Ban50 as a capture antibody and incubated overnight at 4° C. Plates were blocked for a minimum of 3 days at 4° C. with Block-Ace (AbD Serotec, Raleigh, N.C.). Blocking solution was then removed, and media samples were diluted onto plates and incubated for 16 h at 4° C. Plates were subsequently washed and incubated with the HRPconjugated antibodies BA27 (Aβ (1-40)ELISA) or BC05 (Aβ(1-42)ELISA)46 for 4 h at 25° C. and subsequently subjected to chemiluminescence detection.

APP Quantitative PCR

Cells were treated with I-BOP, or I-BOP and S-18886, as described above, and mRNA was purified using a RNEasy kit (Qiagen, Venlo, Netherlands). The RNA was subjected to a single round of reverse transcription using the SuperScript III First-Strand Synthesis System (Invitrogen, Carlsbad, Calif.) to generate cDNA. For RT-PCR, 1 μL of cDNA was added to each well containing SYBR Green Master Mix (Invitrogen, Carlsbad, Calif.) and forward and reverse primers at a final concentration of 100 nM (APP) or 300 nM (GAPDH), which were the concentrations of primer sets determined to be 100% efficient. PCR was run on the Applied Biosystems 7500 Fast Real-time PCR system (Life Technologies, Foster City, Calif.) using the $\Delta\Delta C_t$ comparative method. Human APP cDNA was quantified and normalized to human GAPDH as an internal control. The primer sequences that were used are as follows:

```
                                         (SEQ ID NO. 1)
   hAPP forward:  CCGCTCTGCAGGCTGTTC (SEQ ID NO. 2)
   hAPP reverse:  GCGGACATACTTCTTTAGCATATTGA (SEQ ID NO. 3)
   hGAPDH forward: GAAGGTGAAGGTCGGAGTCAACG (SEQ ID NO. 4)
   hGAPDH reverse: CCAGAGTTAAAAGCAGCCCTGGTG
```

Radioligand Binding Assay

QBI-HEK 293A cells expressing hTP or mTP receptor were grown as described previously and harvested in phosphate-buffered saline with 1 mM EDTA. The cell pellet was homogenized in a glass homogenizer in 20 mM Hepes, 1 mM EGTA, and 0.5 mM DTT with protease inhibitor cocktail. The homogenate was initially centrifuged at 1000 g for 10 min at 8° C. to remove cell debris. The resulting supernatant was then centrifuged in a Beckman L8-70 M ultracentrifuge (Beckman-Coulter, Brea, Calif.) at 21 000 rpm for 30 min at 4° C., and the pellet was resuspended in 20 mM Hepes, 1 mM EGTA, and 100 mM NaCl. Protein level in the membrane preparation was determined with a BCA assay (Thermo-Fisher, Rockland, Ill.), and the samples were stored at −80° C. Varying concentrations of $^3$H-SQ-29,548 (PerkinElmer, Waltham, Mass.) were incubated with 25 μg membrane in 50 mM Tris, 4 mM CaCl2, 0.1% ascorbic acid, pH 7.5 for 2 h at 25° C. in 96-well polystyrene plates. Separation of bound from free radioligand was accomplished by rapid vacuum filtration onto 96-well GF/B filter plates (PerkinElmer, Waltham, Mass.). Filters were washed 8 times in 50 mM Tris, pH 6.9 and allowed to dry for 16 h. Plates were sealed and filters were dissolved in 50 mL of Betaplate Scintillation fluid (PerkinElmer, Waltham, Mass.), followed by analysis on a PerkinElmer 1450 LSC Microbeta Trilux scintillation counter (PerkinElmer, Waltham, Mass.). Nonspecific binding was determined by incubating $^3$H-SQ-29,548 at multiple concentrations in the presence of 100 μM cold SQ-29,548.

Mouse Pharmacokinetics

One month old female B6C3F1 mice (Charles River Laboratories, Wilmington, Mass.) were administered 5 mg/kg compound in DMSO via an intraperitoneal (IP) injection (groups of 3 or more mice/tested compound). After 1 h, animals were anesthetized with ketamine/xylazine in accordance with protocols approved by the University of Pennsylvania and according to the NIH guide for the care and use of Laboratory Animals. Blood was collected via cardiac puncture, and animals were perfused with PBS. Plasma was separated from blood as described (Brunden et al., 2011, Pharmacol. Res. 63:341-351). Brains were collected and prepared for compound quantification.

Compound Quantification in Tissues

Aliquots (50 μL) of mouse brain homogenate (1:2 w/v in 10 mM NH$_4$OAc, pH 5.7) or plasma were extracted with acetonitrile (1:5 v/v), centrifuged, and the supernatant removed for LC-MS/MS analysis (Waters Acquity UPLCTQD, Milford, Mass.). Analytes were separated by reversed phase liquid chromatography using a water/acetonitrile/0.1% formic acid gradient and detected in the positive ion mode. Data were acquired using multiple reaction monitoring of compound specific collision-induced ion transitions. Standard curves were generated for each compound using spiked brain homogenate or plasma and extracted as above. Peak area was plotted against concentration and a linear regression curve was used to quantify the unknowns.

Determination of Compound Plasma and Brain Unbound Fraction

The unbound fractions of compound in mouse plasma and brain were determined using a rapid equilibrium dialysis as previously described (Brunden et al., 2011, Pharmacol. Res. 63:341-351).

Data Analysis

Equilibrium dissociation constants ($K_d$), $IC_{50}$ values, and Schild intercepts were calculated with GraphPad Prism software (GraphPad Software Inc., La Jolla, Calif.).

The results of the experiments are now described.

Previous data revealed that the TP receptor can regulate APP mRNA stability, and thus may play a role in AD pathogenesis (Shineman et al., 2008, J. Neurosci. 28:4785-4794). To examine further the linkage between TP receptor activation and increased APP expression, HEK293 cell lines stably expressing human APP (hAPP) and the hTP receptor (α isoform) were established. Treatment of these cells for 48 h with the potent TP agonist, [S-1α,2β(5Z),3α(1E,3R*),4α)]-7-[-3-(3-hydroxy-4-(4"-iodophenoxy)-1-butenyl)-7-oxabicyclo-[2.2.1]-heptan-2-yl]-5-heptenoic acid (I-BOP) (Morinelli et al., 1989, J. Pharmacol. Exp. Ther. 251:557-562), resulted in a dose-dependent increase in APP protein levels, with an $EC_{50}$ of 0.8 nM as measured by immunoblot (FIG. 13A). The I-BOP treatment also resulted in a 2.5-fold increase of Aβ(1-40) release from the hTP receptor-hAPP-expressing cells, as determined by ELISA, with an $EC_{50}$ value of 0.3 nM (FIG. 13B). A similar I-BOP-induced enhancement of Aβ(1-42) release was observed, although the absolute levels of Aβ(1-42) were lower than for Aβ(1-40). To confirm that the I-BOP-induced effect on APP and Aβ levels is dependent on TP receptor activity, the hTP receptor-hAPP cells were concurrently treated with I-BOP and the known TP receptor antagonists, daltroban 29 or S-18886 (structures shown in Table 4).

TABLE 4

Known TP Receptor Antagonists Are Poorly Brain-Penetrant

| Compound | Structure | Brain (nM) | Plasma (nM) | S/P |
|---|---|---|---|---|
| Daltroban | 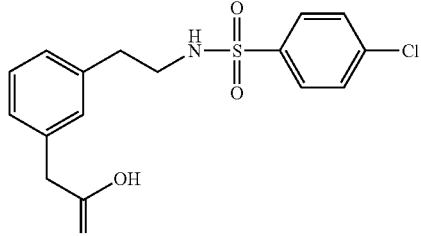 | <LOD | 7226 (+/−1009) | ND |
| S18886 | 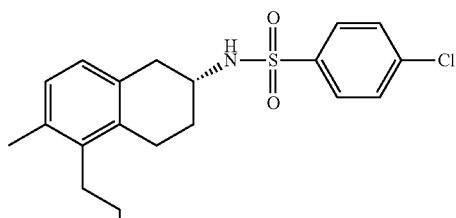 | 187 (+/−19) | 1301 (+/−431) | 0.14 |

TABLE 4-continued

Known TP Receptor Antagonists Are Poorly Brain-Penetrant

| Compound | Structure | Brain (nM) | Plasma (nM) | S/P |
|---|---|---|---|---|
| 8M-567 | 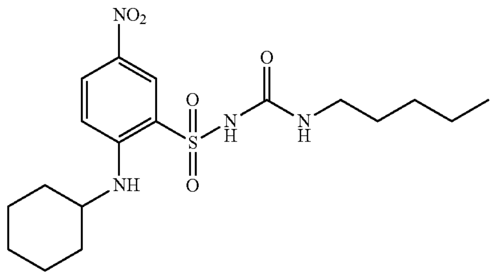 [SMILES: CCCCCNC(=O)NS(=O)(=O)c1cc([N+](=O)[O-])ccc1NC1CCCCC1] | 46 (+/−14) | 5631 (+/−803) | 0.008 |
| SQ29,54g | 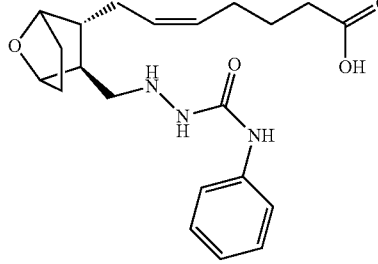 | <LOD | 58 (+/−20) | ND |
| Ramatroban | 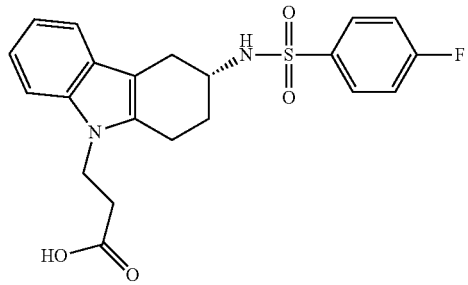 [SMILES: O=C(O)CCn1c2c(c3ccccc31)C[C@H](NS(=O)(=O)c1ccc(F)cc1)CC2] | <LOD | 920 (+/−136) | ND |
| Vapiprost | 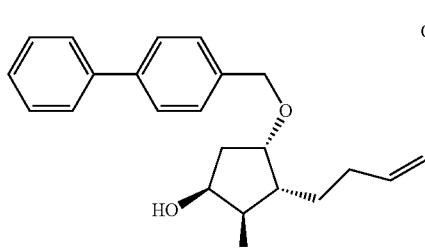 | 8.1 (+/−1.1) | 654 (+/−62) | 0.012 |

1 month old mice were administered 5 mg/kg of antagonist. Drug levels were assessed by LC-MS/MS from brain and plasma samples obtained 1 h after dosing. LOD = below the limit of detection. ND = not determined. Values are presented as mean ± SD.

Both antagonists decreased Aβ(1-40) release, with $IC_{50}$ values of 105 and 16 nM for daltroban and S-18886, respectively (FIG. 13C).

To verify that the TP receptor-mediated effects on APP and Aβ levels resulted from changes in APP mRNA, quantitative PCR was performed on hTP receptor-hAPP cells treated with IBOP. The I-BOP-treated cells showed a 3-fold increase in APP mRNA (FIG. 13D), which correlated well with the increase in APP protein and Aβ(1-40) production (FIG. 13A-13B). This I-BOP-induced increase of APP mRNA was blocked when the hTP receptor-hAPP cells were pretreated with S-18886 (FIG. 13D). HEK293 cells were also created that stably expressed the mTPα receptor and hAPP, and these cells showed a comparable increase of APP mRNA upon treatment with I-BOP that was inhibited by S-18886 pretreatment (FIG. 13D). These data thus confirm that TP receptor activation increases APP mRNA and protein expression, with a consequent elevation of Aβ(1-40/42) levels (Shineman et al., 2008, J. Neurosci. 28:4785-4794) and these effects can be inhibited by known TP receptor antagonists. Without wishing to be bound by any particular theory, the TP receptor-induced increase of APP mRNA is presumed to be mediated through the action of receptor-associated G-proteins, and it is known that the TP receptor couples primarily with Gq, although there is evidence of other G-protein subtype interactions (Knezevic et al., 1993, Blood 82:A 156).

Figure 14:
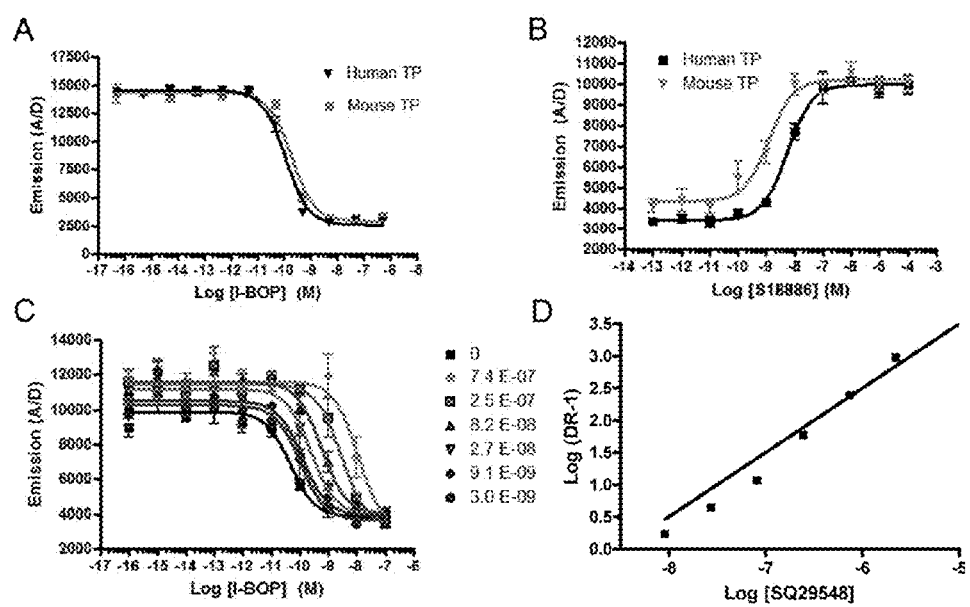
FIG. 14, comprising

To confirm that Gq is coupled to the hTP and mTP receptors in the HEK293 cells, a HTRF assay was utilized to measure the production of IP1, which is a metabolite of the IP3 that is formed after Gq-mediated phospholipase C activation. Treatment of cells expressing hTP or mTP receptors with I-BOP resulted in a dose-dependent increase in IP1 production, as evidenced by a decreased ratio of acceptor-to-donor fluorophore emission (A/D) following donor excitation in the HTRF assay, with $EC_{50}$ values of 0.12 nM for hTP receptor cells and 0.19 nM for mTP receptor cells, respectively (FIG. 14A). This assay thus provides a useful and robust method for measuring TP receptor activation. The TP receptor antagonist, S-18886, blocked I-BOP-induced IP1 production, with an IC50 value of 5.4 nM in hTP receptor cells and 1.2 nM in mTP receptor cells (FIG. 14B).

Specific and saturable binding of $^3$H-SQ-29,548, a radiolabeled TP receptor antagonist (Dorn et al., 1987, Biochem. Pharmacol. 36:1913-1917; Trachte, 1986, J. Pharmacol. Exp. Ther. 237:473-477) to membrane preparations from hTP or mTP receptor cells was also measured, with $K_d$ values of 40 and 15 nM for the hTP and mTP receptors, respectively. However, the manufacture of $^3$H-SQ-29,548 was discontinued during the course of these studies, which led to approximation of receptor binding affinities by the Schild method (Colquhoun, 2007, Trends Pharmacol. Sci. 28:608-614; Giraldo et al., 2007, Curr. Drug Targets 8:197-202). To validate the Schild method, I-BOP concentration-response curves were generated in the IP1 assay in the presence of increasing concentrations of SQ-29,548, as depicted in FIG. 14C for mTP receptor cells.

A Schild plot of these data indicated an apparent $K_d$ value of 3 nM for SQ-29,548 interaction with the mTP receptor (FIG. 14D), and a similar analysis of SQ-29,548 with hTP receptor cells led to a calculated $K_d$ value of 7 nM. These values are in general agreement with the binding affinities determined by radio-ligand binding, and without wishing to be bound to any particular theory, this suggests that the Schild method provides a reasonable approximation of receptor binding affinity.

The ability of known TP receptor antagonists to prevent agonist-induced increases of APP and Aβ suggests that such compounds may have utility in the treatment of AD. The vast majority of known TP receptor antagonists contain a carboxylic acid moiety, which is thought to be a critical contributor to the stability of the drug-receptor complex via ionic interaction with arginine residue 295 of the TP receptor (Funk et al., 1993, Mol. Pharmacol. 44:934-939). However, this anionic group could hamper the passive diffusion of these compounds across the BBB (Austin et al., 1995, J. Pharm. Sci. 84:1180-1183; Barbu et al., 2009, Expert Opin. Drug Delivery 6:553-565). The brain penetration of several known TP receptor antagonists was examined (Table 4), with compounds administered (5 mg/kg i.p.) to wild type mice, followed by mass spectrometric assessment of plasma and brain compound levels 1 h after dosing. There were very low to undetectable brain concentrations of all of the compounds, with brain-to-plasma (B/P) compound levels <<1 (Table 4). Of the compounds tested, S-18886 had the highest apparent brain penetration, with a B/P ratio of 0.14 that typically indicates poor BBB permeability. However, it is possible for a BBB-permeable compound to have a very low B/P ratio if the fraction of free, unbound compound is much greater in the brain than in the plasma (e.g., 7-fold greater unbound fraction in brain than plasma for a compound with a B/P ratio of 0.14). However, estimation of the unbound compound fraction in plasma (2.6%) and brain homogenate (4.4%) by a standard equilibrium dialysis methodology revealed only a 1.7-fold difference in free compound in these tissues, and thus S-18886 does not appear to fully equilibrate across the BBB. The poor BBB permeability of existing TP receptor antagonists suggests that compounds that more readily enter the brain to modulate APP and Aβ levels would be desirable for the treatment of AD. Although a TP receptor antagonist with moderately low brain penetration, such as S-18886, can reach sufficient brain concentrations to inhibit TP receptor activity when administered at relatively high doses to mice (Shineman et al., 2008, J. Neurosci. 28:4785-4794), such doses result in very high plasma compound levels that could adversely affect platelet function when used chronically to treat elderly AD patients.

Compounds

In an attempt to increase the B/P ratio of TP receptor antagonists, several analogues of the S18886-related tetrahydronaphthalene (THN), CNDR-51280 (see Table 5), were investigated in which the carboxylic acid moiety was replaced by a range of heterocyclic bioisosteres, including the 1-H-tetrazole and nonacidic heterocycles, such as thiazoles or oxazoles. The syntheses of CNDR-51280 and the corresponding tetrazole derivative CNDR-51279 are highlighted in FIG. 5. The syntheses of oxazoles 40 and 49 and thiazoles 47 and 48 are illustrated in FIG. 15.

In both cases, the synthesis entailed a Heck coupling reaction to install the ethylacrylate onto the 5-bromo-2-tetralone 2 (Chandra et al., 2007, Org. Lett. 9:5027-5029) to provide the keto-ester 3 (FIG. 5). Next, reductive amination of 3 with benzylamine was followed by catalytic hydrogenation and sulfonylation of the resulting amine to furnish ester CNDR-51278, which could be hydrolyzed to CNDR-51280, or used for the synthesis of CNDR-51279. Thus, reduction of the ester moiety of CNDR-51278 to alcohol CNDR-51281 was followed by oxidative conversion of the primary alcohol to the nitrile 14 (Iida and Togo, 2007, Tetrahedron 63:8274-8281), which was finally reacted with sodium azide under microwave promoted conditions (Demko and Sharpless, 2001, J. Org. Chem. 66:7945-7950) to obtain the 1-H-tetrazole CNDR-51279.

Figure 15:
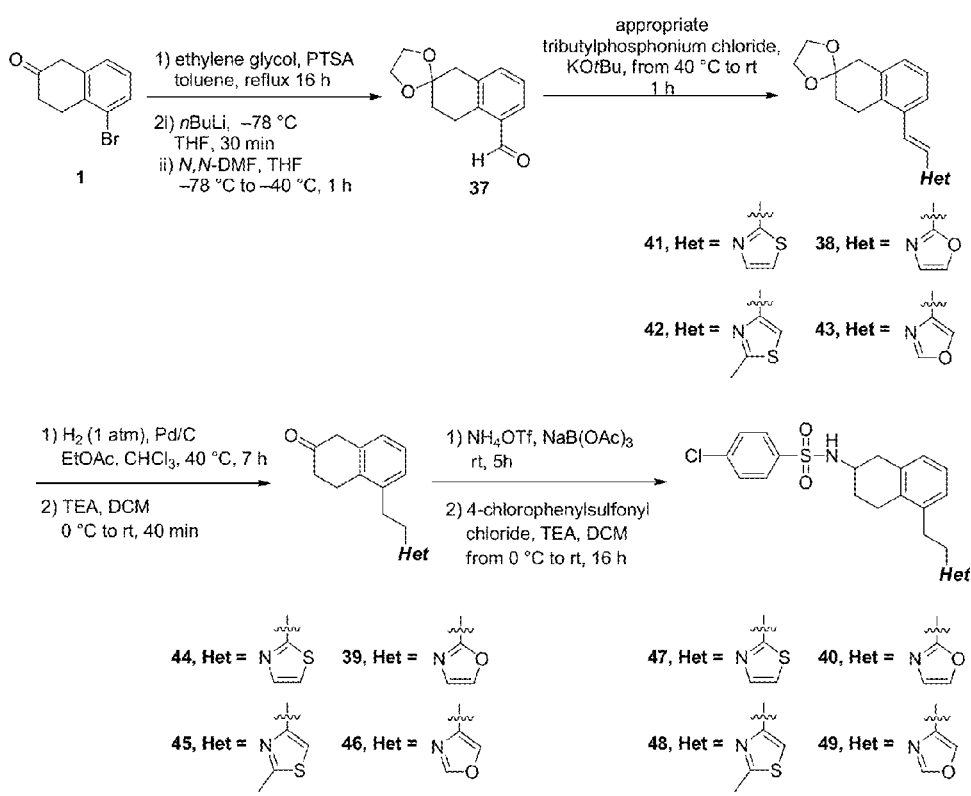
FIG. 15 is a schematic representation of a synthetic route to generate compounds of the invention.

The synthesis of oxazole and thiazole derivatives, illustrated in FIG. 15, started with the protection of ketone 2 as ketal, followed by a carbonylation reaction to obtain aldehyde 37. Next, Wittig olefination with the phosphonium salts of the appropriate heterocycles (Dondoni et al., 1988, Tetrahedron 44:2021-2031) furnished intermediates 38 and 41-43. Catalytic hydrogenation of the exocyclic double bond was then followed by TFA-mediated removal of the ketal (39 and 44-46). Finally, reductive amination of the ketone in the presence of ammonium trifluoroacetate and sodium triacetoxyborohydride generated the primary amine, which was directly used in the sulfonylation reaction to obtain the desired compounds (40 and 47-49). All new compounds were evaluated for antagonist activity utilizing the IP1 assay with the hTP and mTP receptor-expressing cells, with the results summarized in Table 5.

TABLE 5

Activities of Novel THN TP Receptor Antagonists as Assessed Using the IP1 Assay with Cells Expressing the hTP and mTP Receptors Stimulated with 0.2 nM I-BOP Core structure: 4-chlorophenyl-SO$_2$-NH-tetrahydronaphthalene with -CH$_2$CH$_2$-X substituent

| Compound | X | hIP1 IC$_{50}$ (nM) | MIP1 IC$_{50}$ (nM) |
|---|---|---|---|
| CNDR-51280 | –C(CH$_3$)$_2$–C(=O)OH | 0.93 (+/−0.50) | 0.021 (+/−0.021) |
| CNDR-51279 | –C(CH$_3$)$_2$–(1H-tetrazol-5-yl) | 0.62 (+/−0.45) | ND |
| 47 | –C(=CH$_2$)–(thiazol-2-yl) | 347 (+/−92.0) | 87.5 (+/−23.3) |
| 48 | –C(=CH$_2$)–(2-methylthiazol-4-yl) | 370 (+/−249) | 118 (+/−79.6) |
| 40 | –C(=CH$_2$)–(oxazol-2-yl) | 512 (+/−190) | 92.2 (+/−15.4) |
| 49 | –C(=CH$_2$)–(oxazol-4-yl) | 1030 (+/−365) | 159 (+/−71.8) |

Values are the means of at least three independent analyses, with associated SD.
ND = not determined.

The parent carboxylate-containing compound CNDR-51280 was found to be an extremely potent TP receptor antagonist, which blocked IBOP-induced IP1 production with an IC$_{50}$ of 0.93(±0.54) nM and 0.021(±0.021) nM using the hTP and mTP receptor-expressing cells. Like other anionic TP receptor antagonists, CNDR-51280 did not efficiently cross the BBB, with a B/P ratio of 0.02 1 h after IP injection into mice (Table 6).

TABLE 6

Evaluation of the Brain Penetration of Novel THN TP Receptor Antagonists

Core structure: 4-chlorophenyl-SO$_2$-NH-tetrahydronaphthalene with -CH$_2$CH$_2$-X substituent

| Compound | X | Plasma (nM) | Brain (nM) | B/P |
|---|---|---|---|---|
| CNDR-51280 | –C(CH$_3$)$_2$–C(=O)OH | 10375.7 (+/−3480.4) | 212.9 (+/−45.5) | 0.022 |
| CNDR-51279 | –C(CH$_3$)$_2$–(1H-tetrazol-5-yl) | 865 (+/−334) | 8.3 (+/−2.4) | 0.012 |
| 47 | –C(=CH$_2$)–(thiazol-2-yl) | 163 (+/−16) | 198 (+/−17) | 1.2 |
| 48 | –C(=CH$_2$)–(2-methylthiazol-4-yl) | 152 (+/−57) | 290 (+/−141) | 1.84 |
| 40 | –C(=CH$_2$)–(oxazol-2-yl) | 242 (+/−34) | 127 (+/−16) | 0.53 |
| 49 | –C(=CH$_2$)–(oxazol-4-yl) | 163 (+/−34) | 298 (+/−33) | 1.9 |

Compounds were administered at 5 mg/kg to mice. Drug levels were assessed by LC-MS/MS from brain and plasma samples obtained 1 h after dosing. Values represent mean ± SD. B/P = brain/plasma ratio.

Figure 16:
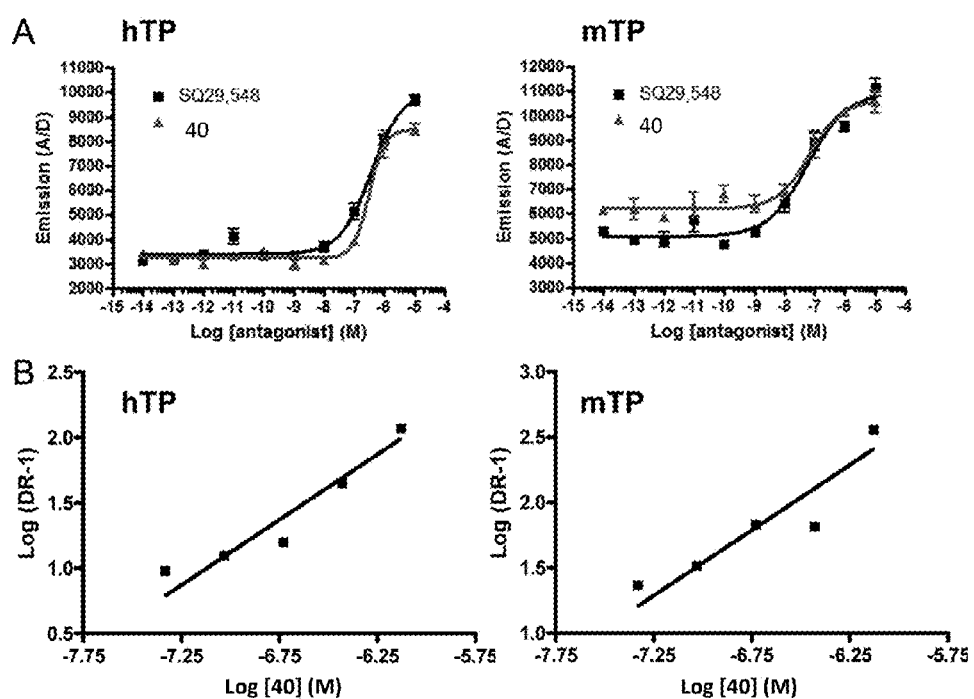
FIG. 16, comprising

Substitution of the carboxylic acid functionality of CNDR-51280 with a tetrazole yielded a compound (CNDR-51279) with comparable antagonist activity to CNDR-51280 in the hTP receptor-expressing cells (Table 5). However, like CNDR-51280, the tetrazole-containing analogue CNDR-51279 had poor BBB-permeability, with a B/P ratio of 0.01 (Table 6), and thus this compound did not undergo analysis in the mTP receptor assay. Replacing the carboxylic acid moiety of CNDR-51280 with nonacidic thiazoles (47 and 48) or oxazoles (40 and 49) resulted in analogues that blocked I-BOP-induced IP1 production in cells expressing the hTP and mTP receptors (Table 5) with superior $IC_{50}$ values. However, as illustrated in Table 6, compounds 40 and 47-49 exhibited excellent brain penetration, with B/P ratios of at least 0.5 1 h after drug administration. A direct comparison of the activity of 40 and the prototype TP receptor antagonist, SQ-29,548, in the IP1 assays revealed that both compounds had comparable $IC_{50}$ values of 300-400 and 50-100 nM in cells expressing the hTP and mTP receptors, respectively (FIG. 16A and Table 4). As SQ-29,548 was demonstrated to have low nanomolar affinity for the TP receptors as measured by radio-ligand binding and Schild analyses (FIG. 14), and without wishing to be bound by any particular theory, it appears that the $IC_{50}$ values obtained in the IP1 functional assays underestimate receptor affinity, likely due to receptor reserve resulting from the high levels of receptor expression.

Figure 17:
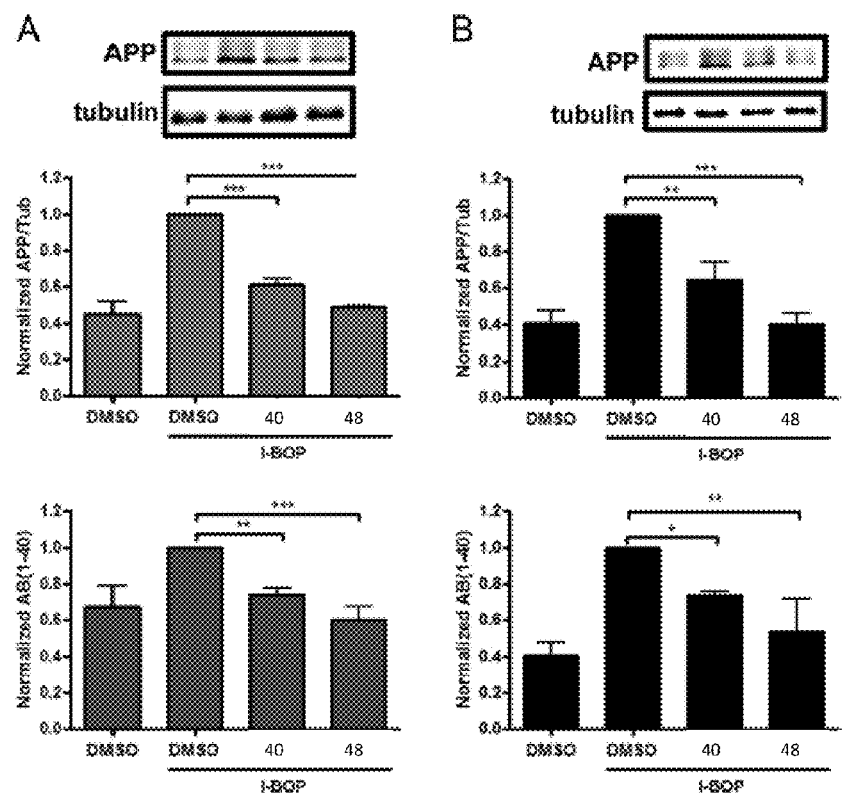
FIG. 17, comprising

Consequently, Schild analyses were performed with 40 to obtain a better approximation of receptor binding affinity. The results revealed apparent $K_d$ values of 6 nM for the hTP receptor and 3 nM for the mTP receptor (FIG. 16B), confirming that this compound binds with relatively high affinity at the TP receptors. Given that the thiazole and oxazole heterocyclic THN compounds displayed similar $IC_{50}$ values in the IP1 assays, and without wishing to be bound by any particular theory, it is likely that all of these brain-penetrant analogues interact at the hTP and mTP receptors with comparable affinity. The ability of these heterocyclic congeners of CNDR-51280 to bind to the TP receptor with moderately high affinity is interesting, as the carboxylic acid moiety of TP receptor antagonists is thought to be a critical contributor to the stability of the drug-receptor complex via ionic interaction with arginine residue 295 of the TP receptor (Funk et al., 1993, Mol. Pharmacol. 44:934-939). The identification of reasonably potent TP receptor antagonists with excellent brain penetration indicates that these or related analogues may be further developed for central nervous system indications such as AD. To confirm that such compounds have an inhibitory effect on APP expression and Aβ release, cells expressing hAPP and the TP receptor were treated with I-BOP in the absence or presence of 40 or 48. Both of these TP receptor antagonists significantly inhibited the I-BOP-induced increases of APP protein expression and Aβ(1-40) production by cells expressing the hTP (FIG. 17A) or mTP (FIG. 17B) receptors.

Example 12

Synthetic Protocols

Compound Synthesis

All solvents were reagent grade. All reagents were purchased from Aldrich or Acros and used as received. Thin layer chromatography (TLC) was performed with 0.25 mm E. Merck precoated silica gel plates. Flash chromatography was performed with silica gel 60 (particle size 0.040-0.062 mm) supplied by Silicycle and Sorbent Technologies. Spots were detected by viewing under a UV light. Yields refer to chromatographically and spectroscopically pure compounds. Infrared spectra were recorded on a Jasco model FT/IR-480 Plus spectrometer. Proton ($^1$H) and carbon ($^{13}$C) NMR spectra were recorded on a Bruker AMX-500 spectrometer. Chemical shifts were reported relative to solvents. High-resolution mass spectra were measured at the University of Pennsylvania Mass Spectrometry Service on a Waters LCT Premier XE LC/MS system. Analytical reversed-phased (Sunfire C18; 4.6×50 mm, 5 mL) high-performance liquid chromatography (HPLC) was performed with a Water binary gradient module 2525 equipped with Waters 2996 PDA and Water micromass ZQ. All samples were analyzed employing a linear gradient from 10% to 90% of acetonitrile in water over 8 min and flow rate of 1 mL/min. Preparative reverse phase HPLC purification was performed on a Gilson HPLC system equipped with Gilson 333 pumps, a 215 Liquid Handler, 845Z injection module, and UV detector, employing Waters SunFire prep C18 OBD columns (5 μm 19×50 or 19×100 mm). All samples were purified employing a linear gradient from 10% to 90% of acetonitrile in water over 15 min and flow rate of 20 mL/min. Unless otherwise stated, all final compounds were found to be >95% as determined by HPLC/MS and NMR. All compounds were synthesized as racemic mixtures.

3',4'-Dihydro-1'H-spiro[[1,3]dioxolane-2,2'-naphthalene]-5'-carbaldehyde, designated as 37 in FIG. 15, was prepared as follows: A solution of 5-bromo-3,4-dihydronaphthalen-2(1H)-one (625 mg, 2.78 mmol), ethylene glycol (0.23 mL, 4.17 mmol), and p-toluenesulfonic acid (5.70 mg, 0.03 mol) in benzene (46 mL) was stirred and heated to reflux for 10 h. The solution was cooled, diluted with ether, and sequentially washed with saturated aqueous sodium bicarbonate solution and water. The organic layer was dried over magnesium sulfate, filtered and concentrated in vacuo. Purification by silica gel column chromatography, using a 2:1 mixture of hexanes and AcOEt as eluant, furnished 5'-bromo-3',4'-dihydro-1'H-spiro[[1,3]-dioxolane-2,2'-naphthalene](730.4 mg, 98% yield) as a yellow oil. Yield: 65%.

$^1$H NMR (500 MHz; CDCl$_3$): δ 1.98 (t, J=6.9 Hz, 2H), 3.00 (d, J=6.4 Hz, 4H), 4.03 (s, 4H), 6.97-7.01 (m, 2H), 7.40 (dd, J=7.1, 1.9 Hz, 1H) ppm. $^{13}$C NMR (126 MHz; CDCl$_3$): δ 29.3, 31.6, 39.3, 64.6, 107.8, 125.2, 127.2, 128.5, 130.3, 134.9, 136.8 ppm.

To a solution of 5'-bromo-3',4'-dihydro-1'H-spiro[[1,3]dioxolane-2,2'-naphthalene](2.01 g, 7.47 mmol) in anhydrous tetrahydrofuran (74 mL) was added n-BuLi (2.50 M in hexane, 4.48 mL, 11.2 mmol) at −78° C. under nitrogen atmosphere. The mixture was stirred for 10 min at −78° C. under nitrogen atmosphere and then added with anhydrous N,N-dimethylformamide (0.86 mL, 11.2 mmol) in anhydrous tetrahydrofuran (1 mL) at −78° C. The reaction mixture was stirred for 1 h, allowing the temperature to rise to −40° C., and then it was quenched by addition of saturated aqueous ammonium chloride solution. The mixture was extracted with ethyl acetate. The combined organic layers were washed with brine, dried over magnesium sulfate, filtered, and concentrated in vacuum. Purification by silica gel column chromatography, using a 5:1 mixture of hexanes/ethyl acetate as eluant, furnished the desired aldehyde (1.23 g, 75%) as a colorless oil.

$^1$H NMR (500 MHz; CDCl$_3$): δ 1.99 (t, J=6.8 Hz, 2H), 3.05 (s, 2H), 3.44 (t, J=6.8 Hz, 2H), 4.04 (s, 4H), 7.29-7.34 (m, 2H), 7.66 (dd, J=7.1, 1.7 Hz, 1H), 10.24 (s, 1H) ppm. $^{13}$C NMR (126 MHz; CDCl$_3$): δ 25.3, 31.1, 39.5, 64.6, 107.2, 126.2, 131.6, 133.8, 135.1, 136.5, 137.8, 193.0 ppm.

General Procedure for the Synthesis of 38 and 41-43 of FIG. 15 is as follows: To a suspension of the appropriate phosphonium chloride (0.25 mmol) in anhydrous tetrahydrofuran (1.0 mL) was added potassium tert-butoxide (1.0 M in tetrahydrofuran, 0.44 mL, 0.44 mmol) at 0° C. The mixture was stirred for 10 min at 0° C. and then cooled to −40° C. To this stirring mixture, a solution of the 3',4'-dihydro-1'H-spiro[[1,3]dioxolane-2,2'-naphthalene]-5'-carbaldehyde (50 mg, 0.23 mmol) in anhydrous tetrahydrofuran (1.3 mL) was added dropwise. The reaction mixture was stirred for 40 min while allowing the temperature to gradually rise to room temperature. The reaction mixture was quenched by addition of saturated aqueous ammonium chloride solution and extracted with ether. The organic layer was washed with saturated aqueous ammonium chloride solution, dried over magnesium sulfate, filtered, and concentrated in vacuum. Purification by silica gel column chromatography, using a 2:1 mixture of hexanes/AcOEt as eluant, furnished the desired compound.

(E)-2-(2-(3',4'-Dihydro-1'H-spiro[[1,3]dioxolane-2,2'-naphthalen]-5'-yl)vinyl)oxazole, designated as 38 in FIG. 15: Yield: 78%.

$^1$H NMR (500 MHz; CDCl$_3$): δ 2.00 (t, J=6.8 Hz, 2H), 3.02 (s, 2H), 3.09 (t, J=6.8 Hz, 2H), 4.03 (d, J=1.3 Hz, 4H), 6.84 (d, J=16.2 Hz, 1H), 7.05 (d, J=7.6 Hz, 1H), 7.15-7.18 (m, 2H), 7.43 (d, J=7.4 Hz, 1H), 7.62 (s, 1H), 7.77 (d, J=16.2 Hz, 1H) ppm. $^{13}$C NMR (126 MHz; CDCl$_3$): δ 25.7, 31.5, 39.5, 64.58, 107.7, 115.5, 123.9, 126.3, 128.5, 130.4, 133.8, 134.4, 135.3, 138.1, 161.9 ppm.

(E)-2-(2-(3',4'-Dihydro-1'H-spiro[[1,3]dioxolane-2,2'-naphthalen]-5'-yl)vinyl)thiazole, designated as 41 in FIG. 15: Yield: 95%.

$^1$H NMR (500 MHz; CDCl$_3$): δ 1.54 (s, 2H), 2.01 (t, J=6.8 Hz, 2H), 3.02 (s, 2H), 3.10 (t, J=6.8 Hz, 2H), 4.03-4.05 (m, 4H), 7.05 (d, J=7.6 Hz, 1H), 7.15-7.19 (m, 2H), 7.25 (d, J=3.3 Hz, 1H), 7.45 (d, J=7.7 Hz, 1H), 7.70 (d, J=16.0 Hz, 1H), 7.80 (d, J=3.3 Hz, 1H) ppm.

(E)-4-(2-(3',4'-Dihydro-1'H-spiro[[1,3]dioxolane-2,2'-naphthalen]-5'-yl)vinyl)-2-methylthiazole, designated as 42 in FIG. 15: Yield: 93%.

$^1$H NMR (500 MHz; CDCl$_3$): δ 2.00 (t, J=6.8 Hz, 2H), 2.74 (s, 3H), 3.02 (s, 2H), 3.11 (t, J=6.8 Hz, 2H), 4.03 (d, J=2.1 Hz, 4H), 6.90 (d, J=15.7 Hz, 1H), 6.99 (d, J=9.9 Hz, 2H), 7.14 (t, J=7.6 Hz, 1H), 7.40 (d, J=7.7 Hz, 1H), 7.66 (d, J=15.7 Hz, 1H) ppm.

(E)-4-(2-(3',4'-Dihydro-1'H-spiro[[1,3]dioxolane-2,2'-naphthalen]-5'-yl)vinyl)oxazole, designated as 43 in FIG. 15: Yield: 94%.

$^1$H NMR (500 MHz; CDCl$_3$): δ 1.99 (t, J=6.8 Hz, 2H), 3.01 (s, 2H), 3.09 (t, J=6.8 Hz, 2H), 4.03 (d, J=1.3 Hz, 4H), 6.79 (d, J=15.8 Hz, 1H), 7.00 (d, J=7.6 Hz, 1H), 7.14 (t, J=7.6 Hz, 1H), 7.39 (d, J=7.7 Hz, 1H), 7.58 (d, J=15.8 Hz, 1H), 7.65 (s, 1H), 7.87 (d, J=0.5 Hz, 1H) ppm.

General Procedure for the Synthesis of 39 and 44-46 of FIG. 15: A mixture containing the appropriate olefin (0.39 mmol), 10% Pd/C (40 mg), ethyl acetate (25 mL), and chloroform (1 mL) was stirred under hydrogen atmosphere at 40° C. for 7 h and then filtered through a pad of Celite. The filtered solution was then evaporated to dryness, obtaining the saturated intermediate in >95% yield, which was used directly for the next step. Thus, trifluoroacetic acid (0.5 mL) was added dropwise to solution of the appropriate ketal (0.35 mmol) in dichloromethane (3 mL) at 0° C. The reaction mixture was then stirred for 40 min, allowing the temperature to rise to room temperature. The reaction was quenched by addition of saturated aqueous solution of sodium bicarbonate at 0° C., and the resulting mixture was extracted with dichloromethane. The combined organic layers were washed with saturated aqueous solution of sodium bicarbonate, dried over magnesium sulfate, and concentrated in vacuo. Purification by silica gel column chromatography, using a 2:1 mixture of hexanes/AcOEt as eluent, furnished the desired compound.

5-(2-(Oxazol-2-yl)ethyl)-3,4-dihydronaphthalen-2(1H)-one, designated as 39 in FIG. 15: Yield: 71%.

$^1$H NMR (500 MHz; CDCl$_3$): 2.51 (t, J=6.6 Hz, 2H), 3.08-3.02 (m, 4H), 3.16 (dd, J=9.2, 6.7 Hz, 2H), 3.58 (s, 2H), 7.03-7.00 (m, 2H), 7.10 (d, J=6.8 Hz, 1H), 7.15 (t, J=7.5 Hz, 1H), 7.57 (d, J=0.8 Hz, 1H) ppm. $^{13}$C NMR (126 MHz; CDCl3): δ 24.1, 29.4, 30.5, 37.9, 45.7, 126.92, 126.99, 127.03, 127.7, 134.0, 135.0, 137.4, 138.4, 163.9, 210.6 ppm.

5-(2-(Thiazol-2-yl)ethyl)-3,4-dihydronaphthalen-2(1H)-one, designated as 44 in FIG. 15: Yield: 62%.

$^1$H NMR (500 MHz; CDCl$_3$): δ 2.48 (t, J=6.6 Hz, 2H), 3.06 (t, J=6.6 Hz, 2H), 3.20 (m, 2H), 3.30-3.27 (m, 2H), 3.59 (s, 2H), 7.01 (d, J=7.2 Hz, 1H), 7.15 (dt, J=14.2, 7.1 Hz, 2H), 7.20 (d, J=3.3 Hz, 1H), 7.71 (d, J=3.3 Hz, 1H) ppm 5-(2-(2-Methylthiazol-4-yl)ethyl)-3,4-dihydronaphthalen-2(1H)-one, designated as 45 in FIG. 15: Yield: 31%.

$^1$H NMR (500 MHz; CDCl$_3$): δ 2.45 (t, J=6.6 Hz, 2H), 2.71 (s, 3H), 2.97 (dd, J=9.4, 6.3 Hz, 2H), 3.09-3.02 (m, 4H), 3.57 (s, 2H), 6.64 (s, 1H), 6.99 (d, J=7.2 Hz, 1H), 7.13 (m, 2H) ppm.

5-(2-(Oxazol-4-yl)ethyl)-3,4-dihydronaphthalen-2(1H)-one, designated as 46 in FIG. 15: Yield: 50%.

$^1$H NMR (500 MHz; CDCl$_3$): δ 2.48 (t, J=6.6 Hz, 2H), 2.81 (t, J=7.9 Hz, 2H), 3.07-3.02 (m, 4H), 3.58 (s, 2H), 7.00 (d, J=7.3 Hz, 1H), 7.09 (d, J=7.2 Hz, 1H), 7.14 (d, J=7.5 Hz, 1H), 7.88 (s, 1H), 7.36 (s, 1H) ppm. $^{13}$C NMR (126 MHz; CDCl3): δ 24.1, 27.5, 32.0, 37.9, 45.7, 126.6, 126.8, 127.9, 133.8, 134.6, 135.1, 138.2, 139.4, 151.1, 210.8 ppm.

Figure 13:
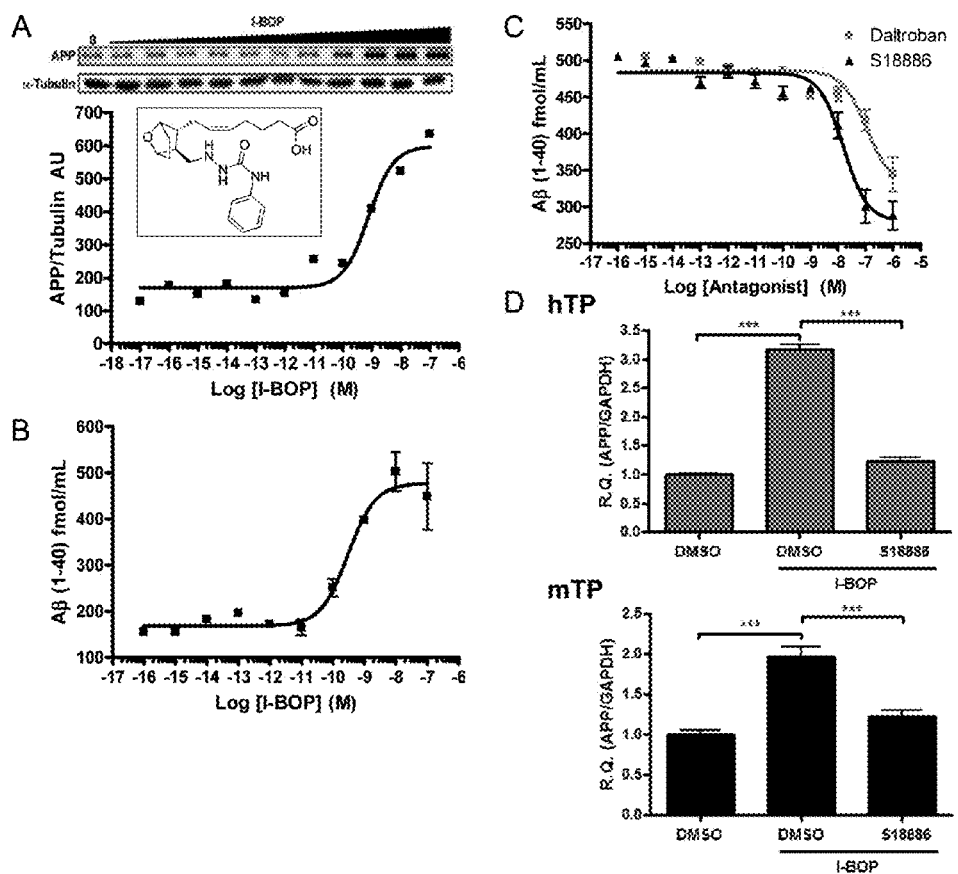
FIG. 13, comprising

General Procedure for the Synthesis of 40 and 47-49 of FIG. 13: A solution of the appropriate ketone (0.19 mmol) and ammomium trifluoroacetate (50 mg, 0.23 mmol) in tetrahydrofuran (0.3 mL) was stirred for 20 min at room temperature. The reaction mixture was then added with sodium triacetoxyborohydride (50 mg, 0.23 mmol) and stirred at room temperature for 5 h. The reaction was then quenched by addition of 1 mL of concentrated hydrochloric acid. The reaction mixture was vigorously stirred for 15 min and then diluted with water (8 mL) and extracted with ether. The combined organic layers were dried over magnesium sulfate, filtered, and concentrated in vacuo to give the amine intermediate, which was used directly for the next step. Thus, to a solution of the appropriate amine (0.068 mmol) in 0.7 mL of dry dichloromethane and triethylamine (10 μL, 0.07 mmol) was added 4-chloro-benzenesulfonyl chloride (15 mg, 0.07 mmol) with stirring at 0° C. The reaction mixture was stirred for 16 h, allowing the temperature to rise to room temperature. The reaction was quenched by addition of saturated aqueous solution of ammonium chloride. The resulting mixture was extracted with dichloromethane. The combined organic layers were washed with saturated aqueous solution of ammonium chloride, dried over magnesium sulfate, and concentrated in vacuo. Purification by silica gel preparative TLC using a 2:1 mixture of hexane/AcOEt as eluent furnished the desired compound.

4-Chloro-N-(2-(oxazol-2-yl)ethyl)-1,2,3,4-tetrahydronaphthalen-2-yl)benzenesulfonamide, designated as 40 in FIG. 15: Yield: 23% over two steps.

$^1$H NMR (500 MHz; CDCl$_3$): δ 1.84-1.76 (m, 1H), 2.02-1.96 (m, 1H), 2.64 (dd, J=16.2, 7.6 Hz, 1H), 2.77-2.72 (m, 1H), 2.82 (dd, J=15.0, 8.7 Hz, 1H), 3.01-2.95 (m, 1H), 3.04-3.03 (m, 3H), 3.70 (m, 1H), 4.66 (d, J=7.9 Hz, 1H), 6.86 (d, J=7.4 Hz, 1H), 7.05 (m, 3H), 7.51 (d, J=8.7 Hz, 2H), 7.58 (d, J=0.8 Hz, 1H), 7.84 (d, J=8.7 Hz, 2H) ppm. $^{13}$C NMR (126 MHz; CDCl$_3$): δ 23.6, 28.4, 29.5, 29.8, 37.0, 49.1, 126.3, 126.87, 127.00, 128.1, 128.4, 129.5, 133.0, 133.4, 138.38, 138.47, 139.1, 139.7, 164.1 ppm. IR: ν 3274, 2926, 1576 cm$^{-1}$. HRMS: calculated for C$_{21}$H$_{22}$N$_2$O$_3$SCl$^+$, 417.1040. found, 417.1031.

4-Chloro-N-(5-(2-(thiazol-2-yl)ethyl)-1,2,3,4-tetrahydronaphthalen-2-yl)benzenesulfonamide, designated as 47 in FIG. 15: Yield: 18% over two steps. $^1$H NMR (500 MHz; CDCl3): δ 1.81-1.73 (m, 1H), 1.96 (m, 1H), 2.63 (dd, J=16.2, 7.5 Hz, 1H), 2.75 (m, 2H), 2.97 (dd, J=16.2, 4.7 Hz, 1H), 3.06-3.03 (m, 2H), 3.32-3.21 (m, 2H), 3.71-3.66 (m, 1H), 4.62 (d, J=7.9 Hz, 1H), 6.84 (d, J=7.4 Hz, 1H), 7.05 (m, 2H), 7.21 (d, J=3.3 Hz, 1H), 7.49 (d, J=8.7 Hz, 2H), 7.70 (d, J=3.3 Hz, 1H), 7.82 (d, J=8.7 Hz, 2H) ppm. $^{13}$C NMR (126 MHz; CDCl3): δ 23.9, 29.6, 33.0, 33.7, 37.1, 49.2, 118.6, 126.5, 127.3, 128.6, 128.2, 129.7, 133.3, 133.6, 138.7, 139.3, 139.7, 142.5, 170.2 ppm. IR: ν 3276, 3085, 2930, 1581 cm$^{-1}$. HRMS: calculated for $C_{21}H_{22}N_2O_2S_2Cl+$, 433.0811. found, 433.0800

4-Chloro-N-(5-(2-(2-methylthiazol-4-yl)ethyl)-1,2,3,4-tetrahydronaphthalen-2-yl)benzenesulfonamide, designated as 48 in FIG. 15: Yield: 42% over two steps. $^1$H NMR (500 MHz; CDCl$_3$): δ 1.80-1.73 (m, 1H), 1.97 (m, 1H), 2.63 (dd, J=16.2, 7.7 Hz, 1H), 2.71 (dd, J=24.4, 7.1 Hz, 4H), 2.81 (dq, J=15.9, 5.0 Hz, 1H), 2.98-2.90 (m, 5H), 3.67 (m, 1H), 4.61 (d, J=7.8 Hz, 1H), 6.66 (s, 1H), 6.82 (d, J=7.2 Hz, 1H), 7.04 (m Hz, 2H), 7.49 (d, J=8.6 Hz, 2H), 7.82 (d, J=8.6 Hz, 2H) ppm. $^{13}$C NMR (126 MHz; CDCl$_3$): δ 19.2, 23.7, 29.6, 31.9, 32.3, 37.0, 49.2, 112.7, 126.2, 127.1, 127.6, 128.5, 129.4, 133.04, 133.20, 139.1, 139.69, 139.71, 156.1, 165.6 ppm. IR: ν 3281, 2925, 1588 cm-1. HRMS: calculated for $C_{22}H_{24}N_2O_2S_2Cl^+$, 447.0068. found, 447.0963

4-Chloro-N-(5-(2-(oxazol-4-yl)ethyl)-1,2,3,4-tetrahydronaphthalen-2-yl)benzenesulfonamide, designated as 49 in FIG. 15. Yield: 29% over two steps. $^1$H NMR (500 MHz; CDCl$_3$): δ 1.81-1.74 (m, 1H), 2.00-1.95 (m, 1H), 2.62 (dd, J=16.2, 7.5 Hz, 1H), 2.83-2.69 (m, 4H), 2.90-2.85 (m, 2H), 3.01-2.94 (m, 1H), 3.69 (m, 1H), 4.58 (d, J=7.9 Hz, 1H), 6.83 (d, J=7.5 Hz, 1H), 7.01 (d, J=6.8 Hz, 1H), 7.06 (t, J=7.5 Hz, 1H), 7.37 (d, J=0.9 Hz, 1H), 7.49 (d, J=8.6 Hz, 2H), 7.84-7.81 (m, 3H) ppm. $^{13}$C NMR (126 MHz; CDCl$_3$): δ 23.7, 26.5, 29.5, 31.4, 37.0, 49.2, 126.2, 127.1, 127.8, 128.4, 129.4, 133.0, 133.3, 134.4, 139.1, 139.4, 139.7, 151.0 ppm. IR: ν 3277, 2926, 1588 cm$^{-1}$. HRMS: calculated for $C_{21}H_{21}N_2O_3NaSCl^+$, 439.0859. found, 439.0858.

Example 13

Synthetic Protocols

Figure 18:
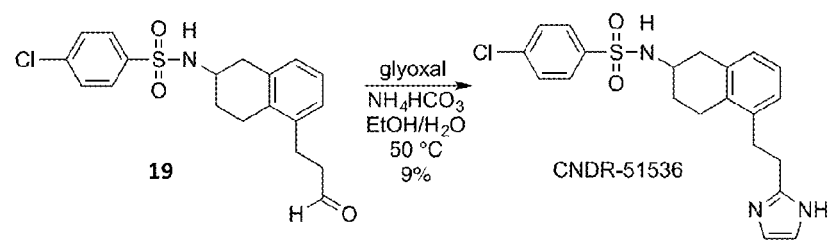
FIG. 18 is a schematic representation of a synthetic route to generate compounds of the invention.

N-(5-(2-(1H-imidazol-2-yl)ethyl)-1,2,3,4-tetrahydronaphthalen-2-yl)-4-chlorobenzenesulfonamide, designated as CNDR-51536 in FIG. 18, is prepared as follows: To a mixture of aldehyde 19 (26.4 mg, 0.070 mmol) in EtOH/H$_2$O (1:1, 1.4 mL) at rt was added glyoxal (24 μL, 40% wt, 0.21 mmol) and NH$_4$HCO$_3$ (33.1 mg, 0.42 (mmol). The reaction mixture was then stirred at 50° C. for 4 h until completion. The resulting mixture was diluted with H$_2$O (5.0 mL) and extracted with CH$_2$Cl$_2$ (3×5.0 mL) The combined organic layers were dried over Na$_2$SO$_4$ and concentrated. The crude material was then purified by HPLC to give the product as a white solid (2.7 mg, 9%).

$^1$H NMR (500 MHz; CD$_3$OD): δ 7.88 (d, J=8.65 Hz, 2H), 7.59 (d, J=8.65 Hz, 2H), 6.98 (t, J=7.55 Hz, 1H), 6.86-6.82 (m, 2H), 3.49-3.43 (m, 1H), 3.06-3.03 (m, 2H), 2.99-2.95 (m, 2H), 2.88-2.84 (m, 2H), 2.68-2.61 (m, 2H), 1.97-1.92 (m, 1H), 1.74-1.66 (m, 1H) ppm. $^{13}$C NMR (125 MHz; CD$_3$OD): δ 148.90, 142.08, 139.70, 138.87, 135.90, 134.53, 130.46, 129.66, 129.05, 127.84, 127.15, 120.99, 50.76, 37.91, 32.16, 31.03, 28.42, 25.53 ppm. HRMS: ESI$^+$, calculated for $C_{21}H_{23}ClN_3O_2S^+$ 416.1200. found 416.1201. IR: ν 3412.4, 1706.7, 1591.0, 1362.5 cm$^{-1}$.

Figure 19:
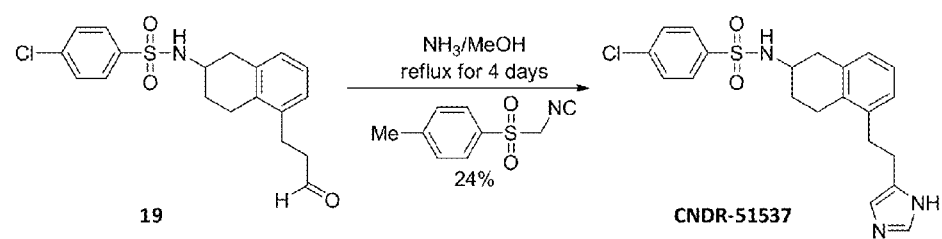
FIG. 19 is a schematic representation of a synthetic route to generate compounds of the invention.

N-(5-(2-(1H-imidazol-5-yl)ethyl)-1,2,3,4-tetrahydronaphthalen-2-yl)-4-chlorobenzenesulfonamide, designated as CNDR-51537 in FIG. 19, is prepared as follows: To a solution of aldehyde 19 (31.0 mg, 0.082 mmol) in ammonia MeOH solution (7.0M, 1.6 mL) at rt was added toluenesulfonylmethyl isocyanide (48.0 mg, 0.25 mmol) in one portion. The resulting mixture was then stirred at 60° C. for 4 days. The reaction mixture was diluted with H$_2$O (3.0 mL), and extracted with CH$_2$Cl$_2$ (3×3.0 mL) The combined organic layers were dried over Na$_2$SO$_4$ and concentrated. The crude material was then purified by HPLC to give the product as a white solid (8.1 mg, 24%). $^1$H NMR (500 MHz; CD$_3$OD): δ 8.14 (bs, 1H), 7.88 (d, J=8.70 Hz, 2H), 7.58 (d, J=8.7 Hz, 2H), 7.00-6.96 (m, 2H), 6.92 (bd, J=7.10 Hz, 1H), 6.80 (bd, J=7.40 Hz, 1H), 3.50-3.44 (m, 1H), 2.91-2.83 (m, 6H), 2.68-2.62 (m, 2H), 1.95-1.91 (m, 1H), 1.73-1.65 (m, 1H) ppm. $^{13}$C NMR (125 MHz; CD$_3$OD): δ 142.10, 139.89, 139.66, 136.56, 135.60, 135.12, 134.46, 130.44, 129.64, 128.65, 127.90, 126.98, 117.40, 50.80, 37.92, 33.29, 31.05, 27.09, 25.57 ppm. HRMS: ESI$^+$, calculated for $C_{21}H_{23}ClN_3O_2S^+$ 416.1200. found 416.1198. IR: ν 3139.5, 2066.4, 1588.1 cm$^{-1}$.

Figure 20:
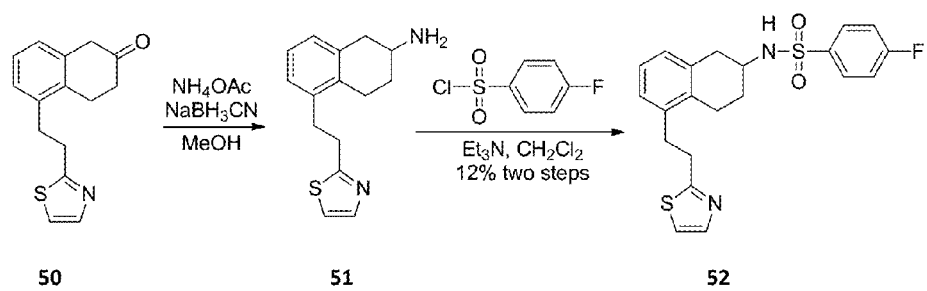
FIG. 20 is a schematic representation of a synthetic route to generate compounds of the invention.

4-Fluoro-N-(5-(2-(thiazol-2-yl)ethyl)-1,2,3,4-tetrahydronaphthalen-2-yl)benzenesulfonamide, designated as 52 in FIG. 20, is prepared as follows: To a solution of the ketone designated as 50 in FIG. 8 (32.7 mg, 0.13 mmol) in MeOH (3.2 mL) at rt was added NH$_4$OAc (68.6 mg, 0.89 mmol), followed by NaBH$_3$CN (12.0 mg, 0.19 mmol). The reaction mixture was then stirred at 40° C. for 3.5 hours and quenched with saturated NaHCO$_3$ solution (5.0 mL). The resulting mixture was extracted with CH$_2$Cl$_2$ (3×5.0 mL). The combined organic layers were dried over Na$_2$SO$_4$, and concentrated to give the crude product 51, which was used directly in the next step.

To a solution of the crude amine 51 from the previous step in CH$_2$Cl$_2$ (3.2 mL) at 0° C. was added Et$_3$N (53 μL, 0.38 mmol) and 4-fluoro benzenesulfonyl chloride (39.6 mg, 0.20 mmol). The reaction mixture was then warmed to rt and stirred for 2 h until completion. The reaction mixture was quenched with saturated NaHCO$_3$ solution (5.0 mL) and the resulting mixture was extracted with CH$_2$Cl$_2$ (3×5.0 mL). The combined organic layers were dried over Na$_2$SO$_4$ and concentrated. The crude product was then purified via column chromatography (3:2 hexanes/EtOAc) to give the pure product as a yellow solid (6.2 mg, 12%). $^1$H NMR (500 MHz; CDCl$_3$): δ 7.93-7.89 (m, 2H), 7.71 (d, J=2.15 Hz, 1H), 7.24-7.17 (m, 3H), 7.08-7.01 (m, 2H), 6.84 (bd, J=7.20 Hz, 1H), 4.72 (d, J=7.75 Hz, 1H), 3.71-3.64 (m, 1H), 3.34-3.22 (m, 2H), 3.10-2.99 (m, 2H), 2.95 (dd, J=16.2, 4.70 Hz, 1H), 2.83-2.76 (m, 1H), 2.75-2.68 (m, 1H), 2.63 (dd, J=16.3, 7.45 Hz, 1H), 1.99-1.93 (m, 1H), 1.81-1.73 (m, 1H) ppm. $^{13}$C NMR (125 MHz; CDCl$_3$): δ 166.01, 163.98, 141.49, 138.23, 137.16, 137.14, 133.58, 133.15, 129.72, 129.64, 128.14, 127.05, 126.27, 118.65, 116.44, 116.26, 48.94, 36.91, 33.19, 32.76, 29.32, 23.62 ppm. HRMS: ESI$^+$, calculated for $C_{21}H_{22}FN_2O_2S_2^+$ 417.1107. found 417.1116. IR: ν 2926.45, 1591.95, 1159.01 cm$^{-1}$.

The disclosures of each and every patent, patent application, and publication cited herein are hereby incorporated herein by reference in their entirety. While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A composition comprising a compound of Formula (I), or a salt or solvate thereof:

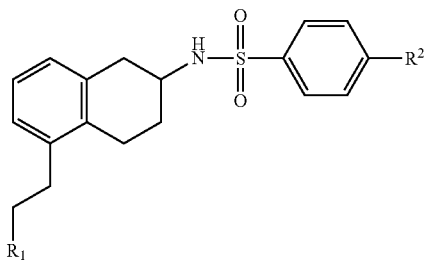

(I)

wherein:

$R^1$ is selected from the group consisting of

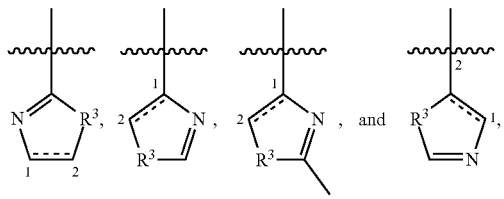

the bond between carbons 1 and 2 is either a single bond ($C^1$-$C^2$) or a double bond ($C^1$=$C^2$);

$R^2$ is selected from the group consisting of F, Cl, Br, I, and $CF_3$;

$R^3$ is selected from the group consisting of $NR^4$, S, and O;

$R^4$ is selected from the group consisting of H, —($C_1$-$C_6$ alkyl), —($C_1$-$C_6$ fluoroalkyl), —($C_1$-$C_6$ heteroalkyl), —($C_1$-$C_3$ alkyl)-($C_3$-$C_6$ cycloalkyl), —($C_1$-$C_3$ alkyl)-aryl, —($C_1$-$C_3$ alkyl)-heteroaryl, —C(=O)$R^5$, —$CO_2R^5$, and —CH(R)$_2$; and, each occurrence of $R^5$ is independently selected from the group consisting of H, —($C_1$-$C_6$ alkyl), —($C_1$-$C_6$ heteroalkyl), and —($C_1$-$C_3$ alkyl)-($C_3$-$C_6$ cycloalkyl), wherein the alkyl, heteroalkyl, or cycloalkyl group is optionally substituted.

2. The composition of claim 1, wherein the compound is selected from the group consisting of 4-chloro-N-(5-(2-(oxazol-2-yl)ethyl)-1,2,3,4-tetrahydronaphthalen-2-yl)benzenesulfonamide, 4-chloro-N-(5-(2-(thiazol-2-yl)ethyl)-1,2,3,4-tetrahydronaphthalen-2-yl)benzenesulfonamide, 4-chloro-N-(5-(2-(2-methylthiazol-4-yl)ethyl)-1,2,3,4-tetrahydronaphthalen-2-yl)benzenesulfonamide, 4-chloro-N-(5-(2-(oxazol-4-yl)ethyl)-1,2,3,4-tetrahydronaphthalen-2-yl)benzenesulfonamide, N-(5-(2-(1H-imidazol-2-yl)ethyl)-1,2,3,4-tetrahydronaphthalen-2-yl)-4-chlorobenzenesulfonamide, N-(5-(2-(1H-imidazol-5-yl)ethyl)-1,2,3,4-tetrahydronaphthalen-2-yl)-4-chlorobenzenesulfonamide, 4-fluoro-N-(5-(2-(thiazol-2-yl)ethyl)-1,2,3,4-tetrahydronaphthalen-2-yl)benzenesulfonamide, a salt thereof, a solvate thereof, and any combinations thereof.

* * * * *

SEQUENCE LISTING

<160> NUMBER OF SEQ ID NOS: 4

<210> SEQ ID NO 1
<211> LENGTH: 18
<212> TYPE: DNA
<213> ORGANISM: Artificial sequence
<220> FEATURE:
<223> OTHER INFORMATION: Chemically synthesized

<400> SEQUENCE: 1
ccgctctgca ggctgttc                                            18

<210> SEQ ID NO 2
<211> LENGTH: 26
<212> TYPE: DNA
<213> ORGANISM: Artificial sequence
<220> FEATURE:
<223> OTHER INFORMATION: Chemically synthesized

<400> SEQUENCE: 2
gcggacatac ttctttagca tattga                                   26

<210> SEQ ID NO 3
<211> LENGTH: 23
<212> TYPE: DNA
<213> ORGANISM: Artificial sequence
<220> FEATURE:
<223> OTHER INFORMATION: Chemically synthesized

<400> SEQUENCE: 3
gaaggtgaag gtcggagtca acg                                      23

<210> SEQ ID NO 4
<211> LENGTH: 24
<212> TYPE: DNA
<213> ORGANISM: Artificial sequence
<220> FEATURE:
<223> OTHER INFORMATION: Chemically synthesized

<400> SEQUENCE: 4
ccagagttaa aagcagccct ggtg                                     24